United States Patent
Foote et al.

(10) Patent No.: US 8,552,004 B2
(45) Date of Patent: Oct. 8, 2013

(54) CHEMICAL COMPOUNDS

(75) Inventors: Kevin Michael Foote, Macclesfield (GB); Paul Turner, Macclesfield (GB); Johannes Wilhelmus Maria Nissink, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 13/540,057

(22) Filed: Jul. 2, 2012

(65) Prior Publication Data

US 2013/0005725 A1    Jan. 3, 2013

Related U.S. Application Data

(63) Continuation of application No. 13/156,684, filed on Jun. 9, 2011, now Pat. No. 8,252,802.

(60) Provisional application No. 61/353,713, filed on Jun. 11, 2010.

(51) Int. Cl.
*A61K 31/506* (2006.01)
*C07D 403/14* (2006.01)

(52) U.S. Cl.
USPC ............................. 514/258.1; 544/253

(58) Field of Classification Search
USPC ..................................... 544/253; 514/258.1
See application file for complete search history.

(56) References Cited

U.S. PATENT DOCUMENTS

| | | | |
|---|---|---|---|
| 5,250,530 A | 10/1993 | Giencke et al. | |
| 2002/0086858 A1 | 7/2002 | Breu et al. | |
| 2007/0049603 A1 | 3/2007 | Miknis et al. | |
| 2007/0299068 A1 | 12/2007 | Karp et al. | |

FOREIGN PATENT DOCUMENTS

| | | |
|---|---|---|
| EP | 0407899 B1 | 3/1995 |
| EP | 1277738 A1 | 1/2003 |

(Continued)

OTHER PUBLICATIONS

William G. Kaelin Jr, 'The concept of synthetic lethality in the context of anticancer therapy', Nature Reviews Cancer, 2005, pp. 689-698, vol. 5.

(Continued)

*Primary Examiner* — Kamal Saeed
*Assistant Examiner* — Janet L Coppins

(57) ABSTRACT

There is provided pyrimidinyl compounds of Formula (I), wherein:
$R^2$ is or pharmaceutically acceptable salts thereof, processes for their preparation, pharmaceutical compositions containing them and their use in therapy.

10 Claims, 1 Drawing Sheet

(56) References Cited

FOREIGN PATENT DOCUMENTS

| EP | 1911753 A1 | 4/2008 |
|---|---|---|
| EP | 1970375 A1 | 9/2008 |
| EP | 2003131 A1 | 12/2008 |
| GB | 2431156 A | 4/2007 |
| JP | 200791649 A | 4/2007 |
| JP | 2007119450 A | 5/2007 |
| JP | 2007246474 A | 9/2007 |
| WO | 02/38551 A1 | 5/2002 |
| WO | 2004/048365 A1 | 6/2004 |
| WO | 2005/000404 A2 | 1/2005 |
| WO | 2006/005914 A1 | 1/2006 |
| WO | 2006/005915 A1 | 1/2006 |
| WO | 2006/005918 A1 | 1/2006 |
| WO | 2006/053227 A2 | 5/2006 |
| WO | 2006/124662 A1 | 11/2006 |
| WO | 2006/124874 A2 | 11/2006 |
| WO | 2006/125554 A1 | 11/2006 |
| WO | 2007/005673 * | 1/2007 |
| WO | 2007/005673 A1 | 1/2007 |
| WO | 2007/013691 A1 | 2/2007 |
| WO | 2007/041130 A2 | 4/2007 |
| WO | 2007/041358 A2 | 4/2007 |
| WO | 2007/042806 A1 | 4/2007 |
| WO | 2007/042810 A1 | 4/2007 |
| WO | 2007/049041 A1 | 5/2007 |
| WO | 2007/054831 A2 | 5/2007 |
| WO | 2007/063868 A1 | 6/2007 |
| WO | 2007/066099 A1 | 6/2007 |
| WO | 2007/066102 A1 | 6/2007 |
| WO | 2007/066103 A1 | 6/2007 |
| WO | 2007/072163 A2 | 6/2007 |
| WO | 2007/080382 A1 | 7/2007 |
| WO | 2007/084413 A2 | 7/2007 |
| WO | 2007/084786 A1 | 7/2007 |
| WO | 2007/089768 A2 | 8/2007 |
| WO | 2007/105023 A1 | 9/2007 |
| WO | 2007/114323 A1 | 10/2007 |
| WO | 2007/124288 A1 | 11/2007 |
| WO | 2007/126043 A1 | 11/2007 |
| WO | 2007/141571 A2 | 12/2007 |
| WO | 2008/005538 A2 | 1/2008 |
| WO | 2008/023159 A1 | 2/2008 |
| WO | 2008/023180 A1 | 2/2008 |
| WO | 2008/125833 A1 | 10/2008 |
| WO | 2009/007751 A2 | 1/2009 |

OTHER PUBLICATIONS

James W Janetka et al, 'Inhibitors of checkpoint kinases: From discovery to the clinic', Current Opinion in Drug Discovery & Development, 2007, pp. 473-486, vol. 10(4).
Jann N. Sarkaria et al, 'Inhibition of ATM and ATR Kinase Activities by the Radiosensitizing Agent, Caffeine', Cancer Research, 1999, pp. 4375-4382, vol. 59.
David Cortez et al, 'ATR and ATRIP: Partners in Checkpoint Signaling', Science, 2001, pp. 1713-1716, vol. 294.
Spencer J. Collis et al, 'Enhanced Radiation and Chemotherapy-mediated Cell Killing of Human Cancer Cells by small Inhibitory RNA Silencing of DNA Repair Factors', Cancer Research, 2003, pp. 1550-1554, vol. 63.
William A. Cliby et al, 'Overexpression of a kinase-inactive ATR protein causes sensitivity to DNA-damaging agents and defects in cell cycle checkpoints', The EMBO Journal, 1998, pp. 159-169, vol. 17(1).
PJ Hurley, D Wilsker & F Bunz, 'Human cancer cells require ATR for cell cycle progression following exposure to ionizing radiation' Oncogene, 2007, pp. 2535-2542, vol. 26.
Veronica Rodriguez-Bravo et al, 'Different S/M Checkpoint Responses of Tumor and Non-Tumor Cell Lines to DNA Replication Inhibition' Cancer Research, 2007, pp. 11648-11656, vol. 67.
Paul Nghiem et al, 'ATR inhibition selectively sensitizes G1 checkpoint-deficient cells to lethal premature chromatin condensation' PNAS, 2001, pp. 9092-9097, vol. 98(16).

Eric J. Brown and David Baltimore, 'Essential and dispensable roles of ATR in cell cycle arrest and genome maintenance' Genes & Development, 2003, pp. 615-628, vol. 17.
Seong Jun Park et al, 'Bioactive sulfoximines: Syntheses and properties of Vioxx analogs', Bioorganic & Medicinal Chemistry Letters, 2011, pp. 4888-4990, vol. 21.
Walker et al, 'Sulfoximine-substituted trifluoromethylpyrimidine analogs as inhibitors of proline-rich tyrosine kinase 2 (PYK2) show reduced hERG activity', Bioorganic & Medicinal Chemistry Letters, 2011, pp. 3253-3258, vol. 19.
Bartkova et al, 'DNA damage response as a candidate anti-cancer barrier in early human tumorigenesis', Nature, 2005, pp. 864-870, vol. 434 (14).
Casper et al, 'Chromosomal Instability at Common Fragile Sites in Seckel Syndrome', Am. J. Hum. Genet, 2004, pp. 654-660, vol. 75.
Gilad et al, 'Combining ATR Suppression with Oncogenic Ras Synergistically Increases Genomic Instability, Causing Synthetic Lethality or Tumorigenesis in a Dosage-Dependent Manner', Cancer Research, 2010, pp. 9693-9702, vol. 70.
Gorgoulis et al, 'Activation of the DNA damage checkpoint and genomic instability in human precancerous lesions', Nature, 2005, pp. 907-913, vol. 434.
Nuciforo et al, 'Complex engagement of DNA damage response pathways in human cancer and in lung tumor progression', Carcinogenesis, 2007, pp. 2082-2088, vol. 28.
Tort et al, 'Retinoblastoma Pathway Defects Shows Differential Ability to Activate the Constitutive DNA Damage Response in Tumorigenesis', Cancer Research, 2006, pp. 10258-10263, vol. 66.
Reaper et al, 'Selective killing of ATM- or p53-deficient cancer cells through inhibition of ATR', Nature Chemical Biology, 2011, pp. 428-430, vol. 7.
Charrier et al, 'Discovery of Potent and Selective Inhibitors of Ataxia Telangiectasia Mutated and Rad3 Related (ATR) Protein Kinase as Potential Anticancer Agents', Journal of Medicinal Chemistry, 2011, 2320-2330, 54.
Fan et al, 'ATM activation is accompanied with earlier stages of prostate tumorigenesis',Biochim Biophys Acta. Oct. 2006;1090-7. Epub Aug. 24, 2006, 1763(10).
Bartkova et al, 'DNA Damage Response Mediators MDC1 and 53BPI: Constitutive Activation and Aberrant Loss in Breast and Lung Cancer, but not in Testicular Germ Cell Tumours' Oncogene, 2007, pp. 7414-7422, vol. 26.
S.N. Suryawanshi et al 'Chemotherapy of leishmaniasis. Part VII: Synthesis and bioevaluation of substituted terpenyl pyrimidines' European Journal of Medicinal Chemistry, 2007, pp. 1211-1217 vol. 42.
Hui-Ling Wang et al, 'Novel Vanilloid Receptor-1 Antagonists: 3. The Identification of a Second-Generation Clinical Candidate with Improved Physicochemical and Pharmacokinetic Properties' Journal of Medicinal Chemistry, 2007, pp. 3528-3539 vol. 50.
David D. Davey et al, 'Design, Synthesis, and Activity of 2-Imidazol-1-ylpyrimidine Derived Inducible Nitric Oxide Synthase Dimerization Inhibitors', Journal of Medicinal Chemistry, 2007, pp. 1146-1157, vol. 50.
Bernd Dotzauer et al, '2,4-Diamino-9H-pyrimido[4,5-b]indol-5-ols: Synthesis, in vitro cytotoxic activity, and QSAR investigations'. Bioorganic & Medicinal Chemistry, 2006, pp. 7282-7292, vol. 14(21).
Sanjay Babu Katiyar et al. 'Synthesis of 2,4,6-trisubstituted pyrimidine derivatives as a new class of antifilarial topoisomerase II inhibitors', Bioorganic & Medicinal Chemistry Letters, 2005, pp. 47-50, vol. 15(1).
Naveen Chandra et al, 'Antileishmanial agents part-IV: synthesis and antileishmanial activity of novel terpenyl pyrimidines', European Journal of Medicinal Chemistry, 2005, pp. 552-556, vol. 40.
'4-Pyrimidinecarboxamide, 2,6-DI-4-Morpholinyl-N-(2-Phenylethyl)', Chemcats, 2004, XP002348927.
Roland Spitzner et al, 'Ringschlussreaktionen von 2-Acyl-1-chlorenaminen mit thioamidfunktionellen Verbindungen: Wahlweiser Zugang in die 1,3-Thiazin-und 1,3-Oxazin-Reihe', Monatshefte Fur Chemie Chemical Monthly, 1987, pp. 1383-1394, vol. 118.

(56) References Cited

OTHER PUBLICATIONS

A. Kumar et al, 'A Novel and Convenient Synthesis of 2-Amino-4-(N-alkyl-N-arylamino)-pyrimidines using Polarized Ketene S,S-and S,N-Acetals', Synthesis, 1980, pp. 748-751, vol. 9.
Richard.R. Schmidt, 'Neue Synthese von Pyrimidinderivaten', Chemische Berichte, 1965, pp. 346-351, vol. 98(2).
Minami, Shinaku et al, '2(or 6)-Nitrofurylvinyl-4-substituted aminopyrimidines XP002505932', Database Chemical Abstracts Service Columbus.
Database Registry On-Line, XP002514432, Chemical Abstracts Service Columbus, Ohio, US, Jan. 3, 2003.
Database Registry On-Line, XP002514433, Chemical Abstracts Service Columbus, Ohio, US, Jan. 3, 2003.
Database Registry On-Line, XP002514434, Chemical Abstracts Service Columbus, Ohio, US, Dec. 31, 2002.
Database Registry On-Line, XP002514435, Chemical Abstracts Service Columbus, Ohio, US, Dec. 31, 2002.
Database Registry On-Line, XP002514436, Chemical Abstracts Service Columbus, Ohio, US, Dec. 31, 2002.
Database Registry On-Line, XP002514437, Chemical Abstracts Service Columbus, Ohio, US, Dec. 31, 2002.
Database Registry On-Line, XP002514438, Chemical Abstracts Service Columbus, Ohio, US, Dec. 31, 2002.
Database Registry On-Line, XP002514439, Chemical Abstracts Service Columbus, Ohio, US, Dec. 31, 2002.
Database Registry On-Line, XP002514440, Chemical Abstracts Service Columbus, Ohio, US, Dec. 31, 2002.
Database Registry On-Line, XP002514441, Chemical Abstracts Service Columbus, Ohio, US, Jun. 4, 2001.
Database Registry On-Line, XP002514442, Chemical Abstracts Service Columbus, Ohio, US, Jun. 4, 2001.
Database Registry On-Line, XP002514443, Chemical Abstracts Service Columbus, Ohio, US, Jun. 4, 2001.
Database Registry On-Line, XP002514444, Chemical Abstracts Service Columbus, Ohio, US, Jun. 4, 2001.
Database Registry On-Line, XP002514445, Chemical Abstracts Service Columbus, Ohio, US, Jun. 4, 2001.
Database Registry On-Line, XP002514446, Chemical Abstracts Service Columbus, Ohio, US, Jun. 4, 2001.
Database Registry On-Line, XP002514447, Chemical Abstracts Service Columbus, Ohio, US, May 30, 2001.
Database Registry On-Line, XP002514448, Chemical Abstracts Service Columbus, Ohio, US, May 30, 2001.
Database Registry On-Line, XP002514449, Chemical Abstracts Service Columbus, Ohio, US, May 30, 2001.
Database Registry On-Line, XP002514450, Chemical Abstracts Service Columbus, Ohio, US, May 30, 2001.
Database Registry On-Line, XP002514451, Chemical Abstracts Service Columbus, Ohio, US, May 30, 2001.
Database Registry On-Line, XP002514452, Chemical Abstracts Service Columbus, Ohio, US, Feb. 6, 2001.
Database Registry On-Line, XP002514453, Chemical Abstracts Service Columbus, Ohio, US, Feb. 6, 2001.
Database Registry On-Line, XP002514454, Chemical Abstracts Service Columbus, Ohio, US, Dec. 6, 2000.
Database Registry On-Line, XP002514455, Chemical Abstracts Service Columbus, Ohio, US, Nov. 17, 2000.
Database Registry On-Line, XP002514456, Chemical Abstracts Service Columbus, Ohio, US, Nov. 17, 2000.
Karlene A. Cimprich & David Cortez, 'ATR: An essential regulator of genome integrity', Nature Reviews Molecular Cell Biology, 2008, pp. 616-627, vol. 9.
Nicholas D Lakin et al, 'The ataxia-telangiectasia related protein ATR mediates DNA-dependent phosphorylation of p53', Oncogene 1999, pp. 3989-3995, vol. 18.
Nicholas D Lakin et al, 'Regulation of p53 in response to DNA damage', Oncogene 1999, pp. 7644-7655, vol. 18.
Randal S Tibbetts et al, 'Functional interactions between BRCA1 and the checkpoint kinase ATR during genotoxic stress', Genes & Development, 2000, pp. 2989-3002, vol. 14(23).
Kara A. Nyberg et al, 'Toward Maintaining the Genome: DNA Damage and Replication Checkpoints', Annual Review of Genetics, 2002, pp. 617-656, vol. 36.
David Shechter et al, 'Regulation of DNA replication by ATR: signaling in response to DNA intermediates', DNA Repair, 2004, pp. 901-908, vol. 3.
Jocyndra A. Wright et al, 'Protein kinase mutants of human ATR increase sensitivity to UV and ionizing radiation and abrogate cell cycle checkpoint control', Proceedings of the National Academy of Sciences of the United States of America, 1998, pp. 7445-7450, vol. 95(23).
Mituo Ikenaga, 'Excision-Repair of 4-Nitroquinoline-1-oxide Damage Responsible for Killing, Mutation, and Cancer', Basic Life Sciences, 1975, pp. 763-771, vol. 5b.
Mark O'Driscoll et al, 'A splicing mutation affecting expression of ataxia-telangiectasia and Rad3-related protein (ATR) results in Seckel syndrome', Nature Genetics, 2003 pp. 497-501, vol. 33.
Deborah Wilsker & Fred Bunz, 'Loss of Ataxia telangiectasia mutated- and RAD3-related function potentiates the effects of chemotherapeutic drugs on cancer cell survival', Molecular Cancer Therapeutics, 2007, pp. 1406-1413, vol. 6(4).
Leslie Smith et al, 'Duplication of ATR inhibits MyoD, induces aneuploidy and eliminates radiation-induced G1 arrest', Nature Genetics, 1998, pp. 39-46, vol. 19.
David Shechter et al, 'ATR and ATM regulate the timing of DNA replication origin firing', Nature Cell Biology, 2004, pp. 648-655, vol. 6(7).
Matthew J. O'Connell & Karlene A. Cimprich, 'G2 damage checkpoints: what is the turn-on?', Journal of Cell Science, 2005, pp. 1-6, vol. 118.
Ian Collins & Michelle D Garrett, 'Targeting the cell division cycle in cancer: CDK and cell cycle checkpoint kinase inhibitors', Current Opinion in Pharmacology, 2005, pp. 366-373, vol. 5.

\* cited by examiner

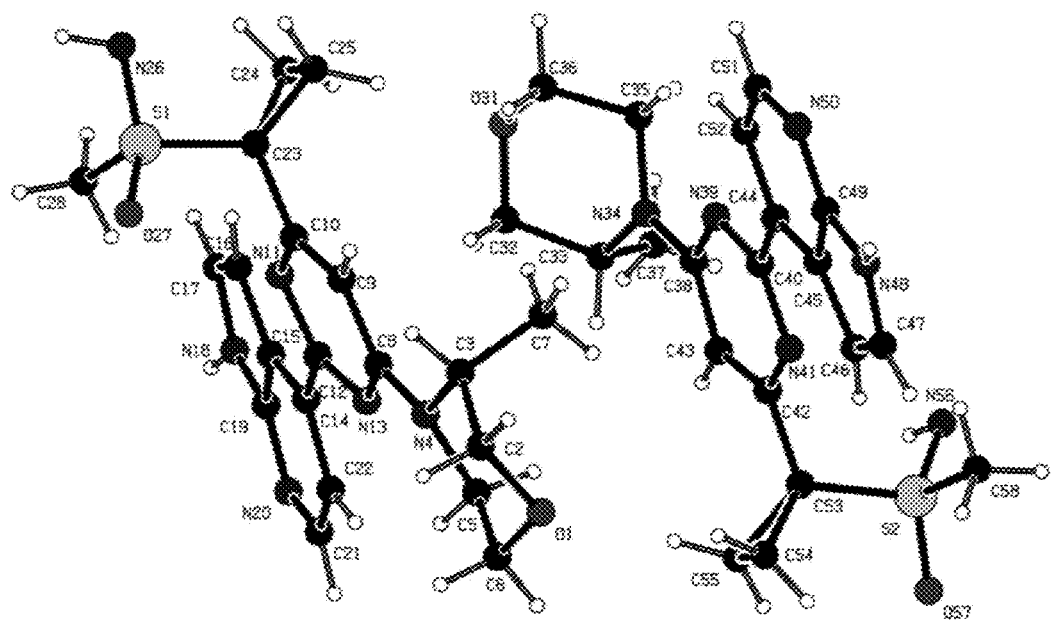

CHEMICAL COMPOUNDS

The application is a continuation of U.S. application Ser. No. 13/156,684 (now U.S. Pat. No. 8,252,802), filed Jun. 9, 2011, which claims the benefit under 35 U.S.C. §119(e) of U.S. Application No. 61/353,713, filed on Jun. 11, 2010. Each of these applications is incorporated by reference in its entirety.

The present invention relates to pyrimidinyl compounds, processes for their preparation, pharmaceutical compositions containing them and their use in therapy, for example in the treatment of proliferative disease such as cancer and particularly in disease mediated by Ataxia-telangiectasia mutated and RAD-3 related protein kinase inhibitors, commonly referred to as ATR.

ATR (also known as FRAP-Related Protein 1; FRP1; MEC1; SCKL; SECKL1) protein kinase is a member of the PI3-Kinase like kinase (PIKK) family of proteins that are involved in repair and maintenance of the genome and its stability (reviewed in Cimprich K. A. and Cortez D. 2008, Nature Rev. Mol. Cell. Biol. 9:616-627). These proteins co-ordinate response to DNA damage, stress and cell-cycle perturbation. Indeed ATM and ATR, two members of the family of proteins, share a number of downstream substrates that are themselves recognised components of the cell cycle and DNA-repair machinery e.g. Chk1, BRCA1, p53 (Lakin N D et al, 1999, Oncogene; Tibbets R S et al, 2000, Genes & Dev.). Whilst the substrates of ATM and ATR are to an extent shared, the trigger to activate the signalling cascade is not shared and ATR primarily responds to stalled replication forks (Nyberg K. A. et al., 2002, Ann. Rev. Genet. 36:617-656; Shechter D. et al. 2004, DNA Repair 3:901-908) and bulky DNA damage lesions such as those formed by ultraviolet (UV) radiation (Wright J. A. et al, 1998, Proc. Natl. Acad. Sci. USA, 23:7445-7450) or the UV mimetic agent, 4-nitroquinoline-1-oxide, 4NQO (Ikenaga M. et al. 1975, Basic Life Sci. 5b, 763-771). However, double strand breaks (DSB) detected by ATM can be processed into single strand breaks (SSB) recruiting ATR; similarly SSB, detected by ATR can generate DSB, activating ATM. There is therefore a significant interplay between ATM and ATR.

Mutations of the ATR gene that result in complete loss of expression of the ATR protein are rare and in general are not viable. Viability may only result under heterozygous or hypomorphic conditions. The only clear link between ATR gene mutations and disease exists in a few patients with Seckel syndrome which is characterized by growth retardation and microcephaly (O'Driscoll M et al, 2003 Nature Genet. Vol 3, 497-501). Cells from patients with hypomorphic germline mutations of ATR (seckel syndrome) present a greater susceptibility to chromosome breakage at fragile sites in presence of replication stress compared to wild type cells (Casper 2004). Disruption of the ATR pathway leads to genomic instability. Patients with Seckel syndrome also present an increased incidence of cancer, suggestive of the role of ATR in this disease in the maintenance of genome stability. Moreover, duplication of the ATR gene has been described as a risk factor in rhabdomyosarcomas (Smith L et al, 1998, Nature Genetics 19, 39-46). Oncogene-driven tumorigenesis may be associated with ATM loss-of-function and therefore increased reliance on ATR signalling (Gilad 2010). Evidence of replication stress has also been reported in several tumour types such as colon and ovarian cancer, and more recently in glioblastoma, bladder, prostate and breast (Gorgoulis et al., 2005; Bartkova et al. 2005a; Fan et al., 2006; Tort et al., 2006; Nuciforo et al., 2007; Bartkova et al., 2007a). Loss of G1 checkpoint is also frequently observed during tumourigenesis. Tumour cells that are deficient in G1 checkpoint controls, in particular p53 deficiency, are susceptible to inhibition of ATR activity and present with premature chromatin condensation (PCC) and cell death (Ngheim et al, PNAS, 98, 9092-9097).

ATR is essential to the viability of replicating cells and is activated during S-phase to regulate firing of replication origins and to repair damaged replication forks (Shechter D et al, 2004, Nature cell Biology Vol 6 (7) 648-655). Damage to replication forks may arise due to exposure of cells to clinically relevant cytotoxic agents such as hydroxyurea (HU) and platinums (O'Connell and Cimprich 2005; 118, 1-6). ATR is activated by most cancer chemotherapies (Wilsker D et al, 2007, Mol. Cancer. Ther. 6(4) 1406-1413). Biological assessment of the ability of ATR inhibitors to sensitise to a wide range of chemotherapies have been evaluated. Sensitisation of tumour cells to chemotherapeutic agents in cell growth assays has been noted and used to assess how well weak ATR inhibitors (such as Caffeine) will sensitise tumour cell lines to cytotoxic agents. (Wilsker D. et al, 2007, Mol Cancer Ther. 6 (4)1406-1413; Sarkaria J. N. et al, 1999, Cancer Res. 59, 4375-4382). Moreover, a reduction of ATR activity by siRNA or ATR knock-in using a dominant negative form of ATR in cancer cells has resulted in the sensitisation of tumour cells to the effects of a number of therapeutic or experimental agents such as antimetabolites (5-FU, Gemcitabine, Hydroxyurea, Metotrexate, Tomudex), alkylating agents (Cisplatin, Mitomycin C, Cyclophosphamide, MMS) or double-strand break inducers (Doxorubicin, Ionizing radiation) (Cortez D. et al. 2001, Science, 294:1713-1716; Collis S. J. et al, 2003, Cancer Res. 63:1550-1554; Cliby W. A. et al, 1998, EMBO J. 2:159-169) suggesting that the combination of ATR inhibitors with some cytotoxic agents might be therapeutically beneficial.

An additional phenotypic assay has been described to define the activity of specific ATR inhibitory compounds is the cell cycle profile (P J Hurley, D Wilsker and F Bunz, Oncogene, 2007, 26, 2535-2542). Cells deficient in ATR have been shown to have defective cell cycle regulation and distinct characteristic profiles, particularly following a cytotoxic cellular insult. Furthermore, there are proposed to be differential responses between tumour and normal tissues in response to modulation of the ATR axis and this provides further potential for therapeutic intervention by ATR inhibitor molecules (Rodriguez-Bravo V et al, Cancer Res., 2007, 67, 11648-11656).

Another compelling utility of ATR-specific phenotypes is aligned with the concept of synthetic lethality and the observation that tumour cells that are deficient in G1 checkpoint controls, in particular p53 deficiency, are susceptible to inhibition of ATR activity resulting in premature chromatin condensation (PCC) and cell death (Ngheim et al, PNAS, 98, 9092-9097). In this situation, S-phase replication of DNA occurs but is not completed prior to M-phase initiation due to failure in the intervening checkpoints resulting in cell death from a lack of ATR signalling. The G2/M checkpoint is a key regulatory control involving ATR (Brown E. J. and Baltimore D., 2003, Genes Dev. 17, 615-628) and it is the compromise of this checkpoint and the prevention of ATR signalling to its downstream partners which results in PCC. Consequently, the genome of the daughter cells is compromised and viability of the cells is lost (Ngheim et al, PNAS, 98, 9092-9097).

It has thus been proposed that inhibition of ATR may prove to be an efficacious approach to future cancer therapy (Collins I. and Garret M. D., 2005, Curr. Opin. Pharmacol., 5:366-373; Kaelin W. G. 2005, Nature Rev. Cancer, 5:689-698) in the appropriate genetic context such as tumours with defects in ATM function or other S-phase checkpoints. Until recently, There is currently no clinical precedent for agents targeting ATR, although agents targeting the downstream signalling axis i.e. Chk1 are currently undergoing clinical evaluation (reviewed in Janetka J. W. et al. Curr Opin Drug Discov Devel, 2007, 10:473-486). However, inhibitors targeting ATR kinase have recently been described (Reaper 2011, Charrier 2011).

In summary ATR inhibitors have the potential to sensitise tumour cells to ionising radiation or DNA-damage inducing chemotherapeutic agents, have the potential to induce selective tumour cell killing as well as to induce synthetic lethality in subsets of tumour cells with defects in DNA damage response.

In accordance with a first aspect of the present invention, there is provided a compound of formula (I):

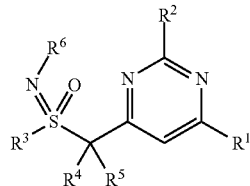

(I)

wherein:
$R^1$ is selected from morpholin-4-yl and 3-methylmorpholin-4-yl;
$R^2$ is

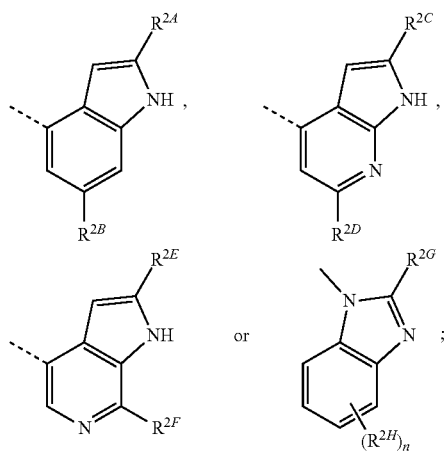

n is 0 or 1;
$R^{2A}$, $R^{2C}$, $R^{2E}$ and $R^{2F}$ each independently are hydrogen or methyl;
$R^{2B}$ and $R^{2D}$ each independently are hydrogen or methyl;
$R^{2G}$ is selected from —NHR$^7$ and —NHCOR$^8$;
$R^{2H}$ is fluoro;
$R^3$ is methyl;
$R^4$ and $R^5$ are each independently hydrogen or methyl, or $R^4$ and $R^5$ together with the atom to which they are attached form Ring A;
Ring A is a $C_{3-6}$cycloalkyl or a saturated 4-6 membered heterocyclic ring containing one heteroatom selected from O and N;
$R^6$ is hydrogen;
$R^7$ is hydrogen or methyl;
$R^8$ is methyl,
or a pharmaceutically acceptable salt thereof.

In accordance with a first aspect of the present invention, there is provided a compound of formula (I):

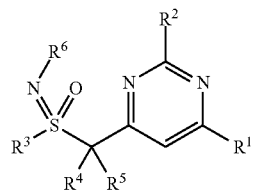

(I)

wherein:
$R^1$ is 3-methylmorpholin-4-yl;
$R^2$ is

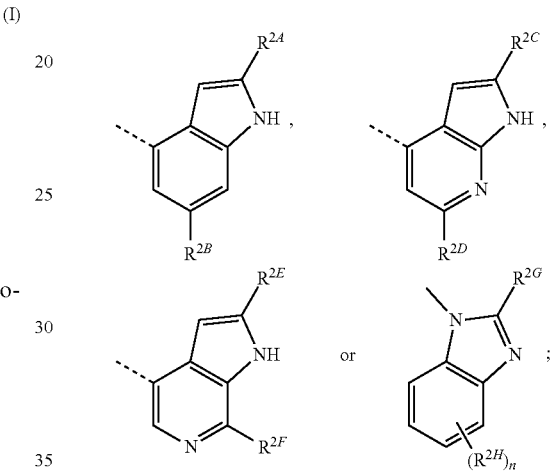

n is 0 or 1;
$R^{2A}$, $R^{2C}$, $R^{2E}$ and $R^{2F}$ each independently are hydrogen or methyl;
$R^{2B}$ and $R^{2D}$ each independently are hydrogen or methyl;
$R^{2G}$ is selected from —NH$_2$, —NHMe and —NHCOMe;
$R^{2H}$ is fluoro;
$R^3$ is methyl;
$R^4$ and $R^5$ are each independently hydrogen or methyl, or $R^4$ and $R^5$ together with the atom to which they are attached form Ring A;
Ring A is a $C_{3-6}$cycloalkyl or a saturated 4-6 membered heterocyclic ring containing one heteroatom selected from O and N; and
$R^6$ is hydrogen,
or a pharmaceutically acceptable salt thereof.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention. Solvates and mixtures thereof also form an aspect of the present invention. For example, a suitable solvate of a compound of formula (I) is, for example, a hydrate such as a hemi-hydrate, a mono-hydrate, a di-hydrate or a tri-hydrate or an alternative quantity thereof.

FIG. 1: Shows the Perspective view of the molecular structure of Example 2.02 obtained from crystals that were grown and isolated by slow evaporation to dryness in air from EtOAc. The asymmetric unit contains two crystallographically unique molecules.

It is to be understood that, insofar as certain of the compounds of formula (I) defined above may exist in optically active or racemic forms by virtue of one or more asymmetric carbon atoms or sulphur atoms, the invention includes in its definition any such optically active or racemic form which possesses the above-mentioned activity. The present invention encompasses all such stereoisomers having activity as herein defined. It is further to be understood that in the names of chiral compounds (R,S) denotes any scalemic or racemic mixture while (R) and (S) denote the enantiomers. In the absence of (R,S), (R) or (S) in the name it is to be understood that the name refers to any scalemic or racemic mixture, wherein a scalemic mixture contains R and S enantiomers in any relative proportions and a racemic mixture contains R and S enantiomers in the ratio 50:50. The synthesis of optically active forms may be carried out by standard techniques of organic chemistry well known in the art, for example by synthesis from optically active starting materials or by resolution of a racemic form. Racemates may be separated into individual enantiomers using known procedures (see, for example, Advanced Organic Chemistry: 3rd Edition: author J March, p 104-107). A suitable procedure involves formation of diastereomeric derivatives by reaction of the racemic material with a chiral auxiliary, followed by separation, for example by chromatography, of the diastereomers and then cleavage of the auxiliary species. Similarly, the above-mentioned activity may be evaluated using the standard laboratory techniques referred to hereinafter.

It will be understood that the invention encompasses compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

The present invention relates to the compounds of formula (I) as herein defined as well as to salts thereof. Salts for use in pharmaceutical compositions will be pharmaceutically acceptable salts, but other salts may be useful in the production of the compounds of formula (I) and their pharmaceutically acceptable salts. Pharmaceutically acceptable salts of the invention may, for example, include acid addition salts of compounds of formula (I) as herein defined which are sufficiently basic to form such salts. Such acid addition salts include but are not limited to fumarate, methanesulfonate, hydrochloride, hydrobromide, citrate and maleate salts and salts formed with phosphoric and sulfuric acid. In addition where compounds of formula (I) are sufficiently acidic, salts are base salts and examples include but are not limited to, an alkali metal salt for example sodium or potassium, an alkaline earth metal salt for example calcium or magnesium, or organic amine salt for example triethylamine, ethanolamine, diethanolamine, triethanolamine, morpholine, N-methylpiperidine, N-ethylpiperidine, dibenzylamine or amino acids such as lysine.

The compounds of formula (I) may also be provided as in vivo hydrolysable esters. An in vivo hydrolysable ester of a compound of formula (I) containing carboxy or hydroxy group is, for example a pharmaceutically acceptable ester which is cleaved in the human or animal body to produce the parent acid or alcohol. Such esters can be identified by administering, for example, intravenously to a test animal, the compound under test and subsequently examining the test animal's body fluid.

Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl, 1,3-dioxolen-2-onylmethyl esters for example 5-methyl-1,3-dioxolen-2-onylmethyl, and $C_{1-6}$alkoxycarbonyloxyethyl esters for example 1-methoxycarbonyloxyethyl; and may be formed at any carboxy group in the compounds of this invention.

Suitable pharmaceutically acceptable esters for hydroxy include inorganic esters such as phosphate esters (including phosphoramidic cyclic esters) and α-acyloxyalkyl ethers and related compounds which as a result of the in vivo hydrolysis of the ester breakdown to give the parent hydroxy group/s. Examples of α-acyloxyalkyl ethers include acetoxymethoxy and 2,2-dimethylpropionyloxymethoxy. A selection of in vivo hydrolysable ester forming groups for hydroxy include $C_{1-10}$alkanoyl, for example formyl, acetyl, benzoyl, phenylacetyl, substituted benzoyl and phenylacetyl; $C_{1-10}$alkoxycarbonyl (to give alkyl carbonate esters), for example ethoxycarbonyl; di-$C_{1-4}$alkylcarbamoyl and N-(di-$C_{1-4}$alkylaminoethyl)-N—$C_{1-4}$alkylcarbamoyl (to give carbamates); di-$C_{1-4}$alkylaminoacetyl and carboxyacetyl. Examples of ring substituents on phenylacetyl and benzoyl include aminomethyl, $C_{1-4}$alkylaminomethyl and di-($C_{1-4}$alkyl)aminomethyl, and morpholino or piperazino linked from a ring nitrogen atom via a methylene linking group to the 3- or 4-position of the benzoyl ring. Other interesting in vivo hydrolysable esters include, for example, $R^4C(O)OC_{1-6}$alkyl-CO—, wherein $R^4$ is for example, benzyloxy-$C_{1-4}$alkyl, or phenyl. Suitable substituents on a phenyl group in such esters include, for example, 4-$C_{1-4}$piperazino-$C_{1-4}$alkyl, piperazino-$C_{1-4}$alkyl and morpholino-$C_{1-4}$alkyl.

The compounds of the formula (I) may be also be administered in the form of a prodrug which is broken down in the human or animal body to give a compound of the formula (I). Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113-191 (1991);

c) H. Bundgaard, Advanced Drug Delivery Reviews, 8, 1-38 (1992);

d) H. Bundgaard, et al., Journal of Pharmaceutical Sciences, 77, 285 (1988); and e) N. Kakeya, et al., Chem Pharm Bull, 32, 692 (1984).

In this specification the generic term "$C_{p-q}$alkyl" includes both straight-chain and branched-chain alkyl groups. However references to individual alkyl groups such as "propyl" are specific for the straight chain version only (i.e. n-propyl and isopropyl) and references to individual branched-chain alkyl groups such as "tert-butyl" are specific for the branched chain version only.

The prefix $C_{p-q}$ in $C_{p-q}$alkyl and other terms (where p and q are integers) indicates the range of carbon atoms that are present in the group, for example $C_{1-4}$alkyl includes $C_1$alkyl (methyl), $C_1$alkyl (ethyl), $C_1$alkyl (propyl as n-propyl and isopropyl) and $C_1$alkyl (n-butyl, sec-butyl, isobutyl and tert-butyl).

The term $C_{p-q}$alkoxy comprises —O—$C_{p-q}$alkyl groups.
The term $C_{p-q}$alkanoyl comprises —C(O)alkyl groups.
The term halo includes fluoro, chloro, bromo and iodo.

"Carbocyclyl" is a saturated, unsaturated or partially saturated monocyclic ring system containing from 3 to 6 ring atoms, wherein a ring $CH_2$ group may be replaced with a C=O group. "Carbocyclyl" includes "aryl", "$C_{p-q}$cycloalkyl" and "$C_{p-q}$cycloalkenyl".

"aryl" is an aromatic monocyclic carbocyclyl ring system.

"$C_{p-q}$cycloalkenyl" is an unsaturated or partially saturated monocyclic carbocyclyl ring system containing at least 1 C=C bond and wherein a ring $CH_2$ group may be replaced with a C=O group.

"$C_{p-q}$cycloalkyl" is a saturated monocyclic carbocyclyl ring system and wherein a ring $CH_2$ group may be replaced with a C=O group.

"Heterocyclyl" is a saturated, unsaturated or partially saturated monocyclic ring system containing from 3 to 6 ring atoms of which 1, 2 or 3 ring atoms are chosen from nitrogen, sulfur or oxygen, which ring may be carbon or nitrogen linked and wherein a ring nitrogen or sulfur atom may be oxidised and wherein a ring $CH_2$ group may be replaced with a C=O group. "Heterocyclyl" includes "heteroaryl", "cycloheteroalkyl" and "cycloheteroalkenyl".

"Heteroaryl" is an aromatic monocyclic heterocyclyl, particularly having 5 or 6 ring atoms, of which 1, 2 or 3 ring atoms are chosen from nitrogen, sulfur or oxygen where a ring nitrogen or sulfur may be oxidised.

"Cycloheteroalkenyl" is an unsaturated or partially saturated monocyclic heterocyclyl ring system, particularly having 5 or 6 ring atoms, of which 1, 2 or 3 ring atoms are chosen from nitrogen, sulfur or oxygen, which ring may be carbon or nitrogen linked and wherein a ring nitrogen or sulfur atom may be oxidised and wherein a ring $CH_2$ group may be replaced with a C=O group.

"Cycloheteroalkyl" is a saturated monocyclic heterocyclic ring system, particularly having 5 or 6 ring atoms, of which 1, 2 or 3 ring atoms are chosen from nitrogen, sulfur or oxygen, which ring may be carbon or nitrogen linked and wherein a ring nitrogen or sulfur atom may be oxidised and wherein a ring $CH_2$ group may be replaced with a C=O group.

This specification may make use of composite terms to describe groups comprising more than one functionality. Unless otherwise described herein, such terms are to be interpreted as is understood in the art. For example carbocyclyl$C_{p-q}$alkyl comprises $C_{p-q}$alkyl substituted by carbocyclyl, heterocyclyl$C_{p-q}$alkyl comprises $C_{p-q}$alkyl substituted by heterocyclyl, and bis($C_{p-q}$alkyl)amino comprises amino substituted by 2 $C_{p-q}$alkyl groups which may be the same or different.

Halo$C_{p-q}$alkyl is a $C_{p-q}$alkyl group that is substituted by 1 or more halo substituents and particularly 1, 2 or 3 halo substituents. Similarly, other generic terms containing halo such as halo$C_{p-q}$alkoxy may contain 1 or more halo substituents and particularly 1, 2 or 3 halo substituents.

Hydroxy$C_{p-q}$alkyl is a $C_{p-q}$alkyl group that is substituted by 1 or more hydroxyl substituents and particularly by 1, 2 or 3 hydroxy substituents. Similarly other generic terms containing hydroxy such as hydroxy$C_{p-q}$alkoxy may contain 1 or more and particularly 1, 2 or 3 hydroxy substituents.

$C_{p-q}$alkoxy$C_{p-q}$alkyl is a $C_{p-q}$alkyl group that is substituted by 1 or more $C_{p-q}$alkoxy substituents and particularly 1, 2 or 3 $C_{p-q}$alkoxy substituents. Similarly other generic terms containing $C_{p-q}$alkoxy such as $C_{p-q}$alkoxy$C_{p-q}$alkoxy may contain 1 or more $C_{p-q}$alkoxy substituents and particularly 1, 2 or 3 $C_{p-q}$alkoxy substituents.

Where optional substituents are chosen from "1 or 2", from "1, 2, or 3" or from "1, 2, 3 or 4" groups or substituents it is to be understood that this definition includes all substituents being chosen from one of the specified groups i.e. all substitutents being the same or the substituents being chosen from two or more of the specified groups i.e. the substitutents not being the same.

Compounds of the present invention have been named with the aid of computer software (ACD/Name version 10.06).

"Proliferative disease(s)" includes malignant disease(s) such as cancer as well as non-malignant disease(s) such as inflammatory diseases, obstractive airways diseases, immune diseases or cardiovascular diseases.

Suitable values for any R group or any part or substitutent for such groups include:

| | |
|---|---|
| for $C_{1-3}$alkyl: | methyl, ethyl, propyl and iso-propyl; |
| for $C_{1-6}$alkyl: | $C_{1-3}$alkyl, butyl, 2-methylpropyl, tent-butyl, pentyl, 2,2-dimethylpropyl, 3-methylbutyl and hexyl; |
| for $C_{3-6}$cycloalkyl: | cyclopropyl, cyclobutyl, cyclopentyl and cyclohexyl; |
| for $C_{3-6}$cycloalkyl$C_{1-3}$alkyl: | cyclopropylmethyl, cyclopropylethyl, cyclobutylmethyl, cyclopentylmethyl and cyclohexylmethyl; |
| for aryl: | phenyl; |
| for aryl$C_{1-3}$alkyl: | benzyl and phenethyl; |
| for carbocylyl: | aryl, cyclohexenyl and $C_{3-6}$cycloalkyl; |
| for halo: | fluoro, chloro, bromo and iodo; |
| for $C_{1-3}$alkoxy: | methoxy, ethoxy, propoxy and isopropoxy; |
| for $C_{1-6}$alkoxy: | $C_{1-3}$alkoxy, butoxy, tent-butoxy, pentyloxy, 1-ethylpropoxy and hexyloxy; |
| for $C_{1-3}$alkanoyl: | acetyl and propanoyl; |
| for $C_{1-6}$alkanoyl: | acetyl, propanoyl and 2-methylpropanoyl; |
| for heteroaryl: | pyridinyl, imidazolyl, pyrimidinyl, thienyl, pyrrolyl, pyrazolyl, thiazolyl, thiazolyl, triazolyl, oxazolyl, isoxazolyl, furanyl, pyridazinyl and pyrazinyl; |
| for heteroaryl$C_{1-3}$alkyl: | pyrrolylmethyl, pyrrolylethyl, imidazolylmethyl, imidazolylethyl, pyrazolylmethyl, pyrazolylethyl, furanylmethyl, furanylethyl, thienylmethyl, theinylethyl, pyridinylmethyl, pyridinylethyl, pyrazinylmethyl, pyrazinylethyl, pyrimidinylmethyl, pyrimidinylethyl, pyrimidinylpropyl, pyrimidinylbutyl, imidazolylpropyl, imidazolylbutyl, 1,3,4-triazolylpropyl and oxazolylmethyl; |
| for heterocyclyl: | heteroaryl, pyrrolidinyl, piperidinyl, piperazinyl, azetidinyl, morpholinyl, dihydro-2H-pyranyl, tetrahydropyridine and tetrahydrofuranyl; |
| for saturared heterocyclyl: | oxetanyl, pyrrolidinyl, piperidinyl, piperazinyl, azetidinyl, morpholinyl, tetrahydropyranyl and tetrahydrofuranyl. |

It should be noted that examples given for terms used in the description are not limiting.

Particular values of Ring A, n, $R^1$, $R^2$, $R^4$, $R^5$, $R^6$, $R^7$ and $R^8$ are as follows. Such values may be used individually or in combination where appropriate, in connection with any aspect of the invention, or part thereof, and with any of the definitions, claims or embodiments defined herein.

n

In one aspect n is 0.

In another aspect n is 1.

$R^1$

In one aspect, $R^1$ is selected from morpholin-4-yl and 3-methylmorpholin-4-yl.

In a further aspect, $R^1$ is 3-methylmorpholin-4-yl.

In a further aspect, $R^1$ is

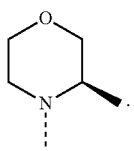

In a further aspect, $R^1$ is

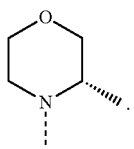

$R^2$

In one aspect $R^2$ is

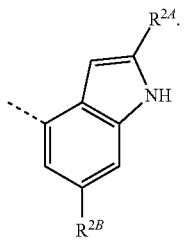

In one aspect $R^2$ is

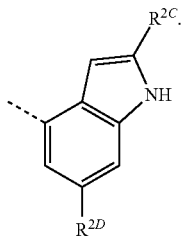

In one aspect $R^2$ is

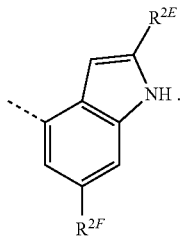

In one aspect $R^2$ is

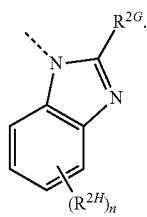

$R^{2A}$ $R^{2A}$ is hydrogen.

$R^{2B}$ $R^{2B}$ is hydrogen.

$R^{2C}$ $R^{2C}$ is hydrogen.

$R^{2D}$ $R^{2D}$ is hydrogen.

$R^{2E}$ $R^{2E}$ is hydrogen.

$R^{2F}$ $R^{2F}$ is hydrogen.

$R^{2G}$

In one aspect of the invention $R^{2G}$ is selected from —$NHR^7$ and —$NHCOR^8$.

In one aspect of the invention $R^{2G}$ is —$NHR^7$.

In one aspect of the invention $R^{2G}$ is —$NHCOR^8$.

In one aspect of the invention $R^{2G}$ is selected from —$NH_2$, —NHMe and —NHCOMe.

In one aspect of the invention $R^{2G}$ is —$NH_2$.

In one aspect of the invention $R^{2G}$ is —NHMe.

In one aspect of the invention $R^{2G}$ is —NHCOMe.

$R^4$ and $R^5$

In one aspect of the invention $R^4$ and $R^5$ are hydrogen.

In one aspect of the invention $R^4$ and $R^5$ are methyl.

In one aspect of the invention $R^4$ and $R^5$ together with the atom to which they are attached form Ring A.

Ring A

In one aspect of the invention Ring A is a $C_{3-6}$cycloalkyl or a saturated 4-6 heterocyclic ring containing one heteroatom selected from O and N In another aspect Ring A is a cyclopropyl, cyclobutyl, cyclopentyl, oxetanyl, tetrahydrofuryl, tetrahydropyranyl, azetidinyl, pyrrolidinyl or piperidinyl ring.

In another aspect Ring A is a cyclopropyl, cyclobutyl, cyclopentyl, tetrahydropyranyl or piperidinyl ring.

In another aspect Ring A is a cyclopropyl, cyclopentyl, tetrahydropyranyl or piperidinyl ring.

In another aspect Ring A is a cyclopropyl, tetrahydropyranyl or piperidinyl ring.

In another aspect Ring A is a cyclopropyl or tetrahydropyranyl ring.

In another aspect Ring A is a piperidinyl ring.

In another aspect Ring A is a tetrahydropyranyl ring.

In another aspect Ring A is a cyclopropyl ring.

$R^6$

In one aspect $R^6$ is hydrogen.

$R^7$

In one aspect $R^7$ is hydrogen or methyl.

In one aspect $R^7$ is methyl.

In one aspect $R^7$ is hydrogen.

$R^8$

In one aspect $R^{12}$ is methyl.

In one aspect of the invention there is provided a subset of compounds of formula (I), or a pharmaceutically acceptable salt thereof;

R$^1$ is selected from morpholin-4-yl and 3-methylmorpholin-4-yl;
n is 0 or 1;
R$^{2A}$ is hydrogen;
R$^{2B}$ is hydrogen;
R$^{2C}$ is hydrogen;
R$^{2D}$ is hydrogen;
R$^{2E}$ is hydrogen;
R$^{2F}$ is hydrogen;
R$^{2G}$ is selected from —NHR$^7$ and —NHCOR$^8$;
R$^{2H}$ is fluoro;
R$^3$ is methyl;
R$^4$ and R$^5$ together with the atom to which they are attached form Ring A;
Ring A is a C$_{3-6}$cycloalkyl or a saturated 4-6 heterocyclic ring containing one heteroatom selected from O and N;
R$^6$ is hydrogen;
R$^7$ is hydrogen or methyl; and
R$^8$ is methyl.

In another aspect of the invention there is provided a subset of compounds of formula (I), or a pharmaceutically acceptable salt thereof;
R$^1$ is selected from morpholin-4-yl and 3-methylmorpholin-4-yl;
n is 0 or 1;
R$^{2A}$ is hydrogen;
R$^{2B}$ is hydrogen;
R$^{2C}$ is hydrogen;
R$^{2D}$ is hydrogen;
R$^{2E}$ is hydrogen;
R$^{2F}$ is hydrogen;
R$^{2G}$ is selected from —NH$_2$, —NHMe and —NHCOMe;
R$^{2H}$ is fluoro;
R$^3$ is methyl;
R$^4$ and R$^5$ together with the atom to which they are attached form Ring A;
Ring A is a C$_{3-6}$cycloalkyl or a saturated 4-6 heterocyclic ring containing one heteroatom selected from O and N; and
R$^6$ is hydrogen.

In another aspect of the invention there is provided a subset of compounds of formula (I), or a pharmaceutically acceptable salt thereof;
R$^1$ is selected from morpholin-4-yl and 3-methylmorpholin-4-yl;
n is 0 or 1;
R$^{2A}$ is hydrogen;
R$^{2B}$ is hydrogen;
R$^{2C}$ is hydrogen;
R$^{2D}$ is hydrogen;
R$^{2E}$ is hydrogen;
R$^{2F}$ is hydrogen;
R$^{2G}$ is selected from —NHR$^7$ and —NHCOR$^8$;
R$^{2H}$ is fluoro;
R$^3$ is methyl;
R$^4$ and R$^5$ together with the atom to which they are attached form Ring A;
Ring A is a cyclopropyl, cyclobutyl, cyclopentyl, oxetanyl, tetrahydrofuryl, tetrahydropyranyl, azetidinyl, pyrrolidinyl or piperidinyl ring;
R$^6$ is hydrogen;
R$^7$ is hydrogen or methyl; and
R$^8$ is methyl.

In another aspect of the invention there is provided a subset of compounds of formula (I), or a pharmaceutically acceptable salt thereof;
R$^1$ is selected from morpholin-4-yl and 3-methylmorpholin-4-yl;
n is 0 or 1;
R$^{2A}$ is hydrogen;
R$^{2B}$ is hydrogen;
R$^{2C}$ is hydrogen;
R$^{2D}$ is hydrogen;
R$^{2E}$ is hydrogen;
R$^{2F}$ is hydrogen;
R$^{2G}$ is selected from —NH$_2$, —NHMe and —NHCOMe;
R$^{2H}$ is fluoro;
R$^3$ is methyl;
R$^4$ and R$^5$ together with the atom to which they are attached form Ring A;
Ring A is a cyclopropyl, cyclobutyl, cyclopentyl, oxetanyl, tetrahydrofuryl, tetrahydropyranyl, azetidinyl, pyrrolidinyl or piperidinyl ring; and
R$^6$ is hydrogen.

In another aspect of the invention there is provided a subset of compounds of formula (Ia),

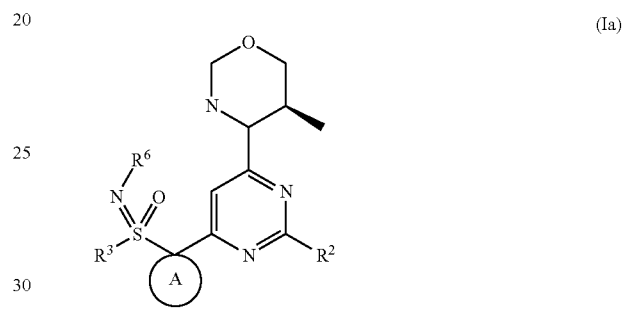

(Ia)

or a pharmaceutically acceptable salt thereof;
Ring A is a cyclopropyl, tetrahydropyranyl or piperidinyl ring;
R$^2$ is

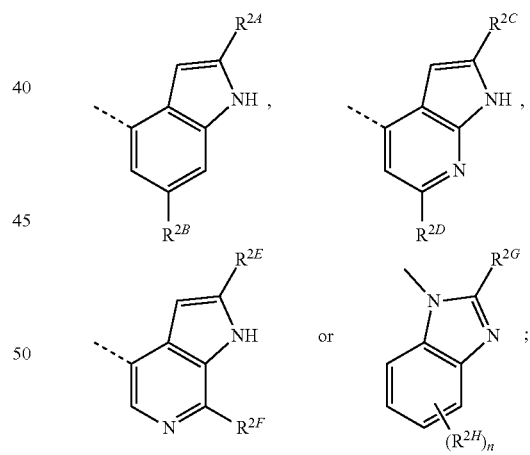

n is 0 or 1;
R$^{2A}$ is hydrogen;
R$^{2B}$ is hydrogen;
R$^{2C}$ is hydrogen;
R$^{2D}$ is hydrogen;
R$^{2E}$ is hydrogen;
R$^{2F}$ is hydrogen;
R$^{2G}$ is selected from —NHR$^7$ and —NHCOR$^8$;
R$^{2H}$ is fluoro;
R$^3$ is a methyl group;
R$^6$ is hydrogen;
R$^7$ is hydrogen or methyl; and
R$^8$ is methyl.

In another aspect of the invention there is provided a subset of compounds of formula (Ia),

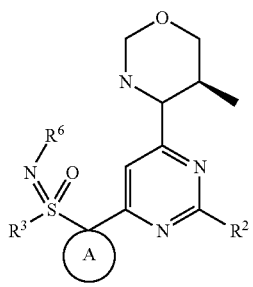
(Ia)

or a pharmaceutically acceptable salt thereof;
Ring A is a cyclopropyl, tetrahydropyranyl or piperidinyl ring;
$R^2$ is

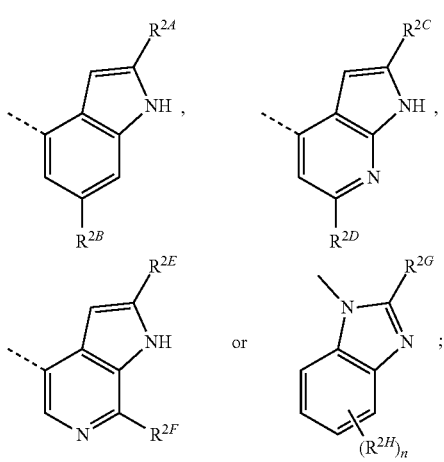

n is 0 or 1;
$R^{2A}$ is hydrogen;
$R^{2B}$ is hydrogen;
$R^{2C}$ is hydrogen;
$R^{2D}$ is hydrogen;
$R^{2E}$ is hydrogen;
$R^{2F}$ is hydrogen;
$R^{2G}$ is selected from —NH$_2$, —NHMe and —NHCOMe;
$R^{2H}$ is fluoro;
$R^3$ is a methyl group; and
$R^6$ is hydrogen.

In another aspect of the invention there is provided a subset of compounds of formula (Ia),

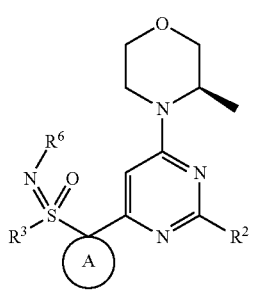
(Ia)

or a pharmaceutically acceptable salt thereof;

Ring A is a cyclopropyl, tetrahydropyranyl or piperidinyl ring;
$R^2$ is

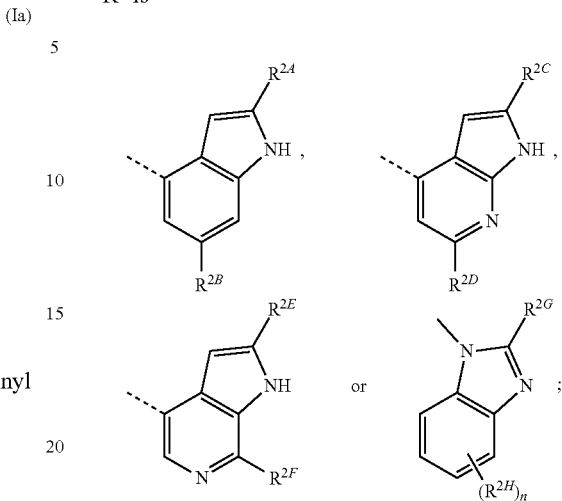

n is 0 or 1;
$R^{2A}$ is hydrogen;
$R^{2B}$ is hydrogen;
$R^{2C}$ is hydrogen;
$R^{2D}$ is hydrogen;
$R^{2E}$ is hydrogen;
$R^{2F}$ is hydrogen;
$R^{2G}$ is —NHR$^7$;
$R^{2H}$ is fluoro;
$R^3$ is a methyl group;
$R^6$ is hydrogen; and
$R^7$ is hydrogen.

In another aspect of the invention there is provided a subset of compounds of formula (Ia),

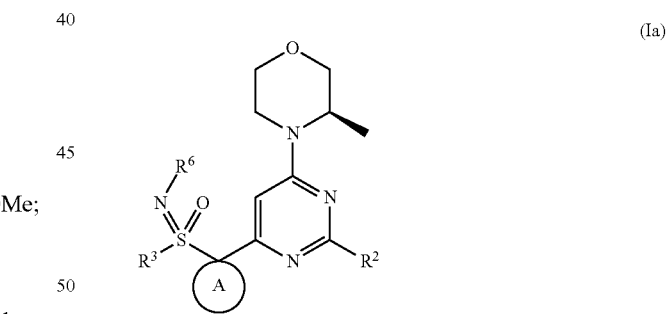
(Ia)

or a pharmaceutically acceptable salt thereof;
Ring A is a cyclopropyl ring;
$R^2$ is

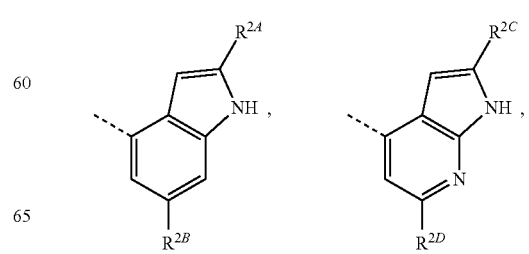

-continued

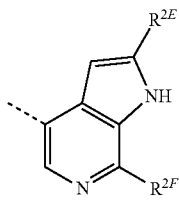 or 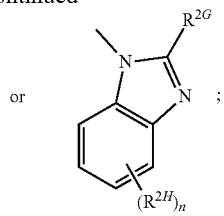

n is 0;
$R^{2A}$ is hydrogen;
$R^{2B}$ is hydrogen;
$R^{2C}$ is hydrogen;
$R^{2D}$ is hydrogen;
$R^{2E}$ is hydrogen;
$R^{2F}$ is hydrogen;
$R^{2G}$ is —$NHR^7$;
$R^{2H}$ is fluoro;
$R^3$ is a methyl group;
$R^6$ is hydrogen; and
$R^7$ is methyl.

In another aspect of the invention provides a compound, or a combination of compounds, selected from any one of the Examples or a pharmaceutically acceptable salt thereof.

In another aspect of the invention there is provided a compound, or a combination of compounds, selected from any one of 4-{4-[(3R)-3-Methylmorpholin-4-yl]-6-[((R)—S-methylsulfonimidoyl)methyl]pyrimidin-2-yl}-1H-pyrrolo[2,3-b]pyridine;
4-{4-[(3R)-3-Methylmorpholin-4-yl]-6-[1-((S)—S-methylsulfonimidoyl)cyclopropyl]pyrimidin-2-yl}-1H-pyrrolo[2,3-b]pyridine;
4-{4-[(3R)-3-Methylmorpholin-4-yl]-6-[1-((R)—S-methylsulfonimidoyl)cyclopropyl]pyrimidin-2-yl}-1H-pyrrolo[2,3-b]pyridine;
N-Methyl-1-{4-[(3R)-3-methylmorpholin-4-yl]-6-[1-((R)—S-methylsulfonimidoyl)cyclopropyl]pyrimidin-2-yl}-1H-benzimidazol-2-amine;
N-Methyl-1-{4-[(3R)-3-methylmorpholin-4-yl]-6-[1-((S)—S-methylsulfonimidoyl)cyclopropyl]pyrimidin-2-yl}-1H-benzimidazol-2-amine;
4-{4-[(3R)-3-Methylmorpholin-4-yl]-6-[1-((R)—S-methylsulfonimidoyl)cyclopropyl]pyrimidin-2-yl}-1H-indole;
4-{4-[(3R)-3-methylmorpholin-4-yl]-6-[1-((S)—S-methylsulfonimidoyl)cyclopropyl]pyrimidin-2-yl}-1H-indole;
1-{4-[(3R)-3-Methylmorpholin-4-yl]-6-[1-((R)—S-methylsulfonimidoyl)cyclopropyl]pyrimidin-2-yl}-1H-benzimidazol-2-amine;
1-{4-[(3R)-3-methylmorpholin-4-yl]-6-[1-((S)—S-methylsulfonimidoyl)cyclopropyl]pyrimidin-2-yl}-1H-benzimidazol-2-amine;
4-Fluoro-N-methyl-1-{4-[(3R)-3-methylmorpholin-4-yl]-6-[1-((R)—S-methylsulfonimidoyl)cyclopropyl]pyrimidin-2-yl}-1H-benzimidazol-2-amine;
4-fluoro-N-methyl-1-{4-[(3R)-3-methylmorpholin-4-yl]-6-[1-((S)—S-methylsulfonimidoyl)cyclopropyl]pyrimidin-2-yl}-1H-benzimidazol-2-amine;
4-{4-[(3R)-3-Methylmorpholin-4-yl]-6-[1-(S-methylsulfonimidoyl)cyclopropyl]pyrimidin-2-yl}-1H-pyrrolo[2,3-c]pyridine;
N-methyl-1-{4-[1-methyl-1-((S)—S-methylsulfonimidoyl)ethyl]-6-[(3R)-3-methylmorpholin-4-yl]pyrimidin-2-yl}-1H-benzimidazol-2-amine;
N-methyl-1-{4-[1-methyl-1-((R)—S-methylsulfonimidoyl)ethyl]-6-[(3R)-3-methylmorpholin-4-yl]pyrimidin-2-yl}-1H-benzimidazol-2-amine;
N-Methyl-1-{4-[(3R)-3-methylmorpholin-4-yl]-6-[4-(S)—S-methylsulfonimidoyl)tetrahydro-2H-pyran-4-yl]pyrimidin-2-yl}-1H-benzimidazol-2-amine;
N-methyl-1-{4-[(3R)-3-methylmorpholin-4-yl]-6-[4-(R)—S-methylsulfonimidoyl)tetrahydro-2H-pyran-4-yl]pyrimidin-2-yl}-1H-benzimidazol-2-amine;
4-{4-[(3R)-3-Methylmorpholin-4-yl]-6-[4-((S)—S-methylsulfonimidoyl)tetrahydro-2H-pyran-4-yl]pyrimidin-2-yl}-1H-indole;
4-Fluoro-N-methyl-1-{4-[1-methyl-1-((S)—S-methylsulfonimidoyl)ethyl]-6-[(3R)-3-methylmorpholin-4-yl]pyrimidin-2-yl}-1H-benzimidazol-2-amine;
4-fluoro-N-methyl-1-{4-[1-methyl-1-((R)—S-methylsulfonimidoyl)ethyl]-6-[(3R)-3-methylmorpholin-4-yl]pyrimidin-2-yl}-1H-benzimidazol-2-amine;
6-Fluoro-N-methyl-1-{4-[1-methyl-1-((R)—S-methylsulfonimidoyl)ethyl]-6-[(3R)-3-methylmorpholin-4-yl]pyrimidin-2-yl}-1H-benzimidazol-2-amine;
5-Fluoro-N-methyl-1-{4-[1-methyl-1-((R)—S-methylsulfonimidoyl)ethyl]-6-[(3R)-3-methylmorpholin-4-yl]pyrimidin-2-yl}-1H-benzimidazol-2-amine;
5-Fluoro-N-methyl-1-{4-[1-methyl-1-((S)—S-methylsulfonimidoyl)ethyl]-6-[(3R)-3-methylmorpholin-4-yl]pyrimidin-2-yl}-1H-benzimidazol-2-amine;
6-fluoro-N-methyl-1-{4-[1-methyl-1-((S)—S-methylsulfonimidoyl)ethyl]-6-[(3R)-3-methylmorpholin-4-yl]pyrimidin-2-yl}-1H-benzimidazol-2-amine;
6-Fluoro-N-methyl-1-{4-[(3R)-3-methylmorpholin-4-yl]-6-[1-((R)—S-methylsulfonimidoyl)cyclopropyl]pyrimidin-2-yl}-1H-benzimidazol-2-amine;
5-fluoro-N-methyl-1-{4-[(3R)-3-methylmorpholin-4-yl]-6-[1-((R)—S-methylsulfonimidoyl)cyclopropyl]pyrimidin-2-yl}-1H-benzimidazol-2-amine;
5-fluoro-N-methyl-1-{4-[(3R)-3-methylmorpholin-4-yl]-6-[1-((S)—S-methylsulfonimidoyl)cyclopropyl]pyrimidin-2-yl}-1H-benzimidazol-2-amine; and
6-fluoro-N-methyl-1-{4-[(3R)-3-methylmorpholin-4-yl]-6-[1-((S)—S-methylsulfonimidoyl)cyclopropyl]pyrimidin-2-yl}-1H-benzimidazol-2-amine, or a pharmaceutically acceptable salt thereof.

In another aspect of the invention there is provided a compound, or a combination of compounds, selected from any one of 4-{4-[(3R)-3-methylmorpholin-4-yl]-6-[(R)—(S-methylsulfonimidoyl)methyl]pyrimidin-2-yl}-1H-pyrrolo[2,3-b]pyridine;
4-{4-[(3R)-3-methylmorpholin-4-yl]-6-[1-((S)—S-methylsulfonimidoyl)cyclopropyl]pyrimidin-2-yl}-1H-pyrrolo[2,3-b]pyridine;
4-{4-[(3R)-3-methylmorpholin-4-yl]-6-[1-((R)—S-methylsulfonimidoyl)cyclopropyl]pyrimidin-2-yl}-1H-pyrrolo[2,3-b]pyridine;
N-methyl-1-{4-[(3R)-3-methylmorpholin-4-yl]-6-[1-(R)—(S-methylsulfonimidoyl)cyclopropyl]pyrimidin-2-yl}-1H-benzimidazol-2-amine; and
N-methyl-1-{4-[(3R)-3-methylmorpholin-4-yl]-6-[1-(S)—(S—methylsulfonimidoyl)cyclopropyl]pyrimidin-2-yl}-1H-benzimidazol-2-amine, or a pharmaceutically acceptable salt thereof.

A compound of formula (I) may be prepared from a compound of formula (II), wherein $L^2$ is a leaving group (such as halo or —SMe, etc.), by reaction with a compound of formula (IIIa), (IIIb) or (Inc), wherein X is a suitable group (such as boronic acid or ester) in the presence of a suitable Pd catalyst and phosphine ligand in a suitable solvent such as a mixture of N,N-dimethylformamide, dimethoxyethane, water and ethanol, under suitable conditions such as heating in a microwave reactor. Alternatively, a compound of formula (I) may be prepared from a compound of formula (II), wherein $L^2$ is a leaving group (such as halo or —SMe, etc.), by reaction with a compound of formula (IIId), with a suitable base such as NaH, $Na_2CO_3$, $Cs_2CO_3$ or $K_2CO_3$ in a suitable solvent such as N,N-dimethylformamide or N,N-dimethylacetamide or in the presence of a suitable Pd catalyst and phosphine ligand in a suitable solvent such as dioxane.

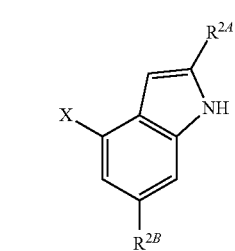
(IIIa)

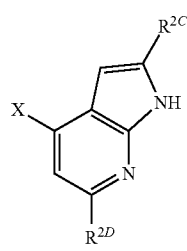
(IIIb)

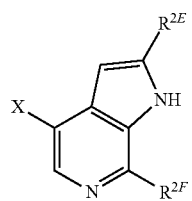
(IIIc)

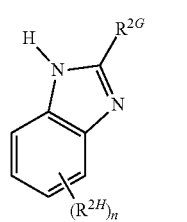
(IIId)

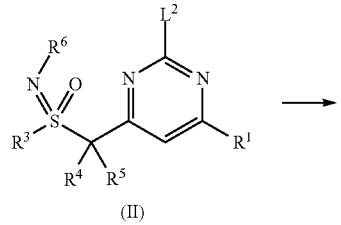
(II)

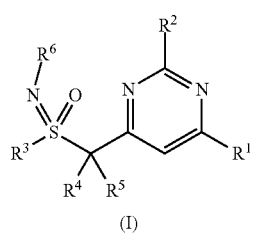
(I)

It will be appreciated that a compound of formula (I) may be transformed into another compound of formula (I) using conditions well known in the art.

Compounds of formula (IIIa), (IIIb), (IIIc) and (IIId) are either commercially available or well known in the art.

It will be appreciated that a compound of formula (II) may be transformed into another compound of formula (II) by techniques such as oxidation, alkylation, reductive amination etc., either listed above or otherwise known in the literature.

A compound of formula (II) where $R^6$ is hydrogen and $R^4$ and $R^5$ form Ring A, may be prepared by the reaction of a compound of formula (IV), wherein PG is a suitable protecting group such as trifluoroacetamide, with a compound of formula (V), wherein A is a 2 to 6 membered, optionally substituted, alkylene chain in which 1 carbon may be optionally replaced with O, N or S, and wherein $L^1$ is a leaving group (such as halo, tosyl, mesyl etc.), and removal of the protecting group in the presence of a suitable base such as sodium hydride or potassium tert-butoxide in a suitable solvent such as tetrahydrofuran or N,N-dimethylformamide, or by using aqueous sodium hydroxide solution and a suitable solvent such as DCM or toluene with a suitable phase transfer agent such as tetrabutylammonium bromide.

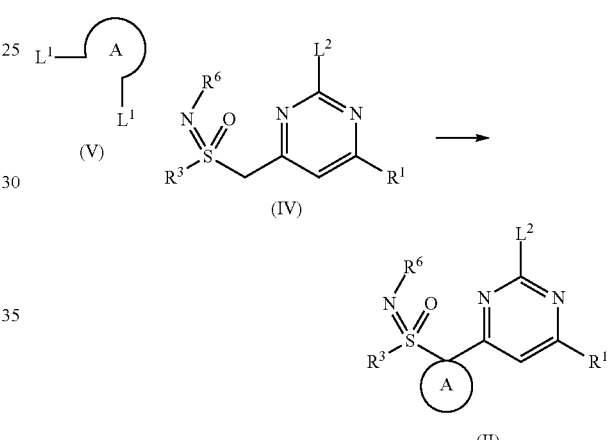

A compound of formula (II) $R^6$ is hydrogen and $R^4$ and $R^5$ are both methyl, may be prepared by the reaction of a compound of formula (IV), wherein PG is a suitable protecting group such as trifluoroacetamide, with a compound of formula (Va), wherein $L^1$ is a leaving group (such as halo, tosyl, mesyl etc.), and removal of the protecting group in the presence of a suitable base such as sodium hydride or potassium tert-butoxide in a suitable solvent such as tetrahydrofuran or N,N-dimethylformamide.

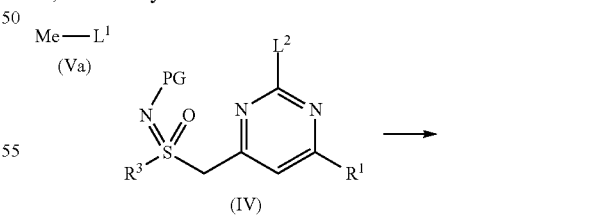

A compound of formula (IV) where PG is a suitable protecting group such as trifluoroacetamide, may be prepared by the reaction of a compound of formula (VI) with the iminoiodane (V10) which can be prepared in situ from iodobenzene diacetate and trifluoroacetamide in a suitable solvent such as DCM in the presence of a suitable base such as magnesium oxide and a catalyst such as rhodium acetate.

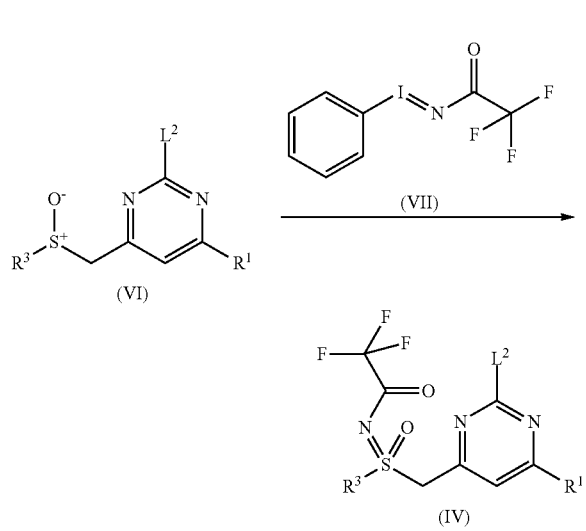

A compound of formula (I), where $R^4$, $R^5$ and $R^6$ are hydrogen, may be prepared by reaction of a compound of formula (IV), wherein $L^2$ is a leaving group (such as halo or —SMe, etc.), with a compound of formula (IIIa), (Mb) or (Mc), wherein X is a suitable group (such as boronic acid or ester) in the presence of a suitable Pd catalyst and phosphine ligand in a suitable solvent such as a mixture of N,N-dimethylformamide, dimethoxyethane, water and ethanol, under suitable conditions such as heating in a microwave reactor and removal of the trifluoroacetamide protecting group. Alternatively, a compound of formula (I), where $R^4$, $R^5$ and $R^6$ are hydrogen, may be prepared by reaction of a compound of formula (IV), wherein $L^2$ is a leaving group (such as halo or —SMe, etc.), with a compound of formula (IIId), with a suitable base such as NaH, $Na_2CO_3$, $Cs_2CO_3$ or $K_2CO_3$ in a suitable solvent such as N,N-dimethylformamide or N,N-dimethylacetamide or in the presence of a suitable Pd catalyst and phosphine ligand in a suitable solvent such as dioxane and removal of the trifluoroacetamide.

A compound of formula (VI), may be prepared by the reaction of a compound of formula (VIII) using conditions well known in the art.

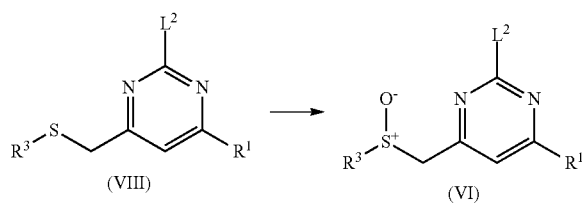

A compound of formula (VIII), may be prepared by the reaction of a compound of formula (IX), wherein $L^4$ is a leaving group (such as halo, tosyl, mesyl etc), with a compound of formula (X) optionally in the presence of a suitable base such as triethylamine and a solvent such as N,N-dimethylformamide.

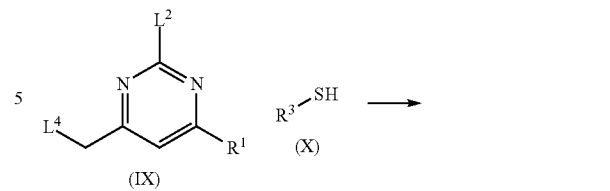

A compound of formula (IX), may be prepared by the reaction of a compound of formula (XI) using conditions well known in the art.

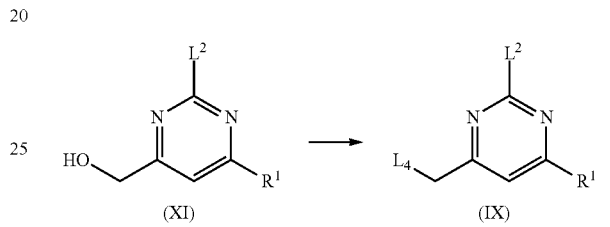

A compound of formula (XI), may be prepared by the reaction of a compound of formula (XII) using conditions well known in the art.

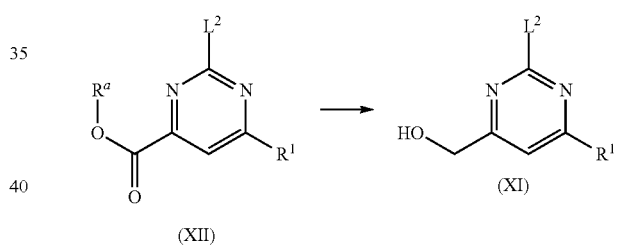

A compound of formula (XII), where $R^1$ is a N-linked heterocycle such as morpholine, may be prepared by the reaction of a compound of formula (XIII) with a cyclic amine such as morpholine optionally in the presence of a suitable base such as triethylamine in a suitable solvent such as DCM. A compound of formula (XII), where $R^1$ is a C-linked heterocycle such as dihydropyran, may be prepared by the reaction of a compound of formula (XIII) with a suitable organometallic reagent (such as the boronic acid $R^1B(OH)_2$ or the boronic ester $R^1B(OR)_2$ etc.) in the presence of a suitable metal catalyst (such as palladium or copper) in a suitable solvent such as 1,4-dioxane.

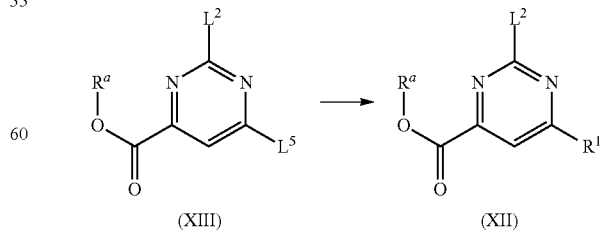

Compounds of formula (XIII), cyclic amines, boronic acids $\{R^1B(OH)_2\}$ and boronic esters $\{R^1B(OR)_2\}$ are either commercially available or well known in the art.

It will be appreciated that where Ring A, is a heterocyclic ring containing a nitrogen atom that the nitrogen atom may be suitably protected (for example a t-butoxycarbamate or benzyl group) and that the protecting group may be removed and if necessary a further reaction performed on the nitrogen (for example an alkylation, reductive amination or amidation) at any stage in the synthesis.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. For example compounds of formula (I) may be converted into further compounds of formula (I) by standard aromatic substitution reactions or by conventional functional group modifications. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogen group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulfinyl or alkylsulfonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Many of the intermediates defined herein are novel and these are provided as a further feature of the invention.

Biological Assays

The following assays can be used to measure the effects of the compounds of the present invention as ATR kinase inhibitors.

(a) Enzyme Assay—ATR

ATR for use in the in vitro enzyme assay was obtained from HeLa nuclear extract (CIL Biotech, Mons, Belgium) by immunoprecipitation with rabbit polyclonal antiserum raised to amino acids 400-480 of ATR (Tibbetts R S et al, 1999, Genes Dev. 13:152-157) contained in the following buffer (25 mM HEPES (pH7.4), 2 mM $MgCl_2$, 250 mM NaCl, 0.5 mM EDTA, 0.1 mM $Na_3VO_4$, 10% v/v glycerol, and 0.01% v/v Tween 20). ATR-antibody complexes were isolated from nuclear extract by incubating with protein A-Sepharose beads (Sigma, #P3476) for 1 hour and then through centrifugation to recover the beads. In the well of a 96-well plate, 10 μL ATR-containing Sepharose beads were incubated with 1 μg of substrate glutathione S-transferase-p53N66 ($NH_2$-terminal 66 amino acids of p53 fused to glutathione S-transferase was expressed in E. coli) in ATR assay buffer (50 mM HEPES (pH 7.4), 150 mM NaCl, 6 mM $MgCl_2$, 4 mM $MnCl_2$, 0.1 mM $Na_3VO_4$, 0.1 mM DTT, and 10% (v/v) glycerol) at 37° C. in the presence or absence of inhibitor. After 10 minutes with gentle shaking, ATP was added to a final concentration of 3 μM and the reaction continued at 37° C. for an additional 1 hour. The reaction was stopped by addition of 100 μL PBS and the reaction was transferred to a white opaque glutathione coated 96-well plate (NUNC #436033) and incubated overnight at 4° C. This plate was then washed with PBS/0.05% (v/v) Tween 20, blotted dry, and analyzed by a standard ELISA (Enzyme-Linked ImmunoSorbent Assay) technique with a phospho-serine 15 p53 (16G78) antibody (Cell Signaling Technology, #9286). The detection of phosphorylated glutathione S-transferase-p53N66 substrate was performed in combination with a goat anti-mouse horseradish peroxidase-conjugated secondary antibody (Pierce, #31430). Enhanced chemiluminescence solution (NEN, Boston, Mass.) was used to produce a signal and chemiluminescent detection was carried out via a TopCount (Packard, Meriden, Conn.) plate reader.

The resulting calculated % enzyme activity (Activity Base, IDBS) was then used to determine the $IC_{50}$ values for the compounds ($IC_{50}$ taken as the concentration at which 50% of the enzyme activity is inhibited).

(b) Cellular Assays—ATR

ATM and ATR have distinct and overlapping responses to DNA damage. They must participate together and responses must be co-ordinated. Both pathways may be activated by ionising radiation, however only ATR is activated by UV. Since UV treatment is not practical for use in a high throughput cell assay, the UV mimetic 4NQ0 (Sigma) was chosen to activate the ATR DNA damage response pathway.

Chk1, a downstream protein kinase of ATR, plays a key role in DNA damage checkpoint control. Activation of Chk1 involves phosphorylation of Ser317 and Ser345 (regarded as the preferential target for phosphorylation/activation by ATR). This assay measures a decrease in phosphorylation of Chk1 (Ser 345) in HT29 colon adenocarcinoma cells following treatment with compound and the UV mimetic 4NQ0. Compounds dose ranges were created by diluting in 100% DMSO and then further into assay media (EMEM, 10% FCS, 1% glutamine) using a Labcyte Echo Acoustic dispensing instrument. Cells were plated in 384 well Costar plates at $9 \times 10^4$ cells per ml in 40 µL EMEM, 10% FCS, 1% glutamine and grown for 24 hrs. Following addition of compound the cells were incubated for 60 minutes. A final concentration of 3 µM 4NQ0 (prepared in 100% DMSO) was then added using the Labcyte Echo and the cells incubated for a further 60mins. The cells are then fixed by adding 40 µL 3.7% v/v formaldehyde solution for 20 minutes. After removal of fix, cells were washed with PBS and permeabilised in 40 µL of PBS containing 0.1% Triton™ X-100. Cells are then washed and 15 µl primary antibody solution (pChk1 Ser345) added and the plates incubated at 4° C. overnight. The primary antibody is then washed off, and 20 µl secondary antibody solution (goat anti—rabbit Alexa Fluor 488, Invitrogen) and 1 µM Hoechst 33258 (Invitrogen) is added for 90mins at room temperature. The plates are washed and left in 40 µl PBS. Plates were then read on an ArrayS can Vti instrument to determine staining intensities, and dose responses were obtained and used to determine the $IC_{50}$ values for the compounds.

(c) Cellular—SRB Assay

The potentiation factor ($PF_{50}$) for compounds is a measure of the fold increase in effect of a chemotherapeutic agent, when used in combination with an ATR inhibitor. Specifically, this is calculated as a ratio of the $IC_{50}$ of control cell growth in the presence of a chemotherapeutic agent, typically carboplatin, divided by the $IC_{50}$ of cell growth in the presence of this agent and the ATR inhibitor of interest. For this purpose, HT29 cells were seeded at the appropriate density to ensure exponential growth throughout the time of the assay (typically 1000-1500 cells) in each well of a 96-well plate, in a volume of 80 µl and incubated overnight at 37° C. Subsequently, cells were dosed with either DMSO vehicle, or treated with test compounds at fixed concentrations (typically 1, 0.3 & 0.1 µM). Following a one hour incubation at 37° C., the cells were further treated with a 10 point dose response of the chemotherapeutic agent, based on it's known sensitivity (typically 30-0.001 ug/ml for carboplatin). Cells were left to grow for 5 days at 37° C., after which time cell growth was assessed using the sulforhodamine B (SRB) assay (Skehan, P et al, 1990 New colorimetric cytotoxic assay for anticancer-drug screening. J. Natl. Cancer Inst. 82, 1107-1112.). Specifically, the media was removed and cells fixed with 100 µl of ice cold 10% (w/v) trichloroacetic acid. The plates were then incubated at 4° C. for 20 minutes prior to washing 4 times with water. Each well was then stained with 100 µL of 0.4% (w/v) SRB in 1% acetic acid for 20 minutes before a further 4 washes with 1% acetic acid. Plates were then dried for 2 hours at room temperature and the dye was solubilized by the addition of 100 µL Tris Base pH 8.5 into each well. Plates were shaken before measuring optical density at 564 nm ($OD_{564}$). In order to calculate the PF50, the $OD_{564}$ values obtained for the dose-response curve of chemotherapeutic agent were expressed as a percentage of the value obtained from cells treated with vehicle alone. Similarly, to act as a control for inclusion of the ATR inhibitor, values from the chemotherapeutic agent tested in combination with a fixed ATR inhibitor concentration were expressed as a percentage of the value obtained from cells treated with the corresponding concentration of ATR inhibitor alone. From these internally-controlled curves, IC50 values were calculated and the PF50 was determined as the ratio of these values, as described above. Compounds are compared using the PF50 value at concentrations of ATR inhibitor that show minimal growth inhibition on their own. IC50 values were calculated with XLfit (IDBS, Surrey UK) using the dose response, 4 parameter logistic model #203. Top (max) and bottom (min) curve fitting was free and not locked to 100% to 0% respectively.

The following assays can be used to measure the effects of the compounds of the present invention as mTOR kinase inhibitors.

Enzyme—mTOR Kinase Assay (Echo)

The assay used AlphaScreen technology (Gray et al., Analytical Biochemistry, 2003, 313: 234-245) to determine the ability of test compounds to inhibit phosphorylation by recombinant mTOR.

A C-terminal truncation of mTOR encompassing amino acid residues 1362 to 2549 of mTOR (EMBL Accession No. L34075) was stably expressed as a FLAG-tagged fusion in HEK293 cells as described by Vilella-Bach et al., Journal of Biochemistry, 1999, 274, 4266-4272. The HEK293 FLAG-tagged mTOR (1362-2549) stable cell line was routinely maintained at 37° C. with 5% $CO_2$ up to a confluency of 70-90% in Dulbecco's modified Eagle's growth medium (DMEM; Invitrogen Limited, Paisley, UK Catalogue No. 41966-029) containing 10% heat-inactivated foetal calf serum (FCS; Sigma, Poole, Dorset, UK, Catalogue No. F0392), 1% L-glutamine (Gibco, Catalogue No. 25030-024) and 2 mg/ml Geneticin (G418 sulfate; Invitrogen Limited, UK Catalogue No. 10131-027). Following expression in the mammalian HEK293 cell line, expressed protein was purified using the FLAG epitope tag using standard purification techniques.

Test compounds were prepared as 10 mM stock solutions in DMSO and diluted into DMSO as required to give a range of final assay concentrations. Aliquots (120 nl) of each compound dilution were acoustically dispensed using a Labcyte Echo 550 into a well of a Greiner 384-well low volume (LV) white polystyrene plate (Greiner Bio-one). A 12.12 µl mixture of recombinant purified mTOR enzyme, 2 µM biotinylated peptide substrate (Biotin-Ahx-Lys-Lys-Ala-Asn-Gln-Val-Phe-Leu-Gly-Phe-Thr-Tyr-Val-Ala-Pro-Ser-Val-Leu-Glu-Ser-Val-Lys-Glu-NH$_2$; Bachem UK Ltd), ATP (20 µM) and a buffer solution [comprising Tris-HCl pH7.4 buffer (50 mM), EGTA (0.1 mM), bovine serum albumin (0.5 mg/mL), DTT (1.25 mM) and manganese chloride (10 mM)] was incubated at room temperature for 120 minutes.

Control wells that produced a maximum signal corresponding to maximum enzyme activity were created by using 100% DMSO instead of test compound. Control wells that produced a minimum signal corresponding to fully inhibited enzyme were created by adding LY294002 (100 uM) compound. These assay solutions were incubated for 2 hours at room temperature.

Each reaction was stopped by the addition of 5 μl of a mixture of EDTA (150 mM), bovine serum albumin (BSA; 0.5 mg/mL) and Tris-HCl pH7.4 buffer (50 mM) containing p70 S6 Kinase (T389) 1A5 Monoclonal Antibody (Cell Signalling Technology, Catalogue No. 9206B) and AlphaScreen Streptavidin donor and Protein A acceptor beads (200 ng; Perkin Elmer, Catalogue No. 6760617 respectively) were added and the assay plates were left overnight at room temperature in the dark. The resultant signals arising from laser light excitation at 680 nm were read using a Packard Envision instrument.

Phosphorylated biotinylated peptide is formed in situ as a result of mTOR mediated phosphorylation. The phosphorylated biotinylated peptide that is associated with AlphaScreen Streptavidin donor beads forms a complex with the p70 S6 Kinase (T389) 1A5 Monoclonal Antibody that is associated with Alphascreen Protein A acceptor beads. Upon laser light excitation at 680 nm, the donor bead:acceptor bead complex produces a signal that can be measured. Accordingly, the presence of mTOR kinase activity results in an assay signal. In the presence of an mTOR kinase inhibitor, signal strength is reduced. mTOR enzyme inhibition for a given test compound was expressed as an $IC_{50}$ value.

Cellular—phospho-Ser473 Akt assay

This assay determines the ability of test compounds to inhibit phosphorylation of Serine 473 in Akt as assessed using Acumen Explorer technology (Acumen Bioscience Limited), a plate reader that can be used to rapidly quantitate features of images generated by laser-scanning A MDA-MB-468 human breast adenocarcinoma cell line (LGC Promochem, Teddington, Middlesex, UK, Catalogue No. HTB-132) was routinely maintained at 37° C. with 5% $CO_2$ up to a confluency of 70-90% in DMEM containing 10% heat-inactivated FCS and 1% L-glutamine.

For the assay, the cells were detached from the culture flask using 'Accutase' (Innovative Cell Technologies Inc., San Diego, Calif., USA; Catalogue No. AT104) using standard tissue culture methods and resuspended in media to give $3.75 \times 10^4$ cells per ml. Aliquots (40 μl) of cells were seeded into each well of a black 384 well plate (Greiner, Catalogue No 781091) to give a density of ~15000 cells per well. The cells were incubated overnight at 37° C. with 5% $CO_2$ to allow them to adhere.

On day 2, the cells were treated with test compounds and incubated for 2 hours at 37° C. with 5% $CO_2$. Test compounds were prepared as 10 mM stock solutions in DMSO. Compound dosing is performed using acoustic dispensing system (Labcyte Echo® Liquid Handling Systems (Labcyte Inc. 1190 Borregas Avenue, Sunnyvale, Calif. 94089 USA). As a minimum response control, each plate contained wells having a final concentration of 100 μM LY294002 (Calbiochem, Beeston, UK, Catalogue No. 440202). As a maximum response control, wells contained 1% DMSO instead of test compound. Following incubation, the contents of the plates were fixed by treatment with a 1.6% aqueous formaldehyde solution (Sigma, Poole, Dorset, UK, Catalogue No. F1635) at room temperature for 1 hour.

All subsequent aspiration and wash steps were carried out using a Tecan plate washer (aspiration speed 10 mm/sec). The fixing solution was removed and the contents of the plates were washed with phosphate-buffered saline (PBS; 80 μl; Gibco, Catalogue No. 10010015). The contents of the plates were treated for 10 minutes at room temperature with an aliquot (20 μl) of a cell permeabilisation buffer consisting of a mixture of PBS and 0.5% Tween-20. The 'permeabilisation' buffer was removed and non-specific binding sites were blocked by treatment for 1 hour at room temperature of an aliquot (20 μl) of a blocking buffer consisting of 5% dried skimmed milk ['Marvel' (registered trade mark); Premier Beverages, Stafford, GB] in a mixture of PBS and 0.05% Tween-20. The 'blocking' buffer was removed and the cells were incubated for 1 hour at room temperature with rabbit anti phospho-Akt (Ser473) antibody solution (20 μl per well; Cell Signalling, Hitchin, Herts, U.K., Catalogue No 9277) that had been diluted 1:500 in 'blocking' buffer. Cells were washed three times in a mixture of PBS and 0.05% Tween-20. Subsequently, cells were incubated for 1 hour at room temperature with Alexafluor488 labelled goat anti-rabbit IgG (20 μl per well; Molecular Probes, Invitrogen Limited, Paisley, UK, Catalogue No. A11008) that had been diluted 1:500 in 'blocking' buffer. Cells were washed 3 times with a mixture of PBS and 0.05% Tween-20. An aliquot of PBS (50 μl) was added to each well and the plates were sealed with black plate sealers and the fluorescence signal was detected and analysed.

Fluorescence dose response data obtained with each compound were analysed and the degree of inhibition of Serine 473 in Akt was expressed as an $IC_{50}$ value.

Compounds that show reduced activity against mTOR may ameliorate off target effects.

Although the pharmacological properties of the compounds of formula (I) vary with structural change as expected, in general, it is believed that activity possessed by compounds of formula (I) may be demonstrated at the following concentrations or doses in one or more of the above tests (a) to (d):—

Test (a):—$IC_{50}$ versus ATR kinase at less than 10 μM, in particular 0.001-1 μM for many compounds.

The following examples were tested in enzyme assay Test (a):

| Example | ATR average IC50 uM | ATR number of individual tests |
|---|---|---|
| 1.01 | 0.03403 | 3 |
| 2.02 | 0.003747 | 3 |
| 2.03 | 0.005607 | 4 |

The following examples were tested in cell assay Test (b):

| Example | ATR average IC50 uM | ATR number of individual tests |
|---|---|---|
| 1.01 | 0.581 | 4 |
| 2.01 | 0.2355 | 14 |
| 2.02 | 0.05834 | 36 |
| 2.03 | 0.007053 | 16 |
| 2.04 | 0.02182 | 9 |
| 2.05 | 0.07577 | 4 |
| 2.06 | 0.01292 | 2 |
| 2.07 | 0.002578 | 2 |
| 2.08 | 0.002757 | 2 |
| 2.09 | 0.1593 | 2 |
| 2.10 | 0.109 | 2 |
| 2.11 | 0.01376 | 2 |
| 3.01 | 0.01279 | 4 |
| 3.02 | 0.008428 | 3 |

-continued

| Example | ATR average IC50 uM | ATR number of individual tests |
|---|---|---|
| 4.01 | 0.05361 | 4 |
| 4.02 | 0.03977 | 3 |
| 4.03 | 0.05112 | 2 |
| 5.01 | 0.06255 | 3 |
| 5.02 | 0.07085 | 3 |
| 5.03 | 0.03313 | 3 |
| 5.04 | 0.01618 | 3 |
| 5.05 | 0.01828 | 3 |
| 5.06 | 0.0444 | 3 |
| 5.07 | 0.02899 | 2 |
| 5.08 | 0.01007 | 2 |
| 5.09 | 0.01796 | 2 |
| 5.10 | 0.04703 | 2 |

The following examples were tested in the Cellular SRB assay Test (c)

| Cell | Treatment | Number of individual tests | IC50 ug/ml | S.D. | PF50 |
|---|---|---|---|---|---|
| HT29 | Carboplatin | 2 | 11.798 | 1.220 | |
| HT29 | Carboplatin + 0.3 uM Example 2.03 | 2 | 0.63 | 0.064 | 18.721 |
| HT29 | Carboplatin + 0.1 uM Example 2.03 | 2 | 2.009 | 0.274 | 5.887 |
| HT29 | Carboplatin + 0.03 uM Example 2.03 | 2 | 5.740 | 0.075 | 2.057 |
| HT29 | Carboplatin | 2 | 12.519 | 1.224 | |
| HT29 | Carboplatin + 0.3 uM Example 2.02 | 2 | 2.991 | 0.507 | 4.211 |
| HT29 | Carboplatin + 0.1 uM Example 2.02 | 2 | 6.372 | 0.073 | 1.966 |
| HT29 | Carboplatin + 0.03 uM Example 2.02 | 2 | 9.395 | 0.680 | 1.331 |

Note:
averages are arithmetric means.

Compounds may be further selected on the basis of further biological or physical properties which may be measured by techniques known in the art and which may be used in the assessment or selection of compounds for therapeutic or prophylactic application.

The compounds of the present invention are advantageous in that they possess pharmacological activity. In particular, the compounds of the present invention modulate ATR kinase. The inhibitory properties of compounds of formula (I) may be demonstrated using the test procedures set out herein and in the experimental section. Accordingly, the compounds of formula (I) may be used in the treatment (therapeutic or prophylactic) of conditions/diseases in human and non-human animals which are mediated by ATR kinase.

The invention also provides a pharmaceutical composition comprising a compound of formula (I), or a pharmaceutically acceptable salt thereof, as defined herein in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 1 mg to 1 g of active agent (more suitably from 1 to 250 mg, for example from 1 to 100 mg) compounded with an appropriate and convenient amount of excipients which may vary from about 5 to about 98 percent by weight of the total composition.

The size of the dose for therapeutic or prophylactic purposes of a compound of formula I will naturally vary according to the nature and severity of the disease state, the age and sex of the animal or patient and the route of administration, according to well known principles of medicine.

In using a compound of formula (I) for therapeutic or prophylactic purposes it will generally be administered so that a daily dose in the range, for example, 1 mg/kg to 100 mg/kg body weight is received, given if required in divided doses. In general, lower doses will be administered when a parenteral route is employed. Thus, for example, for intravenous administration, a dose in the range, for example, 1 mg/kg to 25 mg/kg body weight will generally be used. Similarly, for administration by inhalation, a dose in the range, for example, 1 mg/kg to 25 mg/kg body weight will be used. Typically, unit dosage forms will contain about 10 mg to 0.5 g of a compound of this invention.

As stated herein, it is known that ATR kinase have roles in tumourigenesis as well as numerous other diseases. We have found that the compounds of formula (I) possess potent anti-tumour activity which it is believed is obtained by way of inhibition of ATR kinase.

Accordingly, the compounds of the present invention are of value as anti-tumour agents. Particularly, the compounds of the present invention are of value as anti-proliferative, apoptotic and/or anti-invasive agents in the containment and/or treatment of solid and/or liquid tumour disease. Particularly, the compounds of the present invention are expected to be useful in the prevention or treatment of those tumours which are sensitive to inhibition of ATR. Further, the compounds of the present invention are expected to be useful in the prevention or treatment of those tumours which are mediated alone or in part by ATR. The compounds may thus be used to produce an ATR enzyme inhibitory effect in a warm-blooded animal in need of such treatment.

As stated herein, inhibitors of ATR kinase should be of therapeutic value for the treatment of proliferative disease such as cancer and in particular solid tumours such as carcinoma and sarcomas and the leukaemias and lymphoid malignancies and in particular for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias [including chronic lymphocytic leukaemia (CLL), acute lymphoctic leukaemia (ALL) and chronic myelogenous leukaemia (CML)], multiple myeloma and lymphomas.

Anti-cancer effects which are accordingly useful in the treatment of cancer in a patient include, but are not limited to, anti-tumour effects, the response rate, the time to disease progression and the survival rate. Anti-tumour effects of a method of treatment of the present invention include but are not limited to, inhibition of tumour growth, tumour growth delay, regression of tumour, shrinkage of tumour, increased time to regrowth of tumour on cessation of treatment, slowing of disease progression. Anti-cancer effects include prophylactic treatment as well as treatment of existing disease.

A ATR kinase inhibitor, or a pharmaceutically acceptable salt thereof, may also be useful for the treatment patients with cancers, including, but not limited to, haematologic malignancies such as leukaemia, multiple myeloma, lymphomas such as Hodgkin's disease, non-Hodgkin's lymphomas (including mantle cell lymphoma), and myelodysplastic syndromes, and also solid tumours and their metastases such as breast cancer, lung cancer (non-small cell lung cancer (NSCL), small cell lung cancer (SCLC), squamous cell carcinoma), endometrial cancer, tumours of the central nervous system such as gliomas, dysembryoplastic neuroepithelial tumour, glioblastoma multiforme, mixed gliomas, medulloblastoma, retinoblastoma, neuroblastoma, germinoma and teratoma, cancers of the gastrointestinal tract such as gastric cancer, oesophagal cancer, hepatocellular (liver) carcinoma, cholangiocarcinomas, colon and rectal carcinomas, cancers of the small intestine, pancreatic cancers, cancers of the skin such as melanomas (in particular metastatic melanoma), thyroid cancers, cancers of the head and neck and cancers of the salivary glands, prostate, testis, ovary, cervix, uterus, vulva, bladder, kidney (including renal cell carcinoma, clear cell and renal oncocytoma), squamous cell carcinomas, sarcomas such as osteosarcoma, chondrosarcoma, leiomyosarcoma, soft tissue sarcoma, Ewing's sarcoma, gastrointestinal stromal tumour (GIST), Kaposi's sarcoma, and paediatric cancers such as rhabdomyosarcomas and neuroblastomas.

The compounds of the present invention and the methods of treatment comprising the administering or use of a ATR kinase inhibitor, or a pharmaceutically acceptable salt thereof, are expected to be particularly useful for the treatment of patients with lung cancer, prostate cancer, melanoma, ovarian cancer, breast cancer, endometrial cancer, kidney cancer, gastric cancer, sarcomas, head and neck cancers, tumours of the central nervous system and their metastases, and also for the treatment of patients with acute myeloid leukaemia.

According to a further aspect of the invention there is provided a compound of formula (I), or a pharmaceutically acceptable salt thereof, as defined herein for use as a medicament in a warm-blooded animal such as man.

According to a further aspect of the invention, there is provided a compound of formula (I), or a pharmaceutically acceptable salt thereof, as defined herein for use in the production of an anti-proliferative effect in a warm-blooded animal such as man.

According to a further aspect of the invention, there is provided a compound of formula (I), or a pharmaceutically acceptable salt thereof, as defined herein for use in the production of an apoptotic effect in a warm-blooded animal such as man.

According to a further feature of the invention there is provided the use of a compound of formula (I), or a pharmaceutically acceptable salt thereof, as defined herein for use in a warm-blooded animal such as man as an anti-invasive agent in the containment and/or treatment of proliferative disease such as cancer.

According to a further aspect of the invention, there is provided the use of a compound of formula (I), or a pharmaceutically acceptable salt thereof, as defined herein for the production of an anti-proliferative effect in a warm-blooded animal such as man.

According to a further feature of this aspect of the invention there is provided the use of a compound of formula (I), or a pharmaceutically acceptable salt thereof, as defined herein in the manufacture of a medicament for use in the production of an anti-proliferative effect in a warm-blooded animal such as man.

According to a further aspect of the invention, there is provided the use of a compound of formula (I), or a pharmaceutically acceptable salt thereof, as defined herein for the production of an apoptotic effect in a warm-blooded animal such as man.

According to a further feature of this aspect of the invention there is provided the use of a compound of formula (I), or a pharmaceutically acceptable salt thereof, as defined herein in the manufacture of a medicament for use in the production of an apoptotic effect in a warm-blooded animal such as man.

According to a further feature of the invention there is provided the use of a compound of formula (I), or a pharmaceutically acceptable salt thereof, as defined herein in the manufacture of a medicament for use in a warm-blooded animal such as man as an anti-invasive agent in the containment and/or treatment of proliferative disease such as cancer.

According to a further feature of this aspect of the invention there is provided a method for producing an anti-proliferative effect in a warm-blooded animal, such as man, in need of such treatment which comprises administering to said animal an effective amount of a compound of formula (I), or a pharmaceutically acceptable salt thereof, as defined herein.

According to a further feature of this aspect of the invention there is provided a method for producing an anti-invasive effect by the containment and/or treatment of solid tumour disease in a warm-blooded animal, such as man, in need of such treatment which comprises administering to said animal an effective amount of a compound of formula (I), or a pharmaceutically acceptable salt thereof, as defined herein.

According to a further aspect of the invention there is provided the use of a compound of formula (I), or a pharmaceutically acceptable salt thereof, as defined herein in the manufacture of a medicament for use in the prevention or treatment of proliferative disease such as cancer in a warm-blooded animal such as man.

According to a further feature of this aspect of the invention there is provided a method for the prevention or treatment of proliferative disease such as cancer in a warm-blooded animal, such as man, in need of such treatment which comprises administering to said animal an effective amount of a compound of formula (I), or a pharmaceutically acceptable salt thereof, as defined herein.

According to a further aspect of the invention there is provided a compound of formula (I), or a pharmaceutically acceptable salt thereof, as defined herein for use in the prevention or treatment of those tumours which are sensitive to inhibition of ATR kinase.

According to a further feature of this aspect of the invention there is provided the use of a compound of formula (I), or a pharmaceutically acceptable salt thereof, as defined herein in the manufacture of a medicament for use in the prevention or treatment of those tumours which are sensitive to inhibition of ATR kinase.

According to a further feature of this aspect of the invention there is provided a method for the prevention or treatment of those tumours which are sensitive to inhibition of ATR kinase which comprises administering to said animal an effective amount of a compound of formula (I), or a pharmaceutically acceptable salt thereof, as defined herein.

According to a further aspect of the invention there is provided a compound of formula (I), or a pharmaceutically acceptable salt thereof, as defined herein for use in providing a ATR kinase inhibitory effect.

According to a further feature of this aspect of the invention there is provided the use of a compound of formula (I), or a pharmaceutically acceptable salt thereof, as defined herein in the manufacture of a medicament for use in providing a ATR kinase inhibitory effect.

According to a further aspect of the invention there is also provided a method for providing a ATR kinase inhibitory effect which comprises administering an effective amount of a compound of formula I, or a pharmaceutically acceptable salt thereof, as defined herein.

According to a further feature of the invention there is provided a compound of formula I, or a pharmaceutically acceptable salt thereof, as defined herein for use in the treatment of cancer, inflammatory diseases, obstructive airways diseases, immune diseases or cardiovascular diseases.

According to a further feature of the invention there is provided a compound of formula I, or a pharmaceutically acceptable salt thereof, as defined herein for use in the treatment of solid tumours such as carcinoma and sarcomas and the leukaemias and lymphoid malignancies.

According to a further feature of the invention there is provided a compound of formula I, or a pharmaceutically acceptable salt thereof, as defined herein for use in the treatment of cancer of the breast, colorectum, lung (including small cell lung cancer, non-small cell lung cancer and bronchioalveolar cancer) and prostate.

According to a further feature of the invention there is provided a compound of formula (I), or a pharmaceutically acceptable salt thereof, as defined herein for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL, CLL and CML), multiple myeloma and lymphomas.

According to a further feature of the invention there is provided a compound of formula (I), or a pharmaceutically acceptable salt thereof, as defined herein for use in the treatment of cancer of the bile duct, bone, bladder, head and neck, kidney, liver, gastrointestinal tissue, oesophagus, ovary, endometrium, pancreas, skin, testes, thyroid, uterus, cervix and vulva, and of leukaemias (including ALL, CLL and CML), multiple myeloma and lymphomas.

According to a further feature of the invention there is provided a compound of formula (I), or a pharmaceutically acceptable salt thereof, as defined herein for use in the treatment of lung cancer, prostate cancer, melanoma, ovarian cancer, breast cancer, endometrial cancer, kidney cancer, gastric cancer, sarcomas, head and neck cancers, tumours of the central nervous system and their metastases, and also for the treatment acute myeloid leukaemia.

According to a further feature of the invention there is provided the use of a compound of formula (I), or a pharmaceutically acceptable salt thereof, as defined herein in the manufacture of a medicament for use in the treatment of cancer, inflammatory diseases, obstructive airways diseases, immune diseases or cardiovascular diseases.

According to a further feature of the invention there is provided the use of a compound of formula (I), or a pharmaceutically acceptable salt thereof, as defined herein in the manufacture of a medicament for use in the treatment of solid tumours such as carcinoma and sarcomas and the leukaemias and lymphoid malignancies.

According to a further feature of the invention there is provided the use of a compound of formula (I), or a pharmaceutically acceptable salt thereof, as defined herein in the manufacture of a medicament for use in the treatment of cancer of the breast, colorectum, lung (including small cell lung cancer, non-small cell lung cancer and bronchioalveolar cancer) and prostate.

According to a further feature of the invention there is provided the use of a compound of formula (I), or a pharmaceutically acceptable salt thereof, as defined herein in the manufacture of a medicament for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL, CLL and CML), multiple myeloma and lymphomas.

According to a further feature of the invention there is provided the use of a compound of formula (I), or a pharmaceutically acceptable salt thereof, as defined herein in the manufacture of a medicament for use in the treatment of lung cancer, prostate cancer, melanoma, ovarian cancer, breast cancer, endometrial cancer, kidney cancer, gastric cancer, sarcomas, head and neck cancers, tumours of the central nervous system and their metastases, and also for the treatment acute myeloid leukaemia.

According to a further feature of the invention there is provided a method for treating cancer, inflammatory diseases, obstructive airways diseases, immune diseases or cardiovascular diseases in a warm blooded animal such as man that is in need of such treatment which comprises administering an effective amount of a compound of formula (I), or a pharmaceutically acceptable salt thereof, as defined herein.

According to a further feature of the invention there is provided a method for treating solid tumours such as carcinoma and sarcomas and the leukaemias and lymphoid malignancies in a warm blooded animal such as man that is in need of such treatment which comprises administering an effective amount of a compound of formula (I), or a pharmaceutically acceptable salt thereof, as defined herein.

According to a further feature of the invention there is provided a method for treating cancer of the breast, colorectum, lung (including small cell lung cancer, non-small cell lung cancer and bronchioalveolar cancer) and prostate in a warm blooded animal such as man that is in need of such treatment which comprises administering an effective amount of a compound of formula (I), or a pharmaceutically acceptable salt thereof, as defined herein.

According to a further feature of the invention there is provided a method for treating cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL, CLL and CML), multiple myeloma and lymphomas in a warm blooded animal such as man that is in need of such treatment which comprises administering an effective amount of a compound of formula (I), or a pharmaceutically acceptable salt thereof, as defined herein.

According to a further feature of the invention there is provided a method for treating lung cancer, prostate cancer, melanoma, ovarian cancer, breast cancer, endometrial cancer, kidney cancer, gastric cancer, sarcomas, head and neck cancers, tumours of the central nervous system and their metastases, and acute myeloid leukaemia in a warm blooded animal such as man that is in need of such treatment which comprises administering an effective amount of a compound of formula (I), or a pharmaceutically acceptable salt thereof, as defined herein.

As stated herein, the in vivo effects of a compound of formula (I) may be exerted in part by one or more metabolites that are formed within the human or animal body after administration of a compound of formula (I).

The invention further relates to combination therapies wherein a compound of formula (I), or a pharmaceutically acceptable salt thereof, or a pharmaceutical composition or formulation comprising a compound of formula (I) is administered concurrently or sequentially or as a combined preparation with another treatment of use in the control of oncology disease.

In particular, the treatment defined herein may be applied as a sole therapy or may involve, in addition to the compounds of the invention, conventional surgery or radiotherapy or chemotherapy. Accordingly, the compounds of the invention can also be used in combination with existing therapeutic agents for the treatment of cancer.

Suitable agents to be used in combination include:—
(i) antiproliferative/antineoplastic drugs and combinations thereof, as used in medical oncology such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like paclitaxel and taxotere); and topoisomerase inhibitors (for example epipodophyllotoxins like etoposide and teniposide, amsacrine, topotecan and camptothecins);
(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;
(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661), and metalloproteinase inhibitors like marimastat and inhibitors of urokinase plasminogen activator receptor function);
(iv) inhibitors of growth factor function: for example such inhibitors include growth factor antibodies and growth factor receptor antibodies (for example the anti-erbB2 antibody trastuzumab [Herceptin™] and the anti-erbB1 antibody cetuximab [C225]); such inhibitors also include, for example, tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033) and erbB2 tyrosine kinase inhibitors such as lapatinib), inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)) and inhibitors of cell signalling through MEK and/or Akt kinases;
(v) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SU11248 (sunitinib; WO 01/60814), and compounds that work by other mechanisms (for example linomide, inhibitors of integrin αvβ3 function and angiostatin)];
(vi) vascular damaging agents such as combretastatin A4 and compounds disclosed in International Patent Applications WO 99/02166, WO 00/40529, WO 00/41669, WO 01/92224, WO 02/04434 and WO 02/08213;
(vii) antisense therapies, for example those which are directed to the targets listed above, such as ISIS 2503, an anti-ras antisense agent;
(viii) gene therapy approaches, including approaches to replace aberrant genes such as aberrant p53 or aberrant BRCA1 or BRCA2, GDEPT (gene-directed enzyme prodrug therapy) approaches such as those using cytosine deaminase, thymidine kinase or a bacterial nitroreductase enzyme and approaches to increase patient tolerance to chemotherapy or radiotherapy such as multi-drug resistance gene therapy; and
(ix) immunotherapeutic approaches, including ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

According to a further aspect of the invention there is provided the use of a compound of formula (I), or a pharmaceutically acceptable salt thereof, in the preparation of a medicament for use as an adjunct in cancer therapy or for potentiating tumour cells for treatment with ionising radiation or chemotherapeutic agents.

According to another aspect of the invention there is provided a compound of formula (I), or a pharmaceutically acceptable salt thereof, in combination with ionising radiation or chemotherapeutic agents for use in the treatment of cancer.

The invention will now be further explained by reference to the following illustrative examples.

Unless stated otherwise, starting materials were commercially available. All solvents and commercial reagents were of laboratory grade and were used as received.

General Experimental

The invention will now be illustrated in the following Examples in which, generally:

(i) operations were carried out at room temperature (RT), i.e. in the range 17 to 25° C. and under an atmosphere of an inert gas such as $N_2$ or Ar unless otherwise stated;

(ii) in general, the course of reactions was followed by thin layer chromatography (TLC) and/or analytical high performance liquid chromatography (HPLC) which was usually coupled to a mass spectrometer (LCMS). The reaction times that are given are not necessarily the minimum attainable;

(iii) when necessary, organic solutions were dried over anhydrous $MgSO_4$ or $Na_2SO_4$, work-up procedures were carried out using traditional phase separating techniques or by using SCX as described in (xiii), evaporations were carried out either by rotary evaporation in vacuo or in a Genevac HT-4/EZ-2 or Biotage V10;

(iv) yields, where present, are not necessarily the maximum attainable, and when necessary, reactions were repeated if a larger amount of the reaction product was required;

(v) in general, the structures of the end-products of the formula (I) were confirmed by nuclear magnetic resonance (NMR) and/or mass spectral techniques; electrospray mass spectral data were obtained using a Waters ZMD or Waters ZQ LC/mass spectrometer acquiring both positive and negative ion data, and generally, only ions relating to the parent structure are reported; proton NMR chemical shift values were measured on the delta scale using either a Bruker DPX300 spectrometer operating at a field strength of 300 MHz, a Bruker DRX400 operating at 400 MHz, a Bruker DRX500 operating at 500 MHz or a Bruker AV700 operating at 700 MHz. Unless otherwise stated, NMR spectra were obtained at 400 MHz in $d^6$-dimethylsulfoxide. The following abbreviations have been used: s, singlet; d, doublet; t, triplet; q, quartet; m, multiplet; br, broad; qn, quintet;

(vi) Unless stated otherwise compounds containing an asymmetric carbon and/or sulphur atom were not resolved;

(vii) Intermediates were not necessarily fully purified but their structures and purity were assessed by TLC, analytical HPLC, and/or NMR analysis and/or mass spectrometry;

(viii) unless otherwise stated, flash column chromatography (FCC) was performed on Merck Kieselgel silica (Art. 9385) or on reversed phase silica (Fluka silica gel 90 C18) or on Silicycle cartridges (40-63 µm silica, 4 to 330 g weight) or on Grace resolv cartridges (4-120 g) or on RediSep Rf 1.5 Flash columns or on RediSep Rf high performance Gold Flash columns (150-415 g weight) or on RediSep Rf Gold C18 Reversed-phase columns (20-40 µm silica) either manually or automated using an Isco Combi Flash Companion system or similar system;

(ix) Preparative reverse phase HPLC(RP HPLC) was performed on C18 reversed-phase silica, for example on a Waters 'Xterra' or 'XBridge' preparative reversed-phase column (5 µm silica, 19 mm diameter, 100 mm length) or on a Phenomenex "Gemini" or 'AXIA' preparative reversed-phase column (5 µm silica, 110A, 21.1 mm diameter, 100 mm length) using decreasingly polar mixtures as eluent, for example [containing 0.1-5% formic acid or 1-5% aqueous ammonium hydroxide (d=0.88)] as solvent A and acetonitrile as solvent B or MeOH:MeCN 3:1; a typical procedure would be as follows: a solvent gradient over 9.5 minutes, at 25 mL per minute, from a 85:15 (or alternative ratio as appropriate) mixture of solvents A and B respectively to a 5:95 mixture of solvents A and B;

(x) the following analytical HPLC methods were used; in general, reverse-phase silica was used with a flow rate of about 1 mL/minute and detection was by Electrospray Mass Spectrometry and by UV absorbance at a wavelength of 254 nm. Analytical HPLC was performed on C18 reverse-phase silica, on a Phenomenex "Gemini" preparative reversed-phase column (5 µm silica, 110 A, 2 mm diameter, 50 mm length) using decreasingly polar mixtures as eluent, for example decreasingly polar mixtures of water (containing 0.1% formic acid or 0.1% ammonia) as solvent A and acetonitrile as solvent B or MeOH:MeCN 3:1. A typical analytical HPLC method would be as follows: a solvent gradient over 4 minutes, at approximately 1 mL per minute, from a 95:5 mixture of solvents A and B respectively to a 5:95 mixture of solvents A and B;

(xi) Where certain compounds were obtained as an acid-addition salt, for example a mono-hydrochloride salt or a di-hydrochloride salt, the stoichiometry of the salt was based on the number and nature of the basic groups in the compound, the exact stoichiometry of the salt was generally not determined, for example by means of elemental analysis data;

(xii) Where reactions refer to the use of a microwave, one of the following microwave reactors were used: Biotage Initiator, Personal Chemistry Emrys Optimizer, Personal Chemistry Smithcreator or CEM Explorer;

(xiii) Compounds were purified by strong cation exchange (SCX) chromatography using Isolute SPE flash SCX-2 or SCX-3 columns (International Sorbent Technology Limited, Mid Glamorgan, UK);

(xiv) the following preparative chiral HPLC methods were used; in general a flow rate of between 10-350 ml/minute and detection was by UV absorbance at a typical wavelength of 254 nm. A sample concentration of about 1-100 mg/ml was used in a suitable solvent mixture such as MeOH, EtOH or iPA optionally mixed with isohexane or heptane with an injection volume of between 0.5-100 ml and run time of between 10-150 minutes and a typical oven temperature of 25-35° C.;

(xv) the following analytical chiral HPLC methods were used; in general a flow rate of 1 ml/minute and detection was by UV absorbance at a typical wavelength of 254 nm. A sample concentration of about 1 mg/ml was used in a suitable solvent such as EtOH with an injection volume of about 10 µl and run time of between 10-60 minutes and a typical oven temperature of 25-35° C.;

(xvi) the following preparative chiral SFC (supercritical fluid chromatography) methods were used; in general a flow rate of about 70 ml/minute and detection was by UV absorbance at a typical wavelength of 254 nm. A sample concentration of about 100 mg/ml was used in a suitable solvent such as MeOH with an injection volume of about 0.5 ml and run time of between 10-150 minutes and a typical oven temperature of 25-35° C.;

(xvii) in general Examples were named using ACD Name Ver 10.06 and intermediate compounds were named using "Structure to Name" part of ChemDraw Ultra 11.0.2 by CambridgeSoft;

(xviii) In addition to the ones mentioned above, the following abbreviations have been used:

| DMF | N,N-dimethylformamide | DMA | N,N-dimethylacetamide |
|---|---|---|---|
| DCM | Dichloromethane | THF | tetrahydrofuran |
| conc. | Concentrated | m/z | mass spectrometry peak(s) |
| TBAF | tetra n-butylammonium fluoride | NMP | 1-methylpyrrolidin-2-one |
| EtOAc | ethyl acetate | DIPEA | N,N-diisopropylethylamine |
| DME | 1,2-dimethoxyethane | MeOH | methanol |

| | | | |
|---|---|---|---|
| DMF | N,N-dimethylformamide | DMA | N,N-dimethylacetamide |
| MeCN | Acetonitrile | TBAB | tetra n-butylammonium bromide |
| Et2O | diethyl ether | DBU | 1,8-diazabicyclo[5.4.0]undec-7-ene |
| Ac2O | acetic anhydride | DMAP | 4-dimethylaminopyridine |
| h | hour(s) | EtOH | ethanol |
| MTBE | Methyl tert-butyl ether | | |

EXAMPLE 1.01

4-{4-[(3R)-3-Methylmorpholin-4-yl]-6-[((R)—S-methylsulfonimidoyl)methyl]pyrimidin-2-yl}-1H-pyrrolo[2,3-b]pyridine

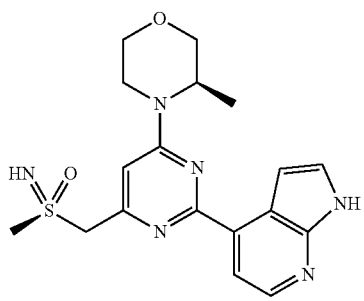 [SMILES: C[C@@H]1COCCN1c1cc(C[S@](C)(=N)=O)nc(-c2ccnc3[nH]ccc23)n1]

(R)-3-Methyl-4-(6-((R)—S-methylsulfonimidoylmethyl)-2-(1-tosyl-1H-pyrrolo[2,3-b]pyridin-4-yl)pyrimidin-4-yl)morpholine (98 mg, 0.18 mmol) was dissolved in MeOH (10 ml) and DCM (10 ml) and heated to 50° C. Sodium hydroxide, 2M aqueous solution (0.159 ml, 0.32 mmol) was then added and heating continued for 5 hours. The reaction mixture was evaporated and the residue dissolved in DME:water:MeCN 2:1:1 (4 ml) and then purified by preparative HPLC using decreasingly polar mixtures of water (containing 1% $NH_3$) and MeCN as eluents. Fractions containing the desired compound were evaporated and the residue triturated with $Et_2O$ (1 ml) to afford the title compound (34.6 mg, 49%); $^1H$ NMR (400 MHz, $CDCl_3$) 1.40 (3H, d), 3.17 (3H, s), 3.39 (1H, tt), 3.62 (1H, td), 3.77 (1H, dd), 3.85 (1H, d), 4.08 (1H, dd), 4.18 (1H, d), 4.37-4.48 (2H, q), 4.51 (1H, s), 6.59 (1H, s), 7.35 (1H, t), 7.46 (1H, d), 8.06 (1H, d), 8.42 (1H, d), 10.16 (1H, s); m/z: (ES+) $MH^+$, 387.19.

The (R)-3-methyl-4-(6-((R)—S-methylsulfonimidoylmethyl)-2-(1-tosyl-1H-pyrrolo[2,3-b]pyridin-4-yl)pyrimidin-4-yl)morpholine, used as starting material, can be prepared as follows:

a) (R)-3-methylmorpholine (7.18 g, 71.01 mmol) and triethylamine (12.87 ml, 92.31 mmol) were added to methyl 2,4-dichloropyrimidine-6-carboxylate (14.70 g, 71.01 mmol) in DCM (100 ml). The resulting mixture was stirred at RT for 18 hours. Water (100 ml) was added, the layers separated and extracted with DCM (3×75 ml). The combined organics were dried over $MgSO_4$, concentrated in vacuo and the residue triturated with $Et_2O$ to yield (R)-methyl 2-chloro-6-(3-methylmorpholino)pyrimidine-4-carboxylate (14.77 g, 77%); $^1H$ NMR (400 MHz, $CDCl_3$) 1.35 (3H, d), 3.34 (1H, td), 3.55 (1H, td), 3.70 (1H, dd), 3.81 (1H, d), 3.97 (3H, s), 4.03 (1H, dd), 4.12 (1H, br s), 4.37 (1H, br s), 7.15 (1H, s); m/z: (ESI+) $MH^+$, 272.43. The liquors were concentrated onto silica and purified by chromatography on silica eluting with a gradient of 20 to 40% EtOAc in isohexane. Fractions containing product were combined and evaporated to afford (R)-methyl 2-chloro-6-(3-methylmorpholino)pyrimidine-4-carboxylate (1.659 g, 9%); $^1H$ NMR (400 MHz, $CDCl_3$) 1.35 (3H, d), 3.33 (1H, td), 3.55 (1H, td), 3.69 (1H, dd), 3.80 (1H, d), 3.97 (3H, s), 4.03 (1H, dd), 4.12 (1H, br s), 4.36 (1H, br s), 7.15 (1H, s); m/z: (ESI+) $MH^+$, 272.43.

b) Lithium borohydride, 2M in THF (18 ml, 36.00 mmol) was added dropwise to (R)-methyl 2-chloro-6-(3-methylmorpholino)pyrimidine-4-carboxylate (16.28 g, 59.92 mmol) in THF (200 ml) at 0° C. over a period of 20 minutes under nitrogen. The resulting solution was stirred at 0° C. for 30 minutes and then allowed to warm to RT and stirred for a further 18 hours. Water (200 ml) was added and the THF evaporated. The aqueous layer was extracted with EtOAc (2×100 ml) and the organic phases combined, dried over MgSO4 and then evaporated to afford (R)-(2-chloro-6-(3-methylmorpholino)pyrimidin-4-yl)methanol (14.54 g, 100%) which was used in the next step without purification; $^1H$ NMR (400 MHz, $CDCl_3$) 1.32 (3H, d), 2.65 (1H, br s), 3.25-3.32 (1H, m), 3.51-3.57 (1H, m), 3.67-3.70 (1H, m), 3.78 (1H, d), 3.98-4.09 (2H, m), 4.32 (1H, br s), 4.59 (2H, s), 6.44 (1H, s); m/z: (ESI+) $MH^+$, 244.40.

c) Methanesulfonyl chloride (4.62 ml, 59.67 mmol) was added dropwise to (R)-(2-chloro-6-(3-methylmorpholino)pyrimidin-4-yl)methanol (14.54 g, 59.67 mmol) and triethylamine (8.32 ml, 59.67 mmol) in DCM (250 ml) at 25° C. over a period of 5 minutes. The resulting solution was stirred at 25° C. for 90 minutes. The reaction mixture was quenched with water (100 ml) and extracted with DCM (2×100 ml). The organic phases were combined, dried over $MgSO_4$, filtered and evaporated to afford (R)-(2-chloro-6-(3-methylmorpholino)pyrimidin-4-yl)methyl methanesulfonate (20.14 g, 105%) which was used in the next step without further purification; $^1H$ NMR (400 MHz, $CDCl_3$) 1.33 (3H, d), 3.13 (3H, s), 3.27-3.34 (1H, m), 3.51-3.57 (1H, m), 3.66-3.70 (1H, m), 3.79 (1H, d), 3.99-4.03 (2H, m), 4.34 (1H, br s), 5.09 (2H, d), 6.52 (1H, s); m/z: (ESI+) $MH^+$, 322.83.

Alternatively, this step can be carried out as follows:

In a 3 L fixed reaction vessel with a Huber 360 heater/chiller attached, under a nitrogen atmosphere, triethylamine (0.120 L, 858.88 mmol) was added in one go to a stirred solution of (R)-(2-chloro-6-(3-methylmorpholino)pyrimidin-4-yl)methanol (161 g, 660.68 mmol) in DCM (7.5vol) (1.2 L) at 20° C. (3° C. exotherm seen). The mixture was cooled to 5° C. and then methanesulfonyl chloride (0.062 L, 792.81 mmol) was added dropwise over 15 minutes, not allowing the internal temperature to exceed 15° C. The reaction mixture was stirred at 15° C. for 2 hours and then held (not stirring) overnight at RT under a nitrogen atmosphere. Water (1.6 L, 10 vol) was added and the aqueous layer was separated and then extracted with DCM (2×1.6 L, 2×10 vol). The organics were combined, washed with 50% brine/water (1.6 L, 10 vol), dried over magnesium sulphate, filtered and then evaporated to afford a mixture of approximately two thirds (R)-(2-chloro-6-(3-methylmorpholino)pyrimidin-4-yl)methyl methanesulfonate and one third (R)-4-(2-chloro-6-(chloromethyl)pyrimidin-4-yl)-3-methylmorpholine (216 g) which was used in the next step without further purification.

d) Lithium iodide (17.57 g, 131.27 mmol) was added to (R)-(2-chloro-6-(3-methylmorpholino)pyrimidin-4-yl)methyl methanesulfonate (19.2 g, 59.67 mmol) in dioxane (300 ml) and heated to 100° C. for 2 hours under nitrogen. The reaction mixture was quenched with water (200 ml) and extracted with EtOAc (3×200 ml). The organic layers were combined and washed with 2M sodium bisulfite solution (400 ml), water (400 ml), brine (400 ml) dried over MgSO$_4$ and then evaporated. The residue was triturated with Et$_2$O to afford (R)-4-(2-chloro-6-(iodomethyl)pyrimidin-4-yl)-3-methylmorpholine (13.89 g, 66%); $^1$H NMR (400 MHz, CDCl$_3$) 1.32 (3H, d), 3.28 (1H, td), 3.54 (1H, td), 3.69 (1H, dd), 3.78 (1H, d), 3.98-4.02 (2H, m), 4.21 (2H, s), 4.29 (1H, br s), 6.41 (1H, s); m/z: (ESI+) MH$^+$, 354.31.

The mother liquors were concentrated down and triturated with Et$_2$O to afford a further crop of (R)-4-(2-chloro-6-(iodomethyl)pyrimidin-4-yl)-3-methylmorpholine (2.46 g, 12%); $^1$H NMR (400 MHz, CDCl$_3$) 1.32 (3H, d), 3.28 (1H, td), 3.54 (1H, td), 3.69 (1H, dd), 3.78 (1H, d), 3.98-4.02 (2H, m), 4.21 (2H, s), 4.30 (1H, s), 6.41 (1H, s); m/z: (ESI+) MH$^+$, 354.31.

Alternatively, this step can be carried out as follows: (R)-(2-Chloro-6-(3-methylmorpholino)pyrimidin-4-yl)methyl methanesulfonate (80 g, 248.62 mmol) and lithium iodide (83 g, 621.54 mmol) were dissolved in dioxane (300 ml) and then heated at 107° C. for 1 hour. The reaction mixture was quenched with water (250 ml), extracted with EtOAc (3×250 ml), the organic layer was dried over MgSO4, filtered and evaporated. The residue was dissolved in DCM and Et2O was added, the mixture was passed through silica (4 inches) and eluted with Et$_2$O. Fractions containing product were evaporated and the residue was then triturated with Et$_2$O to give a solid which was collected by filtration and dried under vacuum to afford (R)-4-(2-chloro-6-(iodomethyl)pyrimidin-4-yl)-3-methylmorpholine (75 g, 86%); m/z: (ESI+) MH$^+$, 354.27.

e) (R)-4-(2-Chloro-6-(iodomethyl)pyrimidin-4-yl)-3-methylmorpholine (17.0 g, 48.08 mmol) was dissolved in DMF (150 ml), to this was added sodium methanethiolate (3.37 g, 48.08 mmol) and the reaction was stirred for 1 hour at 25° C. The reaction mixture was quenched with water (50 ml) and then extracted with Et$_2$O (3×50 ml). The organic layer was dried over MgSO$_4$, filtered and then evaporated. The residue was purified by flash chromatography on silica, eluting with a gradient of 50 to 100% EtOAc in iso-hexane. Pure fractions were evaporated to afford (R)-4-(2-chloro-6-(methylthiomethyl)pyrimidin-4-yl)-3-methylmorpholine (12.63 g, 96%); m/z: (ES+) MH$^+$, 274.35.

Alternatively, (R)-4-(2-chloro-6-(methylthiomethyl)pyrimidin-4-yl)-3-methylmorpholine, may be prepared as follows: In a 3 L fixed vessel, sodium thiomethoxide (21% in water) (216 g, 646.69 mmol) was added dropwise over 5 minutes to a stirred solution of a mixture of approximately two thirds (R)-(2-chloro-6-(3-methylmorpholino)pyrimidin-4-yl)methyl methanesulfonate and one third (R)-4-(2-chloro-6-(chloromethyl)pyrimidin-4-yl)-3-methylmorpholine (130.2 g, 431 mmol) and sodium iodide (1.762 ml, 43.11 mmol) in MeCN (1 L) at RT (temperature dropped from 20° C. to 18° C. over the addition and then in the next 5 minutes rose to 30° C.). The reaction mixture was stirred for 16 hours and then diluted with EtOAc (2 L), and washed sequentially with water (750 ml) and saturated brine (1 L). The organic layer was dried over MgSO$_4$, filtered and then evaporated to afford (R)-4-(2-chloro-6-(methylthiomethyl)pyrimidin-4-yl)-3-methylmorpholine (108 g, 91%); $^1$H NMR (400 MHz, DMSO-d$_6$) 1.20 (3H, d), 2.07 (3H, s), 3.11-3.26 (1H, m), 3.44 (1H, td), 3.53 (2H, s), 3.59 (1H, dd), 3.71 (1H, d), 3.92 (1H, dd), 3.92-4.04 (1H, br s), 4.33 (1H, s), 6.77 (1H, s); m/z: (ES+) MH$^+$, 274.36.

f) (R)-4-(2-Chloro-6-(methylthiomethyl)pyrimidin-4-yl)-3-methylmorpholine (12.63 g, 46.13 mmol) was dissolved in DCM (100 ml), to this was added mCPBA (7.96 g, 46.13 mmol) in one portion and the reaction mixture was stirred for 10 minutes at 25° C. An additional portion of mCPBA (0.180 g) was added. The reaction mixture was quenched with saturated Na$_2$CO$_3$ solution (50 ml) and extracted with DCM (3×50 ml). The organic layer was dried over MgSO$_4$, filtered and then evaporated. The residue was dissolved in DCM (80 ml) in a 150 ml conical flask which was placed into a beaker containing Et$_2$O (200 ml) and the system covered with laboratory film and then left for 3 days. The obtained crystals were filtered, crushed and sonicated with Et$_2$O. The crystallisation procedure was repeated to afford (R)-4-(2-chloro-6-((R)-methylsulfinylmethyl)pyrimidin-4-yl)-3-methylmorpholine as white needles (3.87 g, 29%); $^1$H NMR (400 MHz, CDCl$_3$) 1.33 (3H, d), 2.62 (3H, s), 3.30 (1H, td), 3.53 (1H, td), 3.68 (1H, dd), 3.76 (2H, dd), 3.95 (1H, d), 4.00 (1H, dd), 4.02 (1H, s), 4.32 (1H, s), 6.42 (1H, s).

The remaining liquor from the first vapour diffusion was purified by flash chromatography on silica, eluting with a gradient of 0 to 5% MeOH in DCM. Pure fractions were evaporated to afford (R)-4-(2-chloro-6-((S)-methylsulfinylmethyl)pyrimidin-4-yl)-3-methylmorpholine as an orange gum (5.70 g, 43%); $^1$H NMR (400 MHz, CDCl$_3$) 1.33 (3H, d), 2.62 (3H, d), 3.29 (1H, td), 3.54 (1H, td), 3.68 (1H, dd), 3.73-3.82 (2H, m), 3.94 (1H, dd), 4.00 (2H, dd), 4.33 (1H, s), 6.42 (1H, s).

Alternatively, this step can be carried out as follows: Sodium meta-periodate (64.7 g, 302.69 mmol) was added in one portion to (R)-4-(2-chloro-6-(methylthiomethyl)pyrimidin-4-yl)-3-methylmorpholine (82.87 g, 302.69 mmol) in water (500 ml), EtOAc (1000 ml) and MeOH (500 ml). The resulting solution was stirred at 20° C. for 16 hours. Sodium metabisulfite (50 g) was added and the mixture stirred for 30 minutes. The reaction mixture was filtered and then partially evaporated to remove the MeOH. The organic layer was separated, dried over MgSO$_4$, filtered and then evaporated. The aqueous layer was washed with DCM (3×500 ml). The organic layers were combined, dried over MgSO$_4$, filtered and then evaporated. The residues were combined and dissolved in DCM (400 ml) and purified by flash chromatography on silica, eluting with a gradient of 0 to 5% MeOH in DCM. Fractions containing product were evaporated and the residue was dissolved in DCM (400 ml) and then divided into four 450 ml bottles. An aluminium foil cap was placed over the top of each bottle and a few holes made in each cap. The bottles were placed in pairs in a large dish containing Et$_2$O (1000 ml), and then covered and sealed with a second glass dish and left for 11 days. The resultant white needles were collected by filtration and dried under vacuum. The crystals were dissolved in DCM (200 ml) and placed into a 450 ml bottle. An aluminium foil cap was placed over the top of the bottle and a few holes made in the cap. The bottle was placed in a large dish containing Et$_2$O (1500 ml) and then covered and sealed with a second glass dish and left for 6 days. The resultant crystals were collected by filtration and dried under vacuum to afford (R)-4-(2-chloro-6-((R)-methylsulfinylmethyl)pyrimidin-4-yl)-3-methylmorpholine (16.53 g, 19%); $^1$H NMR (400 MHz, CDCl$_3$) 1.33 (3H, d), 2.61 (3H, s), 3.29 (1H, td), 3.53 (1H, td), 3.68 (1H, dd), 3.76 (2H, dd), 3.95 (1H, d), 3.99 (1H, dd), 4.02 (1H, s), 4.31 (1H, s), 6.41 (1H, s). Chiral HPLC: (HP1100 System 5, 20 μm Chiralpak AD-H (250 mm×4.6 mm) column eluting with Hexane/EtOH/TEA 50/50/0.1) Rf, 12.192 98.2%.

The filtrate from the first vapour diffusion was concentrated in vacuo to afford an approximate 5:2 mixture of (R)-4-(2-chloro-6-((S)-methylsulfinylmethyl)pyrimidin-4-yl)-3-methylmorpholine and (R)-4-(2-chloro-6-((R)-methylsulfinylmethyl)pyrimidin-4-yl)-3-methylmorpholine (54.7 g, 62%).

Alternatively, this step can be carried out as follows: Sodium meta-periodate (2.87 g, 13.44 mmol) was added in one portion to (R)-4-(2-chloro-6-(methylthiomethyl)pyrimidin-4-yl)-3-methylmorpholine (3.68 g, 13.44 mmol) in water (10.00 ml), EtOAc (20 ml) and MeOH (10.00 ml). The resulting solution was stirred at 20° C. for 16 hours. The reaction mixture was diluted with DCM (60 ml) and then filtered. The DCM layer was separated and the aqueous layer washed with DCM (3×40 ml). The organics were combined, dried over MgSO$_4$, filtered and then evaporated. The residue was purified by flash chromatography on silica, eluting with a gradient of 0 to 7% MeOH in DCM. Pure fractions were evaporated to afford (R)-4-(2-chloro-6-(methylsulfinylmethyl)pyrimidin-4-yl)-3-methylmorpholine (2.72 g, 70%); $^1$H NMR (400 MHz, DMSO-d$_6$) 1.22 (3H, d), 2.64 (3H, d), 3.14-3.26 (1H, m), 3.45 (1H, td), 3.59 (1H, dd), 3.73 (1H, d), 3.88-3.96 (2H, m), 4.00 (1H, d), 4.07 (1H, dt), 4.33 (1H, s), 6.81 (1H, s); m/z: (ESI+) MH$^+$, 290.43.

The (3R)-4-(2-chloro-6-(methylsulfinylmethyl)pyrimidin-4-yl)-3-methylmorpholine (2.7 g, 9.32 mmol) was purified by preparative chiral chromatography on a Merck 100 mm 20 μm Chiralpak AD column, eluting isocratically with a 50:50:0.1 mixture of iso-Hexane:EtOH:TEA as eluent. The fractions containing product were evaporated to afford (R)-4-(2-chloro-6-((S)-methylsulfinylmethyl)pyrimidin-4-yl)-3-methylmorpholine (1.38 g, 51%) as the first eluting compound; $^1$H NMR (400 MHz, CDCl$_3$) 1.29 (3H, dd), 2.56 (3H, s), 3.15-3.33 (1H, m), 3.46 (1H, tt), 3.55-3.83 (3H, m), 3.85-4.06 (3H, m), 4.31 (1H, s), 6.37 (1H, s). Chiral HPLC: (HP1100 System 6, 20 μm Chiralpak AD (250 mm×4.6 mm) column eluting with iso-Hexane/EtOH/TEA 50/50/0.1) Rf, 7.197 >99%.

and (R)-4-(2-chloro-6-((R)-methylsulfinylmethyl)pyrimidin-4-yl)-3-methylmorpholine (1.27 g, 47%) as the second eluting compound; $^1$H NMR (400 MHz, CDCl$_3$) 1.28 (3H, d), 2.58 (3H, s), 3.26 (1H, td), 3.48 (1H, td), 3.62 (1H, dt), 3.77 (2H, dd), 3.88-4.13 (3H, m), 4.28 (1H, s), 6.37 (1H, s). Chiral HPLC: (HP1100 System 6, 20 μm Chiralpak AD (250 mm×4.6 mm) column eluting with iso-Hexane/EtOH/TEA 50/50/0.1) Rf, 16.897 >99%.

g) Iodobenzene diacetate (18.98 g, 58.94 mmol) was added to (R)-4-(2-chloro-6-((R)-methylsulfinylmethyl)pyrimidin-4-yl)-3-methylmorpholine (17.08 g, 58.94 mmol), 2,2,2-trifluoroacetamide (13.33 g, 117.88 mmol), magnesium oxide (9.50 g, 235.76 mmol) and rhodium(II) acetate dimer (0.651 g, 1.47 mmol) in DCM (589 ml) under air. The resulting suspension was stirred at 20° C. for 24 hours. Further 2,2,2-trifluoroacetamide (13.33 g, 117.88 mmol), magnesium oxide (9.50 g, 235.76 mmol), iodobenzene diacetate (18.98 g, 58.94 mmol) and rhodium(II) acetate dimer (0.651 g, 1.47 mmol) were added and the suspension was stirred at 20° C. for 3 days. The reaction mixture was filtered and then silica gel (100 g) added to the filtrate and the solvent removed in vacuo. The resulting powder was purified by flash chromatography on silica, eluting with a gradient of 20 to 50% EtOAc in isohexane. Pure fractions were evaporated to afford N-[({2-chloro-6-[(3R)-3-methylmorpholin-4-yl]pyrimidin-4-yl}methyl)(methyl)oxido-λ6-(R)-sulfanylidene]-2,2,2-trifluoroacetamide (19.39 g, 82%); $^1$H NMR (400 MHz, DMSO-d$_6$) 1.22 (3H, d), 3.17-3.27 (1H, m), 3.44 (1H, td), 3.59 (1H, dd), 3.62 (3H, s), 3.74 (1H, d), 3.95 (1H, dd), 4.04 (1H, br s), 4.28 (1H, s), 5.08 (2H, q), 6.96 (1H, s); m/z: (ESI+) MH$^+$, 401.12 and 403.13.

h) Dichlorobis(triphenylphosphine)palladium(II) (8.10 mg, 0.01 mmol) was added in one portion to N-[({2-chloro-6-[(3R)-3-methylmorpholin-4-yl]pyrimidin-4-yl}methyl)(methyl)oxido-λ6-(R)-sulfanylidene]-2,2,2-trifluoroacetamide (185 mg, 0.46 mmol), 2M aqueous Na$_2$CO$_3$ solution (0.277 ml, 0.55 mmol) and 4-(4,4,5,5-tetramethyl-1,3,2-dioxaborolan-2-yl)-1-tosyl-1H-pyrrolo[2,3-b]pyridine (193 mg, 0.48 mmol) in DME:water 4:1 (5 ml) at RT. The reaction mixture was stirred at 90° C. for 1 hour, filtered and then purified by preparative HPLC using decreasingly polar mixtures of water (containing 1% NH$_3$) and MeCN as eluents. Fractions containing the desired compound were evaporated to afford (R)-3-methyl-4-(6-((R)—S-methylsulfonimidoylmethyl)-2-(1-tosyl-1H-pyrrolo[2,3-b]pyridin-4-yl)pyrimidin-4-yl) morpholine (102 mg, 41%); $^1$H NMR (400 MHz, CDCl$_3$) 1.33 (3H, d), 3.21-3.38 (1H, m), 3.42 (3H, d), 3.45-3.57 (1H, m), 3.61-3.70 (1H, m), 3.78 (1H, d), 4.01 (1H, dd), 3.90-4.15 (1H, br s), 4.30 (1H, s), 4.64 (1H, dd), 4.84 (1H, dd), 6.49 (1H, d); m/z: (ESI+) MH$^+$, 541.35

The 4-(4,4,5,5-tetramethyl-1,3,2-dioxaborolan-2-yl)-1-tosyl-1H-pyrrolo[2,3-b]pyridine, used as starting material, can be prepared as follows:

a) To a 3 L fixed vessel was charged 3-chlorobenzoperoxoic acid (324 g, 1444.67 mmol) portionwise to 1H-pyrrolo[2,3-b]pyridine (150 g, 1244.33 mmol) in DME (750 ml) and heptane (1500 ml) at 20° C. over a period of 1 hour under nitrogen. The resulting slurry was stirred at 20° C. for 18 hours. The precipitate was collected by filtration, washed with DME/heptane (1/2 5 vol) (750 ml) and dried under vacuum at 40° C. to afford 1H-pyrrolo[2,3-b]pyridine 7-oxide 3-chlorobenzoate (353 g, 97%) as a cream solid, which was used without further purification; $^1$H NMR (400 MHz, DMSO-d$_6$) 6.59 (1H, d), 7.07 (1H, dd), 7.45 (1H, d), 7.55 (1H, t), 7.65 (1H, dd), 7.70 (1H, ddd), 7.87-7.93 (2H, m), 8.13 (1H, d), 12.42 (1H, s), 13.32 (1H, s).

b) A 2M solution of potassium carbonate (910 ml, 1819.39 mmol) was added dropwise to a stirred slurry of 1H-pyrrolo[2,3-b]pyridine 7-oxide 3-chlorobenzoate (352.6 g, 1212.93 mmol) in water (4.2 vol) (1481 ml) at 20° C., over a period of 1 hour adjusting the pH to 10. To the resulting slurry was charged water (2 vol) (705 ml) stirred at 20° C. for 1 hour. The slurry was cooled to 0° C. for 1 hour and the slurry filtered, the solid was washed with water (3 vol 1050 ml) and dried in a vacuum oven at 40° C. over P$_2$O$_5$ overnight to afford 1H-pyrrolo[2,3-b]pyridine 7-oxide (118 g, 73%); $^1$H NMR (400 MHz, DMSO-d$_6$) 6.58 (1H, d), 7.06 (1H, dd), 7.45 (1H, d), 7.64 (1H, d), 8.13 (1H, d), 12.44 (1H, s); m/z: (ES+) (MH+MeCN)$^+$, 176.03.

c) To a 3 L fixed vessel under an atmosphere of nitrogen was charged methanesulfonic anhydride (363 g, 2042.71 mmol) portionwise to 1H-pyrrolo[2,3-b]pyridine 7-oxide (137 g, 1021.36 mmol), and tetramethylammonium bromide (236 g, 1532.03 mmol) in DMF (10 vol) (1370 ml) cooled to 0° C. over a period of 30 minutes under nitrogen. The resulting suspension was stirred at 20° C. for 24 hours. The reaction mixture was quenched with water (20 vol, 2740 ml) and the reaction mixture was adjusted to pH 7 with 50% sodium hydroxide (approx 200 ml). Water (40 vol, 5480 ml) was charged and the mixture cooled to 10° C. for 30 minutes. The solid was filtered, washed with water (20 vol, 2740 ml) and the solid dissolved into DCM/methanol (4:1, 2000 ml), dried over MgSO$_4$ and evaporated to provide a light brown solid. The solid was taken up in hot methanol (2000 ml) and water added dropwise until the solution went turbid and left overnight. The solid was filtered off and discarded, the solution was evaporated and the solid recrystallised from MeCN (4000 ml). The solid was filtered and washed with MeCN (4000 ml) to afford 4-bromo-1H-pyrrolo[2,3-b]pyridine (68.4 g, 34%) as a pink solid; $^1$H NMR (400 MHz, DMSO-d$_6$) 6.40-6.45 (1H, m), 7.33 (1H, d), 7.57-7.63 (1H, m), 8.09 (1H, t), 12.02 (1H, s); m/z: (ES+) MH$^+$, 198.92. The crude mother liquors were purified by Companion RF (reverse phase C18, 415 g column), using decreasingly polar mixtures of water (containing 1% NH$_3$) and MeCN as eluents (starting at 26% upto 46% MeCN). Fractions containing the desired compound were evaporated to afford 4-bromo-1H-pyrrolo[2,3-b]pyridine (5.4 g, 3%) as a pink solid; $^1$H NMR (400 MHz, DMSO-d$_6$) 6.43 (1H, dd), 7.33 (1H, d), 7.55-7.66 (1H, m), 8.09 (1H, d), 12.03 (1H, s); m/z: (ES+) MH$^+$, 199.22.

d) Sodium hydroxide (31.4 ml, 188.35 mmol) was added to 4-bromo-1H-pyrrolo[2,3-b]pyridine (10.03 g, 50.91 mmol), tosyl chloride (19.41 g, 101.81 mmol) and tetrabutylammonium hydrogensulfate (0.519 g, 1.53 mmol) in DCM (250 ml) at RT. The resulting mixture was stirred at RT for 1 hour. The reaction was quenched through the addition of saturated aqueous $NH_4Cl$, the organic layer removed and the aqueous layer further extracted with DCM (3×25 ml). The combined organics were washed with brine (100 ml), dried over $Na_2SO_4$ and then concentrated under reduced pressure. The residue was purified by flash chromatography on silica, eluting with a gradient of 0 to 20% EtOAc in isohexane. Pure fractions were evaporated to afford 4-bromo-1-tosyl-1H-pyrrolo[2,3-b]pyridine (14.50 g, 81%); $^1$H NMR (400 MHz, $CDCl_3$) 2.38 (3H, s), 6.64 (1H, d), 7.28 (2H, d), 7.36 (1H, d), 7.78 (1H, d), 8.06 (2H, d), 8.22 (1H, d); m/z: (ES+) $MH^+$, 353.23.

e) 1,1'-Bis(diphenylphosphino)ferrocenedichloropalladium (II) (3.37 g, 4.13 mmol) was added in one portion to 4-bromo-1-tosyl-1H-pyrrolo[2,3-b]pyridine (14.5 g, 41.28 mmol), bis(pinacolato)diboron (20.97 g, 82.57 mmol) and potassium acetate (12.16 g, 123.85 mmol) in anhydrous DMF (300 ml) at RT. The resulting mixture was stirred under nitrogen at 90° C. for 24 hours. After cooling to RT, 1N aqueous NaOH was added until the aqueous layer was taken to pH 10. The aqueous layer was washed with DCM (1 L), carefully acidified to pH 4 with 1 N aqueous HCl, and then extracted with DCM (3×300 ml). The organic layer was concentrated under reduced pressure to afford a dark brown solid. The solid was triturated with diethyl ether, filtered and dried to afford 4-(4,4,5,5-tetramethyl-1,3,2-dioxaborolan-2-yl)-1-tosyl-1H-pyrrolo[2,3-b]pyridine (7.058 g, 43%); $^1$H NMR (400 MHz, $CDCl_3$) 1.36 (12H, s), 2.35 (3H, s), 7.01 (1H, d), 7.22 (2H, d), 7.52 (1H, d), 7.74 (1H, d), 8.03 (2H, m), 8.42 (1H, d); m/z: (ES+) $MH^+$, 399.40. The mother liquors were concentrated in vacuo and the residue triturated in isohexane, filtered and dried to afford a further sample of 4-(4,4,5,5-tetramethyl-1,3,2-dioxaborolan-2-yl)-1-tosyl-1H-pyrrolo[2,3-b]pyridine (3.173 g, 19%); $^1$H NMR (400 MHz, $CDCl_3$) 1.36 (12H, s), 2.35 (3H, s), 7.01 (1H, d), 7.23 (2H, d), 7.52 (1H, d), 7.74 (1H, d), 8.03 (2H, d), 8.42 (1H, d); m/z: (ES+) $MH^+$, 399.40.

EXAMPLE 2.01 AND EXAMPLE 2.02

4-{4-[(3R)-3-Methylmorpholin-4-yl]-6-[1-((S)—S-methylsulfonimidoyl)cyclopropyl]pyrimidin-2-yl}-1H-pyrrolo[2,3-b]pyridine, and 4-{4-[(3R)-3-Methylmorpholin-4-yl]-6-[1-((R)—S-methylsulfonimidoyl)cyclopropyl]pyrimidin-2-yl}-1H-pyrrolo[2,3-b]pyridine

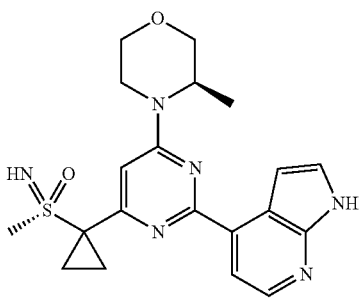

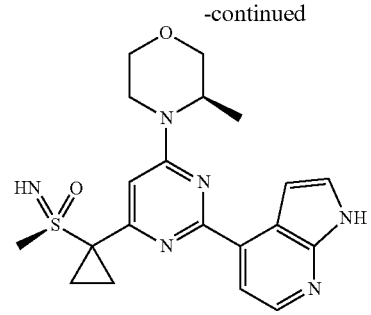

(3R)-3-Methyl-4-(6-(1-(S-methylsulfonimidoyl)cyclopropyl)-2-(1-tosyl-1H-pyrrolo[2,3-b]pyridin-4-yl)pyrimidin-4-yl)morpholine (1.67 g, 2.95 mmol) was dissolved in DME:water 4:1 (60 ml) and heated to 50° C. Sodium hydroxide, 2M aqueous solution (2.58 ml, 5.16 mmol) was then added and heating continued for 18 hours. The reaction mixture was acidified with 2M HCl (~2 ml) to pH5. The reaction mixture was evaporated to dryness and the residue dissolved in EtOAc (250 ml), and washed with water (200 ml). The organic layer was dried over $MgSO_4$, filtered and evaporated onto silica gel (10 g). The resulting powder was purified by flash chromatography on silica, eluting with a gradient of 0 to 7% MeOH in DCM. Pure fractions were evaporated and the residue was purified by preparative chiral chromatography on a Merck 50 mm, 20 µm ChiralCel OJ column, eluting isocratically with 50% isohexane in EtOH/MeOH (1:1) (modified with TEA) as eluent. The fractions containing the desired compound were evaporated to dryness to afford the title compound: 4-{4-[(3R)-3-methylmorpholin-4-yl]-6-[1-((R)—S-methylsulfonimidoyl)cyclopropyl]pyrimidin-2-yl}-1H-pyrrolo[2,3-b]pyridine (0.538 g, 44%) as the first eluting compound; $^1$H NMR (400 MHz, DMSO-$d^6$) 1.29 (3H, d), 1.51 (3H, m), 1.70-1.82 (1H, m), 3.11 (3H, s), 3.28 (1H, m, obscured by water peak), 3.48-3.60 (1H, m), 3.68 (1H, dd), 3.75-3.87 (2H, m), 4.02 (1H, dd), 4.19 (1H, d), 4.60 (1H, s), 7.01 (1H, s), 7.23 (1H, dd), 7.51-7.67 (1H, m), 7.95 (1H, d), 8.34 (1H, d), 11.76 (1H, s); m/z: (ES+) $MH^+$, 413.12. Chiral HPLC: (HP1100 System 4, 5 µm Chiralcel OJ-H (250 mm×4.6 mm) column eluting with iso-Hexane/EtOH/MeOH/TEA 50/25/25/0.1) Rf, 9.013 >99%. Crystals were grown and isolated by slow evaporation to dryness in air from EtOAc. These crystals were used to obtain the structure shown in FIG. 1 by X-Ray diffraction (see below). Example 2.02: 4-{4-[(3R)-3-methylmorpholin-4-yl]-6-[1-((R)—S-methylsulfonimidoyl)cyclopropyl]pyrimidin-2-yl}-1H-pyrrolo[2,3-b]pyridine (326 mg, 0.79 mmol) was dissolved in DCM (3 ml). Silica gel (0.5 g) was added and the mixture concentrated in vacuo. The resulting powder was purified by flash chromatography on silica, eluting with a gradient of 0 to 5% MeOH in DCM. Pure fractions were evaporated to dryness and the residue was crystallized from EtOAc/n-heptane to afford 4-{4-[(3R)-3-methylmorpholin-4-yl]-6-[1-((R)—S-methylsulfonimidoyl)cyclopropyl]pyrimidin-2-yl}-1H-pyrrolo[2,3-b]pyridine (256 mg, 79%) as a white crystalline solid; $^1$H NMR (400 MHz, DMSO-$d^6$) 1.29 (3H, d), 1.39-1.60 (3H, m), 1.71-1.81 (1H, m), 3.10 (3H, d), 3.21-3.29 (1H, m), 3.52 (1H, td), 3.67 (1H, dd), 3.80 (2H, t), 4.01 (1H, dd), 4.19 (1H, d), 4.59 (1H, s), 7.01 (1H, s), 7.23 (1H, dd), 7.54-7.62 (1H, m), 7.95 (1H, d), 8.34 (1H, d), 11.75 (1H, s). DSC (Mettler-Toledo DSC 820, sample run at a heating rate of 10° C. per minute from 30° C. to 350° C. in a pierced aluminium pan) peak, 224.11° C.

and the title compound: 4-{4-[(3R)-3-methylmorpholin-4-yl]-6-[1-((S)—S-methylsulfonimidoyl)cyclopropyl]pyrimidin-2-yl}-1H-pyrrolo[2,3-b]pyridine (0.441 g, 36%) as the second eluting compound; $^1$H NMR (400 MHz, DMSO-$d^6$)

1.28 (3H, d), 1.40-1.58 (3H, m), 1.70-1.80 (1H, m), 3.10 (3H, d), 3.23-3.27 (1H, m), 3.51 (1H, dt), 3.66 (1H, dd), 3.80 (2H, d), 4.01 (1H, dd), 4.21 (1H, d), 4.56 (1H, s), 6.99 (1H, s), 7.22 (1H, dd), 7.54-7.61 (1H, m), 7.94 (1H, d), 8.33 (1H, d), 11.75 (1H, s); m/z: (ES+) MH$^+$, 413.12. Chiral HPLC: (HP1100 System 4, 5 μm Chiralcel OJ-H (250 mm×4.6 mm) column eluting with iso-Hexane/EtOH/MeOH/TEA 50/25/25/0.1) Rf, 15.685 >99%. Example 2.01: 4-{4-[(3R)-3-methylmorpholin-4-yl]-6-[1-((S)—S-methylsulfonimidoyl)cyclopropyl]pyrimidin-2-yl}-1H-pyrrolo[2,3-b]pyridine (66.5 mg) was purified by crystallisation from EtOH/water to afford 4-{4-[(3R)-3-methylmorpholin-4-yl]-6-[1-((S)—S-methylsulfonimidoyl)cyclopropyl]pyrimidin-2-yl}-1H-pyrrolo[2,3-b]pyridine (0.050 g); $^1$H NMR (400 MHz, CDCl$_3$) 1.40 (3H, d), 1.59 (2H, s), 1.81 (2H, s), 2.41 (1H, s), 3.16 (3H, s), 3.39 (1H, td), 3.59-3.67 (1H, m), 3.77 (1H, dd), 3.86 (1H, d), 4.07 (1H, dd), 4.17 (1H, d), 4.54 (1H, s), 6.91 (1H, s), 7.34 (1H, t), 7.43 (1H, t), 8.05 (1H, d), 8.41 (1H, d), 9.14 (1H, s).

| X-Ray Diffraction on crystal from first eluted compound (Structure shown in Figure 1) | |
| --- | --- |
| Crystal data | |
| C$_{20}$H$_{24}$N$_6$O$_2$S | V = 1026.4 (2) Å$^3$ |
| Mr = 412.52 | P1 Z = 2 |
| Triclinic, | Mo Kα radiation, λ = 0.71073 Å |
| a = 10.1755 (13) Å | μ = 0.19 mm-1 |
| b = 10.4411 (13) Å | T = 200K |
| c = 11.2879 (14) Å | 0.20 × 0.10 × 0.05 mm |
| α = 95.528 (2)° | |
| β = 108.796 (2)° | |
| γ = 111.292 (2)° | |
| Data collection | |
| Bruker APEX-II CCD diffractometer | 14550 independent reflections |
| Absorption correction: Multi-scan | 18381 measured reflections |
| 9935 reflections with I > 2σ(I) | |
| Tmin = 0.964, Tmax = 0.991 Rint = 0.024 | |
| Refinement | |
| R[F$^2$ > 2σ(F$^2$)] = 0.056 | H-atom parameters constrained |
| wR(F$^2$) = 0.147 | Δρmax = 0.31 e Å$^{-3}$ |
| S = 1.02 | Δρmin = -0.38 e Å$^{-3}$ |
| 14550 reflections | |
| Absolute structure: Flack H D (1983), Acta Cryst.A39, 876-881 (5) | Flack parameter: 0.03 |
| 527 parameters | |
| 3 restraints | |

The (3R)-3-methyl-4-(6-(1-(S-methylsulfonimidoyl)cyclopropyl)-2-(1-tosyl-1H-pyrrolo[2,3-b]pyridin-4-yl)pyrimidin-4-yl)morpholine, used as starting material, can be prepared as follows:

a) Iodobenzene diacetate (6.54 g, 20.29 mmol) was added to (3R)-4-(2-chloro-6-(methylsulfinylmethyl)pyrimidin-4-yl)-3-methylmorpholine (5.88 g, 20.29 mmol), 2,2,2-trifluoroacetamide (4.59 g, 40.58 mmol), magnesium oxide (3.27 g, 81.16 mmol) and rhodium(II) acetate dimer (0.224 g, 0.51 mmol) in DCM (169 ml) under air. The resulting suspension was stirred at RT for 3 days. Further 2,2,2-trifluoroacetamide (1.15 g, 10.15 mmol), magnesium oxide (0.818 g, 20.29 mmol), rhodium(II) acetate dimer (0.056 g, 0.13 mmol) and iodobenzene diacetate (1.64 g, 5.07 mmol) were added and the suspension was stirred at RT for a further 24 hours. The reaction mixture was filtered and silica gel (3 g) was added to the filtrate and then the mixture was evaporated. The resulting powder was purified by flash chromatography on silica, eluting with a gradient of 20 to 50% EtOAc in isohexane. Fractions containing product were evaporated and the residue was triturated with isohexane/methyl tert-butylether to give a solid which was collected by filtration and dried under vacuum to afford N-[({2-chloro-6-[(3R)-3-methylmorpholin-4-yl]pyrimidin-4-yl}methyl)(methyl)oxido-λ6-sulfanylidene]-2,2,2-trifluoroacetamide (6.64 g, 82%); $^1$H NMR (400 MHz, CDCl$_3$) 1.33 (3H, d), 3.28 (1H, dd), 3.43 (3H, d), 3.46-3.59 (1H, m), 3.62-3.71 (1H, m), 3.79 (1H, d), 3.90-4.50 (2H, br s), 4.21 (1H, s), 4.66 (1H, dd), 4.86 (1H, dd), 6.50 (1H, d); m/z: (ES+) MH 401.01, 402.93.

b) Sodium hydroxide (Sigma-Aldrich 415413, d=1.515 g/ml, 50 ml of a 50% solution, 937.57 mmol) was added to N-[({2-chloro-6-[(3R)-3-methylmorpholin-4-yl]pyrimidin-4-yl}methyl)(methyl)oxido-λ6-sulfanylidene]-2,2,2-trifluoroacetamide (5.2 g, 12.97 mmol), 1,2-dibromoethane (4.47 ml, 51.90 mmol) and tetrabutylammonium hydrogensulfate (0.441 g, 1.30 mmol) in toluene (500 ml). The resulting mixture was stirred at RT for 24 hours. Further 1,2-dibromoethane (1.00 ml, 11.60 mmol) was added and the mixture was stirred at RT for a further 2 hours. The reaction mixture was diluted with EtOAc (500 ml), and washed sequentially with water (750 ml) and saturated brine (100 ml). The organic layer was dried over MgSO$_4$, filtered and evaporated. The residue was dissolved in DCM (100 ml) and then purified by flash chromatography on silica, eluting with a gradient of 0 to 5% MeOH in DCM. Pure fractions were evaporated to dryness to afford (3R)-4-(2-chloro-6-(1-(S-methylsulfonimidoyl)cyclopropyl)pyrimidin-4-yl)-3-methylmorpholine (1.383 g, 32%); $^1$H NMR (400 MHz, CDCl$_3$) 1.32 (3H, d), 1.39-1.48 (2H, m), 1.69-1.77 (2H, m), 3.12 (3H, s), 3.22-3.36 (1H, m), 3.54 (1H, td), 3.68 (1H, dd), 3.78 (1H, d), 3.90-4.10 (1H, br s), 4.00 (1H, dd), 4.33 (1H, br s), 6.79 (1H, d); m/z: (ES+) MH$^+$, 331.08, 333.00.

Alternatively, this step can be performed as follows:
Sodium hydroxide (Sigma-Aldrich 415413, d=1.515 g/ml, 217 ml of a 50% solution, 4059.84 mmol) was added to N-[({2-chloro-6-[(3R)-3-methylmorpholin-4-yl]pyrimidin-4-yl}methyl)(methyl)oxido-λ6-sulfanylidene]-2,2,2-trifluoroacetamide (27.12 g, 67.66 mmol), 1,2-dibromoethane (23.32 ml, 270.66 mmol) and tetraoctylammonium bromide (3.70 g, 6.77 mmol) in methyl THF (1000 ml) at 20° C. under nitrogen. The resulting mixture was stirred at 20° C. for 24 hours. Further 1,2-dibromoethane (23.32 ml, 270.66 mmol) was added and the mixture was stirred at 20° C. for a further 24 hours. The reaction mixture was diluted with methyl THF (1000 ml) and the aqueous layer separated. The organic layer was diluted further with EtOAc (1000 ml) and washed with water (1500 ml). The organic layer was dried over MgSO$_4$, filtered and then evaporated. The residue was purified by flash chromatography on silica, eluting with a gradient of 0 to 5% MeOH in DCM. Pure fractions were evaporated to afford (3R)-4-(2-chloro-6-(1-(S-methylsulfonimidoyl)cyclopropyl)pyrimidin-4-yl)-3-methylmorpholine (14.80 g, 66%); $^1$H NMR (400 MHz, DMSO-d$^6$) 1.21 (3H, d), 1.39 (3H, m), 1.62-1.71 (1H, m), 3.01 (3H, s), 3.43 (1H, tt), 3.58 (1H, dd), 3.72 (1H, d), 3.82 (1H, d), 3.93 (1H, dd), 4.01 (1H, s), 4.38 (1H, s), 6.96 (1H, d); m/z: (ES+) MH$^+$, 331.46 and 333.43.

d) Dichlorobis(triphenylphosphine)palladium(II) (0.073 g, 0.10 mmol) was added in one portion to (3R)-4-(2-chloro-6-(1-(S-methylsulfonimidoyl)cyclopropyl)pyrimidin-4-yl)-3-methylmorpholine (1.383 g, 4.18 mmol), 2M aqueous sodium carbonate solution (2.508 ml, 5.02 mmol) and 4-(4,4,5,5-tetramethyl-1,3,2-dioxaborolan-2-yl)-1-tosyl-1H-pyrrolo[2,3-b]pyridine (1.665 g, 4.18 mmol) in DME:water 4:1 (100 ml) under nitrogen. The reaction mixture was stirred at 90° C. for 6 hours. The reaction mixture was concentrated and diluted with EtOAc (400 ml), and washed sequentially with water (300 ml) and saturated brine (75 ml). The organic layer was dried over MgSO₄, filtered and evaporated onto silica gel (30 g). The resulting powder was purified by flash chromatography on silica, eluting with a gradient of 0 to 5% MeOH in DCM. Pure fractions were evaporated to dryness to afford (3R)-3-methyl-4-(6-(1-(S-methylsulfonimidoyl)cyclopropyl)-2-(1-tosyl-1H-pyrrolo[2,3-b]pyridin-4-yl)pyrimidin-4-yl)morpholine (2.174 g, 92%); $^1$H NMR (400 MHz, CDCl₃) 1.37 (3H, d), 1.56 (2H, m), 1.83 (2H, q), 2.37 (4H, s), 3.16 (3H, s), 3.36 (1H, td), 3.60 (1H, td), 3.74 (1H, dd), 3.85 (1H, d), 4.01-4.19 (2H, m), 4.49 (1H, s), 6.95 (1H, d), 7.28 (2H, d, obscured by CDCL3 peak), 7.44 (1H, t), 7.82 (1H, d), 8.02-8.11 (3H, m), 8.52 (1H, d); m/z: (ES+) MH⁺, 567.11.

Alternatively, example 2.01 and example 2.02, may be prepared as follows:

Sodium hydroxide, 2M aqueous solution (9.95 ml, 19.90 mmol) was added to (3R)-3-methyl-4-(6-(1-(S-methylsulfonimidoyl)cyclopropyl)-2-(1-tosyl-1H-pyrrolo[2,3-b]pyridin-4-yl)pyrimidin-4-yl)morpholine (6.44 g, 11.37 mmol) in DME (100 ml)/water (25.00 ml). The resulting solution was stirred at 50° C. for 18 hours. Further NaOH, 2M aqueous solution (18 ml, 36.00 mmol) was added and the mixture was stirred at 50° C. for a further 3 days. The reaction mixture was acidified with 2M HCl (~22 ml) to pH5. The reaction mixture was evaporated and the residue was dissolved in DCM (250 ml) and washed with water (200 ml). The organic layer was dried over MgSO₄, filtered and then evaporated to approximately 50 ml in volume. The solution was purified by flash chromatography on silica, eluting with a gradient of 0 to 7% MeOH in DCM. Pure fractions were evaporated to afford 4-{4-[(3R)-3-methylmorpholin-4-yl]-6-[1-(S-methylsulfonimidoyl)cyclopropyl]pyrimidin-2-yl}-1H-pyrrolo[2,3-b]pyridine (2.440 g, 52%); $^1$H NMR (400 MHz, DMSO-d⁶) 1.27 (3H, d), 1.42 (1H, dd), 1.47-1.58 (2H, m), 1.68-1.80 (1H, m), 3.10 (3H, s), 3.24-3.31 (1H, m), 3.51 (1H, t), 3.66 (1H, dd), 3.80 (1H, d), 3.83-3.88 (1H, m), 4.00 (1H, dd), 4.20 (1H, s), 4.57 (1H, s), 6.99 (1H, d), 7.22 (1H, dd), 7.53-7.63 (1H, m), 7.94 (1H, d), 8.34 (1H, t), 11.80 (1H, s); m/z: (ES+) MH⁺, 413.47.

In a separate experiment, NaOH, 2M aqueous solution (7.60 ml, 15.19 mmol) was added to (3R)-3-methyl-4-(6-(1-(S-methylsulfonimidoyl)cyclopropyl)-2-(1-tosyl-1H-pyrrolo[2,3-b]pyridin-4-yl)pyrimidin-4-yl)morpholine (4.92 g, 8.68 mmol) in DME (100 ml)/water (25.00 ml). The resulting solution was stirred at 50° C. for 18 hours. The reaction mixture was acidified with 2M HCl (~5 mL) to pH5. The reaction mixture was evaporated and the residue was dissolved in DCM (250 ml) and washed with water (200 ml). The organic layer was dried over MgSO₄, filtered and then evaporated to approximately 50 ml in volume. The resulting solution was purified by flash chromatography on silica, eluting with a gradient of 0 to 7% MeOH in DCM. Pure fractions were evaporated to dryness to afford 4-{4-[(3R)-3-methylmorpholin-4-yl]-6-[1-(S-methylsulfonimidoyl)cyclopropyl]pyrimidin-2-yl}-1H-pyrrolo[2,3-b]pyridine (2.160 g, 60%); $^1$H NMR (400 MHz, DMSO-d⁶) 1.28 (3H, d), 1.41-1.59 (3H, m), 1.76 (1H, dt), 3.10 (3H, d), 3.31 (1H, d), 3.52 (1H, t), 3.67 (1H, dd), 3.80 (2H, d), 4.01 (1H, dd), 4.21 (1H, d), 4.58 (1H, s), 7.00 (1H, d), 7.22 (1H, dd), 7.54-7.63 (1H, m), 7.95 (1H, d), 8.33 (1H, d), 11.75 (1H, s); m/z: (ES+) MH⁺, 413.19.

The two samples of 4-{4-[(3R)-3-methylmorpholin-4-yl]-6-[1-(S-methylsulfonimidoyl)cyclopropyl]pyrimidin-2-yl}-1H-pyrrolo[2,3-b]pyridine were combined (4.56 g, 11.05 mmol) and purified by preparative chiral chromatography on a Merck 100 mm ChiralCel OJ column (1550 g), eluting isocratically with 50% isohexane in EtOH/MeOH (1:1) (modified with TEA) as eluent. The fractions containing the first eluting compound were combined and evaporated. The residue was dissolved in DCM (50 ml) and concentrated in vacuo onto silica (20 g). The resulting powder was purified by flash chromatography on silica, eluting with a gradient of 0 to 7% MeOH in DCM. Pure fractions were evaporated to afford the title compound 4-{4-[(3R)-3-methylmorpholin-4-yl]-6-[1-((R)—S-methylsulfonimidoyl)cyclopropyl]pyrimidin-2-yl}-1H-pyrrolo[2,3-b]pyridine (1.789 g, 39%); $^1$H NMR (400 MHz, DMSO-d⁶) 1.27 (3H, d), 1.43 (1H, dd), 1.46-1.58 (2H, m), 1.69-1.77 (1H, m), 3.10 (3H, s), 3.27 (1H, td), 3.51 (1H, td), 3.66 (1H, dd), 3.80 (1H, d), 3.85 (1H, s), 4.01 (1H, dd), 4.19 (1H, d), 4.59 (1H, s), 6.99 (1H, s), 7.22 (1H, dd), 7.54-7.63 (1H, m), 7.94 (1H, d), 8.33 (1H, d), 11.80 (1H, s); m/z: (ES+) MH⁺, 413.50. Chiral HPLC: (Kronlab prep system, 20 μm Chiralpak OJ (250 mm×4.6 mm) column eluting with Hexane/EtOH/MeOH/TEA 50/25/25/0.1) Rf, 9.684 99.4%.

The fractions containing the second eluting compound were combined and evaporated. The residue was dissolved in DCM (50 ml) and concentrated in vacuo onto silica gel (20 g). The resulting powder was purified by flash<autotext key="0CA02197" name="[AP-silica/alumina]" type="lookup" length="6"/> chromatography on silica, eluting with a gradient of 0<autotext key="0CA02198" name="[AP-Num Purification]" type="lookup" length="1"/> to 7<autotext key="0CA02199" name="[AP-Num Purification]" type="lookup" length="1"/>% MeOH<autotext key="0CA0219A" name="[AP-Solvents]" type="lookup" length="4"/> in DCM<autotext key="0CA0219B" name="[AP-Solvents]" type="lookup" length="3"/>. Pure fractions were evaporated to afford the title compound 4-{4-[(3R)-3-Methylmorpholin-4-yl]-6-[1-((S)—S-methylsulfonimidoyl)cyclopropyl]pyrimidin-2-yl}-1H-pyrrolo[2,3-b]pyridine (2.85 g, 62%); $^1$H NMR (400 MHz, DMSO-d⁶) 1.27 (3H, d), 1.38-1.46 (1H, dd), 1.51 (2H, m), 1.72-1.81 (1H, m), 3.10 (3H, s), 3.26 (1H, td), 3.51 (1H, td), 3.66 (1H, dd), 3.80 (1H, d), 3.84 (1H, s), 3.94-4.04 (1H, dd), 4.21 (1H, d), 4.56 (1H, s), 6.99 (1H, s), 7.22 (1H, dd), 7.53-7.63 (1H, m), 7.94 (1H, d), 8.33 (1H, d), 11.80 (1H, s); m/z: (ES+) MH⁺, 413.53. Chiral HPLC: (Kronlab prep system, 20 μm Chiralpak OJ (250 mm×4.6 mm) column eluting with Hexane/EtOH/MeOH/TEA 50/25/25/0.1) Rf, 18.287 99.3%.

Example 2.02 can also be prepared as follows:
Dichlorobis(triphenylphosphine)palladium(II) (2.59 mg, 3.69 μmol) was added in one portion to (3R)-4-(2-chloro-6-(1-((R)—S-methylsulfonimidoyl)cyclopropyl)pyrimidin-4-yl)-3-methylmorpholine (63 mg, 0.15 mmol), 2M aqueous Na2CO3 solution (0.089 ml, 0.18 mmol) and 4-(4,4,5,5-tetramethyl-1,3,2-dioxaborolan-2-yl)-1-tosyl-1H-pyrrolo[2,3-b]pyridine (58.8 mg, 0.15 mmol) in DME:water 4:1 (5 ml) at RT. The reaction mixture was stirred at 90° C. for 4 hours. Sodium hydroxide, 2M aqueous solution (0.131 ml, 0.26 mmol) was added and the mixture was heated at 50° C. for 18 hours. The reaction mixture was acidified with 2M HCl to pH7. The reaction mixture was filtered and then purified by preparative HPLC using decreasingly polar mixtures of water (containing 1% NH₃) and MeCN as eluents. Pure fractions were evaporated and the residue triturated with isohexane and Et₂O to give a solid which was collected by filtration and dried under vacuum to afford the title compound (44.0 mg, 71%); $^1$H NMR (400 MHz, DMSO-d⁶) 1.29 (3H, d), 1.40-1.61 (3H, m), 1.70-1.81 (1H, m), 3.10 (3H, s), 3.53 (1H, dd), 3.68 (1H, dd), 3.77-3.87 (2H, m), 4.02 (1H, dd), 4.19 (1H, d), 4.58 (1H, s), 7.01 (1H, d), 7.23 (1H, dd), 7.55-7.61 (1H, m), 7.95 (1H, d), 8.34 (1H, d), 11.75 (1H, s).; m/z: (ES+) MH⁺, 413.19. Chiral HPLC: (HP1100 System 4, 5 μm Chiralcel OJ-H (250 mm×4.6 mm) column eluting with iso-Hexane/EtOH/MeOH/TEA 50/25/25/0.1) Rf, 9.023 88.0%, 15.796 12.0%.

The (3R)-4-(2-chloro-6-(1-((R)—S-methylsulfonimidoyl)cyclopropyl)pyrimidin-4-yl)-3-methylmorpholine, used as starting material, can be prepared as follows:
Sodium hydroxide (Sigma-Aldrich 415413, d=1.515 g/ml, 155 ml of a 50% solution, 2902.66 mmol) was added to N-[({2-chloro-6-[(3R)-3-methylmorpholin-4-yl]pyrimidin-4-yl}methyl)(methyl)oxido-λ6-(R)-sulfanylidene]-2,2,2-trifluoroacetamide (19.39 g, 48.38 mmol), 1,2-dibromoethane (16.68 mL, 193.51 mmol) and tetraoctylammonium bromide (2.65 g, 4.84 mmol) in methyl THF (1000 ml) at 20° C. under nitrogen. The resulting mixture was stirred at 20° C. for 24 hours. The reaction mixture was diluted with methyl THF (1000 ml) and the aqueous layer separated. The organic layer was diluted further with EtOAc (1000 ml) and then washed with water (1500 ml). The organic layer was dried over $MgSO_4$, filtered and evaporated. The residue was purified by flash chromatography on silica, eluting with a gradient of 0 to 5% MeOH in DCM. Pure fractions were evaporated to dryness to afford (3R)-4-(2-chloro-6-(1-((R)—S-methylsulfonimidoyl)cyclopropyl)pyrimidin-4-yl)-3-methylmorpholine (6.88 g, 43%); $^1$H NMR (400 MHz, $CDCl_3$) 1.32 (3H, d), 1.43 (2H, q), 1.72 (2H, q), 2.35 (1H, s), 3.09 (3H, s), 3.29 (1H, td), 3.53 (1H, td), 3.67 (1H, dd), 3.78 (1H, d), 4.00 (2H, dd), 4.32 (1H, s), 6.79 (1H, s); m/z: (ES+) $MH^+$, 331.18 and 333.15.

Example 2.02 can also be prepared as follows:
2M NaOH solution (14.86 ml, 29.72 mmol) was added to (3R)-3-methyl-4-(6-(1-((R)—S-methylsulfonimidoyl)cyclopropyl)-2-(1-tosyl-1H-pyrrolo[2,3-b]pyridin-4-yl)pyrimidin-4-yl)morpholine (8.42 g, 14.86 mmol) in DME:water 4:1 (134 ml). The resulting solution was stirred at RT for 4 days. In a separate experiment, 2M NaOH solution (7.06 ml, 14.12 mmol) was added to (3R)-3-methyl-4-(6-(1-((R)—S-methylsulfonimidoyl)cyclopropyl)-2-(1-tosyl-1H-pyrrolo[2,3-b]pyridin-4-yl)pyrimidin-4-yl)morpholine (4 g, 7.06 mmol) in DME:water 4:1 (63.5 ml). The resulting solution was stirred at RT for 18 hours. The reaction mixtures from the two procedures were combined and then neutralised with 2M HCl. The mixture was evaporated onto reverse phase silica gel (40 g) and the resulting powder was purified by flash chromatography on reverse phase silica, eluting with a gradient of 20 to 60% ACN in water with 1% ammonia. Pure fractions were evaporated to dryness to afford the title compound (7.05 g, 78%); $^1$H NMR (400 MHz, DMSO-$d^6$) 1.27 (3H, t), 1.39-1.6 (3H, m), 1.7-1.8 (1H, m), 3.10 (3H, s), 3.26 (1H, d), 3.52 (1H, td), 3.67 (1H, dd), 3.80 (2H, t), 3.97-4.02 (1H, m), 4.19 (1H, d), 4.59 (1H, s), 7.00 (1H, s), 7.22 (1H, dd), 7.53-7.61 (1H, m), 7.95 (1H, d), 8.33 (1H, d), 11.75 (1H, s); m/z: (ES+) $MH^+$, 413.08.

The (3R)-3-methyl-4-(6-(1-((R)—S-methylsulfonimidoyl)cyclopropyl)-2-(1-tosyl-1H-pyrrolo[2,3-b]pyridin-4-yl)pyrimidin-4-yl)morpholine, used as starting material, can be prepared as follows:
a) A solution of 4-(4,4,5,5-tetramethyl-1,3,2-dioxaborolan-2-yl)-1-tosyl-1H-pyrrolo[2,3-b]pyridine (21.15 g, 53.11 mmol) in DME (212 ml) was added to a solution of (3R)-4-(2-chloro-6-(1-((R)—S-methylsulfonimidoyl)cyclopropyl)pyrimidin-4-yl)-3-methylmorpholine (12.55 g, 37.93 mmol) in DME:water 4:1 (55 ml). 2M aqueous sodium carbonate solution (22.76 ml, 45.52 mmol) and dichlorobis(triphenylphosphine)palladium(II) (0.666 g, 0.95 mmol) were added. The resulting solution was stirred at 90° C. for 2 hours under nitrogen. The reaction mixture was diluted with EtOAc (400 ml), and washed with water (400 ml). The organic layer was dried over MgSO4, filtered and evaporated. The residue was dissolved in DCM (100 ml) and a portion was purified by flash chromatography on silica eluting with a gradient of 0 to 5% MeOH in DCM. Pure fractions were evaporated to afford (3R)-3-methyl-4-(6-(1-((R)—S-methylsulfonimidoyl)cyclopropyl)-2-(1-tosyl-1H-pyrrolo[2,3-b]pyridin-4-yl)pyrimidin-4-yl)morpholine (8.42 g, 39%); $^1$H NMR (400 MHz, $CDCl_3$) 1.36 (3H, d), 1.52 (2H, dd), 1.80 (2H, dd), 2.24-2.46 (3H, s), 3.10 (3H, s), 3.36 (1H, td), 3.60 (1H, td), 3.74 (1H, dd), 3.84 (1H, d), 3.99-4.18 (2H, m), 4.47 (1H, s), 6.91 (1H, s), 7.23-7.3 (3H, m, obscured by $CDCl_3$), 7.45 (1H, d), 7.81 (1H, d), 8.08 (3H, dd), 8.51 (1H, d); m/z: (ES+) $MH^+$, 567.4. The rest of the material was evaporated and the residue was dissolved in DCM (500 ml) and concentrated in vacuo onto silica (100 g). The resulting powder was purified by flash chromatography on silica, eluting with a gradient of 0 to 5% MeOH in DCM. Pure fractions were evaporated to dryness to afford (3R)-3-methyl-4-(6-(1-((R)—S-methylsulfonimidoyl)cyclopropyl)-2-(1-tosyl-1H-pyrrolo[2,3-b]pyridin-4-yl)pyrimidin-4-yl)morpholine (4.00 g, 19%); $^1$H NMR (400 MHz, DMSO-$d^6$) 1.19-1.31 (3H, m), 1.37-1.58 (3H, m), 1.75 (1H, ddd), 2.34 (3H, s), 3.04 (3H, d), 3.2-3.27 (1H, m), 3.46-3.54 (1H, m), 3.65 (1H, dd), 3.78 (1H, d), 3.82 (1H, s), 3.99 (1H, dd), 4.16 (1H, d), 4.54 (1H, s), 7.04 (1H, s), 7.42 (2H, d), 7.54 (1H, d), 8.01 (3H, dd), 8.10 (1H, d), 8.49 (1H, d); m/z: (ES+) $MH^+$, 567.00.

Example 2.02 can also be prepared as follows:
2M NaOH solution (0.2 ml, 0.40 mmol) was added to (3R)-3-methyl-4-(6-(1-((R)—S-methylsulfonimidoyl)cyclopropyl)-2-(1-tosyl-1H-pyrrolo[2,3-b]pyridin-4-yl)pyrimidin-4-yl)morpholine (0.107 g, 0.19 mmol) in DME:water 4:1 (4 ml). The resulting solution was stirred at 50° C. for 18 hours and then further 2M NaOH solution (0.2 ml, 0.40 mmol) was added and the solution was stirred at 50° C. for 3 hours. The reaction mixture was evaporated to dryness and the residue dissolved in DCM (10 ml), and then washed with water (10 ml). The organic layer was dried over $MgSO_4$, filtered and then evaporated. The residue was purified by preparative HPLC (Waters SunFire column, 5μ silica, 19 mm diameter, 100 mm length), using decreasingly polar mixtures of water (containing 0.1% formic acid) and MeCN as eluents. Fractions containing the desired compound were evaporated to dryness to afford the title compound (0.026 g, 30%) as the formate salt; $^1$H NMR (400 MHz, DMSO-$d^6$) 1.28 (3H, d), 1.38-1.47 (1H, m), 1.47-1.57 (2H, m), 1.75 (1H, dd), 3.11 (1H, s), 3.28 (1H, dd), 3.52 (1H, dd), 3.67 (1H, dd), 3.81 (1H, d), 3.98-4.04 (1H, m), 4.18 (1H, s), 4.58 (1H, s), 7.00 (1H, s), 7.22 (1H, d), 7.59 (1H, d), 7.95 (1H, d), 8.34 (1H, d), 8.41 (3H, s), 11.83 (1H, s); m/z: (ES+) $MH^+$, 413.11.

Example 2.02 can also be prepared as follows:
Dichlorobis(triphenylphosphine)palladium(II) (0.061 g, 0.09 mmol) was added to (3R)-4-(2-chloro-6-(1-((R)—S-methylsulfonimidoyl)cyclopropyl)pyrimidin-4-yl)-3-methylmorpholine (1.15 g, 3.48 mmol), 2M sodium carbonate solution (6.95 ml, 13.90 mmol) and 1H-pyrrolo[2,3-b]pyridin-4-ylboronic acid (1.877 g, 3.48 mmol) under nitrogen. The resulting solution was stirred at 85° C. for 6 hours. The reaction mixture was diluted with EtOAc (200 ml), and washed sequentially with water (200 ml) and saturated brine (100 ml). The organic layer was dried over $MgSO_4$, filtered and then evaporated onto silica gel (10 g). The resulting powder was purified by flash chromatography on silica, eluting with a gradient of 0 to 5% MeOH in DCM. Pure fractions were evaporated to afford the title compound (0.660 g, 46%); $^1$H NMR (400 MHz, $CDCl_3$) 1.39 (3H, d), 1.53-1.61 (2H, m), 1.78-1.84 (2H, m), 2.43 (1H, s), 3.16 (3H, s), 3.39 (1H, td), 3.63 (1H, td), 3.77 (1H, dd), 3.86 (1H, d), 4.07 (1H, dd), 4.17 (1H, d), 4.53 (1H, s), 6.92 (1H, s), 7.34 (1H, dd), 7.41-7.47 (1H, m), 8.06 (1H, d), 8.43 (1H, d), 9.60 (1H, s); m/z: (ES+) MH⁺, 413.12. Chiral HPLC: (HP1100 System 4, 5 μm Chiralcel OJ-H (250 mm×4.6 mm) column eluting with Heptane/EtOH/MeOH/TEA 50/25/25/0.1) Rf, 8.113 98.9%.

The 1H-pyrrolo[2,3-b]pyridin-4-ylboronic acid, used as starting material, may be prepared as follows:

4-Bromo-1H-pyrrolo[2,3-b]pyridine (0.944 g, 4.79 mmol) in THF (10 ml) was added dropwise to sodium hydride (0.240 g, 5.99 mmol) in THF (10 ml) at 20'C under nitrogen. The resulting mixture was stirred at 20° C. for 10 minutes. The reaction mixture was cooled to −78° C. and n-butyllithium in hexanes (2.396 mL, 5.99 mmol) was added dropwise over 10 minutes and stirred at −78° C. for 10 minutes. Triisopropyl borate (3.32 mL, 14.37 mmol) was added dropwise over 2 minutes and the reaction mixture allowed to warm to RT over 1.5 hours. The reaction mixture was quenched with water (10 ml) and C18 silica gel was added (10 g) and the mixture was concentrated in vacuo. The resultant solid was purified by reverse phase flash silica chromatography, eluting with a gradient of 5 to 40% acetonitrile in water. Pure fractions were evaporated to afford 1H-pyrrolo[2,3-b]pyridin-4-ylboronic acid (0.590 g, 76%); m/z: (ES+) MH⁺, 162.88.

Example 2.02 can also be prepared as follows:
4-{4-[(3R)-3-Methylmorpholin-4-yl]-6-[1-((R)—S-methylsulfonimidoyl)cyclopropyl]pyrimidin-2-yl}-1H-pyrrolo[2,3-b]pyridine (approximately 10 g, 25 mmol) was suspended in MTBE (500 ml) and stirred at reflux for 2 hours. The suspension was allowed to cool slowly and stirred at RT overnight. The solid was collected by filtration and dried under vacuum to afford the title compound (7.12 g) as a white crystalline solid; ¹H NMR (400 MHz, DMSO-d⁶) 1.28 (3H, d), 1.44 (1H, dd), 1.47-1.58 (2H, m), 1.76 (1H, dt), 3.11 (3H, s), 3.26 (1H, dd), 3.52 (1H, td), 3.67 (1H, dd), 3.81 (1H, d), 3.85 (1H, d), 4.02 (1H, dd), 4.20 (1H, d), 4.59 (1H, s), 7.00 (1H, s), 7.23 (1H, dd), 7.57-7.62 (1H, m), 7.95 (1H, d), 8.34 (1H, d), 11.81 (1H, s); m/z: (ES+) MH⁺, 413.12. Mpt. (Buchi Melting Point B-545) 222° C. Chiral HPLC: (HP1100 System 7, 5 μm Chiralcel OJ (250 mm×4.6 mm) column eluting with Heptane/(EtOH/MeOH 50/50)/TEA 50/50/0.1) Rf, 9.836 99.8%.

EXAMPLE 2.03 AND EXAMPLE 2.04

N-Methyl-1-{4-[(3R)-3-methylmorpholin-4-yl]-6-[1-((R)—S-methylsulfonimidoyl)cyclopropyl]pyrimidin-2-yl}-1H-benzimidazol-2-amine and N-Methyl-1-{4-[(3R)-3-methylmorpholin-4-yl]-6-[1-((S)—S-methylsulfonimidoyl)cyclopropyl]pyrimidin-2-yl}-1H-benzimidazol-2-amine

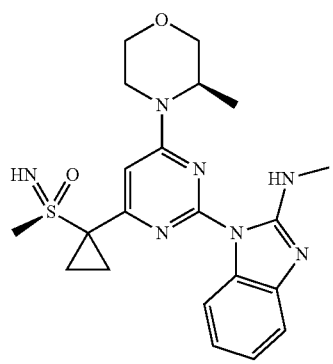

-continued

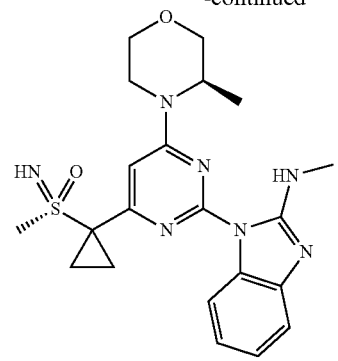

Cesium carbonate (942 mg, 2.89 mmol) was added to (3R)-4-(2-chloro-6-(1-(S-methylsulfonimidoyl)cyclopropyl)pyrimidin-4-yl)-3-methylmorpholine (319 mg, 0.96 mmol) and N-methyl-1H-benzo[d]imidazol-2-amine (284 mg, 1.93 mmol) in DMA (10 ml). The resulting suspension was stirred at 80° C. for 45 hours. A further portion of N-methyl-1H-benzo[d]imidazol-2-amine (284 mg, 1.93 mmol), cesium carbonate (942 mg, 2.89 mmol) and sodium methanesulfinate (98 mg, 0.96 mmol) were added and the suspension was stirred at 80° C. for 70 hours. The reaction mixture was filtered and then evaporated. The residue was dissolved in EtOAc (250 ml), and washed sequentially with water (250 ml) and saturated brine (75 ml). The organic layer was dried over MgSO₄, filtered and evaporated onto silica gel (5 g). The resulting powder was purified by flash chromatography on silica, eluting with a gradient of 0 to 5% MeOH in DCM. Pure fractions were evaporated and the residue was purified by preparative chiral chromatography on a Merck 50 mm, 20 μm Chiralpak AS column, eluting isocratically with 70% isohexane in IPA (modified with Et3N) as eluent. The fractions containing the desired compound were evaporated to afford the title compound: N-Methyl-1-{4-[(3R)-3-methylmorpholin-4-yl]-6-[1-((R)—S-methylsulfonimidoyl)cyclopropyl]pyrimidin-2-yl}-1H-benzimidazol-2-amine (166 mg, 39%) as the first eluting compound; ¹H NMR (400 MHz, DMSO-d⁶) 1.29 (3H, d), 1.47 (2H, dq), 1.55-1.66 (1H, m), 1.69-1.89 (1H, m), 3.01 (3H, s), 3.04 (3H, d), 3.30-3.39 (1H, m), 3.52 (1H, td), 3.66 (1H, dd), 3.80 (1H, d), 3.95 (1H, s), 4.01 (1H, dd), 4.09 (1H, d), 4.51 (1H, s), 6.77 (1H, s), 6.97 (1H, t), 7.08 (1H, t), 7.25 (1H, d), 8.08 (1H, d), 8.67 (1H, d); m/z: (ES+) MH⁺, 442.09. Chiral HPLC: (HP1100 System 4, 20 μm Chiralpak AS (250 mm×4.6 mm) column eluting with iso-Hexane/IPA/TEA 70/30/0.1) Rf, 12.219 >99%.

and the title compound: N-Methyl-1-{4-[(3R)-3-methylmorpholin-4-yl]-6-[1-((S)—S-methylsulfonimidoyl)cyclopropyl]pyrimidin-2-yl}-1H-benzimidazol-2-amine (123 mg, 29%) as the second eluting compound; ¹H NMR (400 MHz, DMSO-d⁶) 1.33 (3H, t), 1.45-1.61 (2H, m), 1.61-1.68 (1H, m), 1.80-1.89 (1H, m), 3.07 (3H, s), 3.09 (3H, d), 3.39 (1H, dd), 3.58 (1H, td), 3.72 (1H, dd), 3.86 (1H, d), 4.01 (1H, s), 4.06 (1H, dd), 4.15 (1H, d), 4.55 (1H, s), 6.82 (1H, s), 7.03 (1H, t), 7.14 (1H, t), 7.31 (1H, d), 8.14 (1H, d), 8.73 (1H, d); m/z: (ES+) MH⁺, 442.09. Chiral HPLC: (HP1100 System 4, 20 μm Chiralpak AS (250 mm×4.6 mm) column eluting with iso-Hexane/IPA/TEA 70/30/0.1) Rf, 25.093 >99%.

Example 2.03 can also be prepared as follows:
(3R)-4-(2-Chloro-6-(1-((R)—S-methylsulfonimidoyl)cyclopropyl)pyrimidin-4-yl)-3-methylmorpholine (179 mg, 0.54 mmol), N-methyl-1H-benzo[d]imidazol-2-amine (159 mg, 1.08 mmol) and cesium carbonate (529 mg, 1.62 mmol) were suspended in DMA (2 ml) and sealed into a microwave tube. The reaction mixture was heated to 80° C. for 90 minutes in a microwave reactor and then cooled to RT. The reaction mixture was filtered and then purified by preparative HPLC, using decreasingly polar mixtures of water (containing 1% NH₃) and MeCN as eluents. Fractions containing the desired compound were evaporated to afford a solid (55.0 mg). In an additional procedure: (R)-4-(2-Chloro-6-(1-((R)—S-methylsulfonimidoyl)cyclopropyl)pyrimidin-4-yl)-3-methylmorpholine (89 mg, 0.27 mmol), N-methyl-1H-benzo[d]imidazol-2-amine (79 mg, 0.54 mmol) and cesium carbonate (263 mg, 0.81 mmol) were suspended in DMA (2 ml) and sealed into a microwave tube. The reaction mixture was heated to 80° C. for 5 hours in a microwave reactor and then cooled to RT. The reaction mixture was filtered, and combined with the solid from the previous procedure and then purified by preparative HPLC using decreasingly polar mixtures of water (containing 1% NH3) and MeCN as eluents. Fractions containing the desired compound were evaporated and the residue was purified by preparative HPLC using decreasingly polar mixtures of water (containing 0.1% formic acid) and MeCN as eluents. Fractions containing the desired compound were evaporated and the residue purified again by preparative HPLC using decreasingly polar mixtures of water (containing 1% NH₃) and MeCN as eluents. Fractions containing the desired compound were evaporated to afford the title compound (38.4 mg, 32%); ¹H NMR (400 MHz, DMSO-d⁶) 1.29 (3H, d), 1.52 (3H, m), 1.72-1.86 (1H, m), 3.02 (3H, s), 3.03 (3H, d), 3.26-3.33 (1H, m), 3.52 (1H, t), 3.66 (1H, d), 3.80 (1H, d), 4.01 (2H, m), 4.12 (1H, s, obscured by methanol peak), 4.51 (1H, s), 6.77 (1H, s), 6.98 (1H, t), 7.09 (1H, t), 7.25 (1H, d), 8.08 (1H, d), 8.71 (1H, d); m/z: (ES+) MH⁺, 442.16. Chiral HPLC: (HP1100 System 4, 20 μm Chiralpak AS (250 mm×4.6 mm) column eluting with iso-Hexane/IPA/TEA 70/30/0.1) Rf, 11.984 97.9%.

The N-methyl-1H-benzo[d]imidazol-2-amine, used as starting material, can be prepared as follows:

2-Chloro-1H-benzo[d]imidazole (20 g, 131.08 mmol) was charged to high pressure autoclave PV10832 (Hastelloy 450 ml) with methylamine (260 mL, 131.08 mmol) and sealed on its trolley and the resulting solution heated to 160° C. in high pressure blast cell 60 for 16 hours. The pressure in the autoclave reached 11 bar. The solvent was removed under reduced pressure to afford a brown oil. EtOH was added and the solvent again removed to afford a brown foam. The foam was dissolved in a minimum of hot acetone. This was then allowed to cool. The resultant solid was filtered affording N-methyl-1H-benzo[d]imidazol-2-amine (9.91 g, 51%); ¹H NMR (400 MHz, DMSO-d⁶) 2.83 (3H, s), 6.87-7.00 (2H, m), 7.05-7.25 (2H, m), 7.49 (1H, s).

EXAMPLE 2.05 AND EXAMPLE 2.06

4-{4-[(3R)-3-Methylmorpholin-4-yl]-6-[1-((R)—S-methylsulfonimidoyl)cyclopropyl]pyrimidin-2-yl}-1H-indole and 4-{4-[(3R)-3-methylmorpholin-4-yl]-6-[1-((S)—S-methylsulfonimidoyl)cyclopropyl]pyrimidin-2-yl}-1H-indole

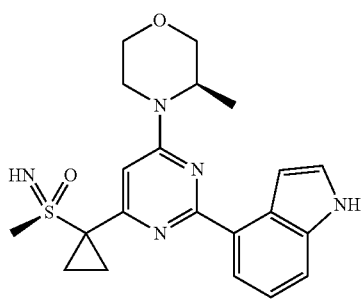

-continued

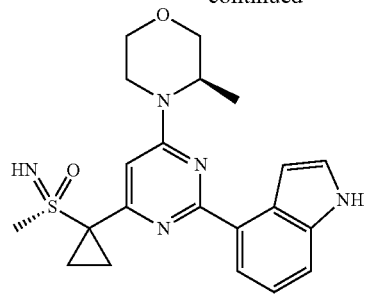

Dichlorobis(triphenylphosphine)palladium(II) (8.49 mg, 0.01 mmol) was added in one portion to (3R)-4-(2-chloro-6-(1-(S-methylsulfonimidoyl)cyclopropyl)pyrimidin-4-yl)-3-methylmorpholine (400 mg, 1.21 mmol), 2M aqueous sodium carbonate solution (0.725 ml, 1.45 mmol) and 1H-indol-4-ylboronic acid (234 mg, 1.45 mmol) in DME:water 4:1 (8.575 ml) and the mixture was sealed into a microwave tube. The reaction mixture was heated to 110° C. for 1 hour in a microwave reactor and then cooled to RT. The mixture was diluted with EtOAc (50 ml) and washed sequentially with water (50 ml) and saturated brine (50 ml). The organic layer was evaporated and the residue was purified by flash chromatography on silica, eluting with a gradient of 0 to 100% EtOAc in DCM. Pure fractions were evaporated and the residue was purified by preparative chiral chromatography on a 20 μm Chiralpak IA (50 mm×250 mm) column, eluting isocratically with a 50:50:0.1 mixture of Hexane:EtOH:TEA as eluent. The fractions containing product were evaporated to afford the title compound: 4-{4-[(3R)-3-methylmorpholin-4-yl]-6-[1-((S)—S-methylsulfonimidoyl)cyclopropyl]pyrimidin-2-yl}-1H-indole (43.8 mg, 24%) as the first eluting compound; ¹H NMR (400 MHz, DMSO-d⁶) 1.33 (3H, d), 1.49 (1H, dd), 1.52-1.63 (2H, m), 1.75-1.84 (1H, m), 3.16 (3H, s), 3.53-3.62 (1H, m), 3.72 (1H, dd), 3.79-3.89 (2H, m), 4.06 (1H, dd), 4.23 (1H, d), 4.65 (1H, s), 6.96 (1H, s), 7.25 (1H, t), 7.37 (1H, s), 7.50 (1H, t), 7.59 (1H, d), 8.09-8.13 (1H, m), 11.27 (1H, s); m/z: (ES+) MH⁺, 412.24. Chiral HPLC: (HP1100 System 4, 20 μm Chiralpak AS (250 mm×4.6 mm) column eluting with Hexane/EtOH/TEA 50/50/0.1) Rf, 8.690 >99%. and the title compound: 4-{4-[(3R)-3-methylmorpholin-4-yl]-6-[1-((R)—S-methylsulfonimidoyl)cyclopropyl]pyrimidin-2-yl}-1H-indole (93.5 mg, 52%) as the second eluting compound; ¹H NMR (400 MHz, DMSO-d⁶) 1.28 (3H, d), 1.41-1.46 (1H, m), 1.50 (2H, td), 1.75 (1H, dd), 3.11 (3H, s), 3.52 (1H, dd), 3.64-3.70 (1H, m), 3.73-3.83 (2H, m), 4.01 (1H, d), 4.20 (1H, d), 4.56 (1H, s), 6.89 (1H, s), 7.19 (1H, t), 7.32 (1H, s), 7.44 (1H, s), 7.53 (1H, d), 8.04-8.08 (1H, m), 11.22 (1H, s); m/z: (ES+) MH⁺, 412.24. Chiral HPLC: (HP1100 System 4, 20 μm Chiralpak AS (250 mm×4.6 mm) column eluting with Hexane/EtOH/TEA 50/50/0.1) Rf, 36.980 >99%.

Example 2.06 can also be prepared as follows:
Dichlorobis(triphenylphosphine)palladium(II) (1.994 mg, 2.84 μmol) was added in one portion to (3R)-4-(2-chloro-6-(1-((S)—S-methylsulfonimidoyl)cyclopropyl)pyrimidin-4-yl)-3-methylmorpholine (0.094 g, 0.28 mmol), 2M aqueous sodium carbonate solution (0.170 ml, 0.34 mmol) and 1H-indol-4-ylboronic acid (0.055 g, 0.34 mmol) in DME:water 4:1 (2.015 ml) and sealed into a microwave tube. The reaction mixture was heated to 110° C. for 1 hour in a microwave reactor and then cooled to RT. The cooled reaction mixture was passed through a PS-Thiol cartridge and then purified by preparative HPLC eluting with decreasingly polar mixtures of water (containing 0.1% formic acid) and MeCN. Fractions containing the product were evaporated and the residue was then purified by ion exchange chromatography, using an SCX column. The desired product was eluted from the column using 2M NH$_3$/MeOH and pure fractions were evaporated to afford the title compound (0.075 g, 64%); $^1$H NMR (400 MHz, DMSO-d$^6$) 1.27 (3H, d), 1.39-1.56 (3H, m), 1.69-1.78 (1H, m), 3.10 (3H, d), 3.52 (1H, td), 3.66 (1H, dd), 3.72-3.83 (2H, m), 4.00 (1H, dd), 4.20 (1H, d), 4.57 (1H, s), 6.89 (1H, d), 7.18 (1H, t), 7.31 (1H, t), 7.43 (1H, t), 7.53 (1H, d), 8.05 (1H, dd), 11.21 (1H, s); m/z: (ES+) MH$^+$, 412.55. Chiral HPLC: (HP1100 System 4, 5 µm Chiralpak AS-H (250 mm×4.6 mm) column eluting with Heptane/EtOH/TEA 50/50/0.1) Rf, 4.511 >99%.

The (3R)-4-(2-chloro-6-(1-((S)—S-methylsulfonimidoyl) cyclopropyl)pyrimidin-4-yl)-3-methylmorpholine, used as starting material, can be prepared as follows:

a) Iodobenzene diacetate (78 g, 243.29 mmol) was added to (3R)-4-(2-chloro-6-((S)-methylsulfinylmethyl)pyrimidin-4-yl)-3-methylmorpholine (70.5 g, 243.29 mmol), 2,2,2-trifluoroacetamide (55.0 g, 486.57 mmol), magnesium oxide (39.2 g, 973.15 mmol) and rhodium(II) acetate dimer (2.69 g, 6.08 mmol) in DCM (2433 ml) under air. The resulting suspension was stirred at 20° C. for 24 hours. Further 2,2,2-trifluoroacetamide (13.75 g, 121.64 mmol), magnesium oxide (9.81 g, 243.29 mmol), iodobenzene diacetate (19.59 g, 60.82 mmol) and rhodium(II) acetate dimer (0.672 g, 1.52 mmol) were added and the suspension was stirred at 20° C. for 1 day. The reaction mixture was filtered and then silica gel (200 g) added to the filtrate and the solvent removed in vacuo. The resulting powder was purified by flash chromatography on silica, eluting with a gradient of 20 to 50% EtOAc in heptane. Pure fractions were concentrated and the resultant precipitate collected by filtration to afford N-[({2-chloro-6-[(3R)-3-methylmorpholin-4-yl]pyrimidin-4-yl}methyl)(methyl)oxido-λ6-sulfanylidene]-2,2,2-trifluoroacetamide as a 7:1 mixture of S:R isomers (26.14 g, 27%); $^1$H NMR (400 MHz, CDCl$_3$) 1.33 (3H, d), 3.28 (1H, dd), 3.42 (3H, d), 3.46-3.57 (1H, m), 3.61-3.70 (1H, m), 3.79 (1H, d), 4.02 (1H, dd), 4.65 (1H, d), 4.85 (1H, dd), 6.49 (1H, d); m/z: (ES+) MH$^+$, 400.94 and 402.85. Chiral HPLC: (HP1100 System 4, 5 µm Chiralpak AD-H (250 mm×4.6 mm) column eluting with Heptane/EtOH 50/50) Rf, 4.367 12.5%, 6.053 87.5%. The mother liquors were concentrated in vacuo to yield a colourless gum. The gum was triturated with isohexane to give a solid which was collected by filtration and dried under vacuum to afford N-[({2-chloro-6-[(3R)-3-methylmorpholin-4-yl]pyrimidin-4-yl}methyl)(methyl)oxido-λ6-sulfanylidene]-2,2,2-trifluoroacetamide as a 2.8:1 mixture of R:S isomers (47.1 g, 48%); $^1$H NMR (400 MHz, CDCl$_3$) 1.33 (3H, d), 3.31 (1H, t), 3.42 (3H, d), 3.47-3.57 (1H, m), 3.62-3.70 (1H, m), 3.79 (1H, d), 4.02 (1H, dd), 4.65 (1H, dd), 4.86 (1H, dd), 6.49 (1H, d); m/z: (ES+) MH$^+$, 400.94 and 402.86. Chiral HPLC: (HP1100 System 4, 5 µm Chiralpak AD-H (250 mm×4.6 mm) column eluting with Heptane/EtOH 50/50) Rf, 4.365 73.5%, 6.067 26.4%.

b) Cesium hydroxide-hydrate (0.390 g, 3.43 mmol) was added to a 7:1 mixture of S:R isomers of N-[({2-chloro-6-[(3R)-3-methylmorpholin-4-yl]pyrimidin-4-yl}methyl)(methyl)oxido-λ6-sulfanylidene]-2,2,2-trifluoroacetamide (0.209 g, 0.69 mmol), 1,2-dibromoethane (0.236 ml, 2.74 mmol) and tetraoctylammonium bromide (0.037 g, 0.07 mmol) in methyl THF (2 ml) at 20° C. under nitrogen. The resulting mixture was stirred at 20° C. for 16 hours. Further 1,2-dibromoethane (0.236 mL, 2.74 mmol) was added and the mixture was stirred at 20° C. for 24 hours. A second portion of cesium hydroxide-hydrate (0.390 g, 3.43 mmol) was added and the mixture stirred over a weekend. The reaction mixture was filtered and silica gel (5 g) added to the filtrate. The mixture was concentrated in vacuo and the resultant powder was then purified by flash chromatography on silica, eluting with a gradient of 0 to 5% MeOH in DCM. Pure fractions were evaporated to afford (3R)-4-(2-chloro-6-(1-((S)—S-methylsulfonimidoyl)cyclopropyl)pyrimidin-4-yl)-3-methylmorpholine (0.099 g, 44%); $^1$H NMR (400 MHz, CDCl$_3$) 1.31 (3H, t), 1.43 (2H, h), 1.67-1.75 (2H, m), 2.33 (1H, s), 3.09 (3H, s), 3.29 (1H, td), 3.53 (1H, td), 3.67 (1H, dd), 3.78 (1H, d), 4.00 (2H, dd+broad s), 4.33 (1H, s), 6.78 (1H, s); m/z: (ES+) MH$^+$, 331.04 and 332.99. Chiral HPLC: (HP1100 System 4, 5 µm Chiralpak AD-H (250 mm×4.6 mm) column eluting with Heptane/IPA/TEA 70/30/0.1) Rf, 5.948 89.5%.

EXAMPLE 2.07 AND EXAMPLE 2.08

1-{4-[(3R)-3-Methylmorpholin-4-yl]-6-[1-((R)—S-methylsulfonimidoyl)cyclopropyl]pyrimidin-2-yl}-1H-benzimidazol-2-amine and 1-{4-[(3R)-3-methylmorpholin-4-yl]-6-[1-((S)—S-methylsulfonimidoyl) cyclopropyl]pyrimidin-2-yl}-1H-benzimidazol-2-amine

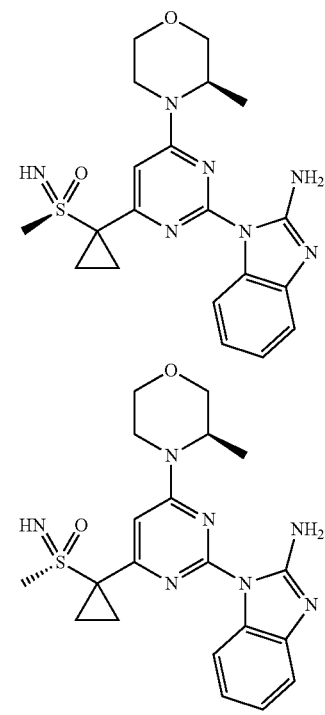

Cesium carbonate (1.773 g, 5.44 mmol) was added to (3R)-4-(2-chloro-6-(1-(S-methylsulfonimidoyl)cyclopropyl)pyrimidin-4-yl)-3-methylmorpholine (0.3 g, 0.91 mmol) and 1H-benzo[d]imidazol-2-amine (0.121 g, 0.91 mmol) in DMA (9.07 ml). The resulting suspension was stirred at 80° C. for 3 days. The reaction mixture was evaporated and the residue was dissolved in EtOAc (500 mL), and the mixture was then washed sequentially with water (400 mL) and saturated brine (100 mL). The aqueous layer was washed with EtOAc (4×500 mL). The organic layers were combined and then dried over MgSO$_4$, filtered and evaporated. The residue was dissolved in DCM (100 mL) and the resulting solution was purified by flash chromatography on silica, eluting with a gradient of 0 to 15% MeOH in DCM. Pure fractions were evaporated and the residue was purified by preparative chiral chromatography on a 20 μm Chiralpak IA (50 mm×250 mm) column, eluting isocratically with 50:50:0.2:0.1 mixture of Hexane:IPA:AcOH:TEA as eluents. Fractions containing product were evaporated to afford the first eluted title compound (0.045 g, 23%); $^1$H NMR (400 MHz, DMSO-d[6]) 1.29 (3H, d), 1.40-1.49 (2H, m), 1.50-1.58 (1H, m), 1.71-1.84 (1H, m), 3.02 (3H, s), 3.52 (1H, t), 3.67 (1H, d), 3.80 (1H, d), 3.93 (1H, s), 4.01 (1H, d), 4.09 (1H, s), 4.48 (1H, s), 6.87 (1H, s), 6.97 (1H, dd), 7.07 (1H, dd), 7.18 (1H, d), 7.65 (2H, s), 8.08 (1H, d); m/z: (ES+) MH+, 428.10. Chiral HPLC: (HP1100 System 3, 20 μm Chiralpak IA (250 mm×4.6 mm) column eluting with Hexane/IPA/AcOH/TEA 50/50/0.2/0.1) Rf, 5.653 93.8%. and the second eluted title compound (0.030 g, 15%); $^1$H NMR (400 MHz, DMSO-d[6]) 1.30 (3H, d), 1.44 (2H, s), 1.50-1.58 (1H, m), 1.72-1.82 (1H, m), 3.01 (3H, s), 3.47-3.57 (1H, m), 3.63-3.70 (1H, m), 3.78 (1H, s), 3.94 (1H, s), 3.97-4.05 (1H, m), 4.04-4.13 (1H, m), 4.43-4.55 (1H, m), 6.88 (1H, s), 6.98 (1H, d), 7.07 (1H, s), 7.18 (1H, d), 7.66 (2H, s), 8.07 (1H, d).; m/z: (ES+) MH+, 428.10. Chiral HPLC: (HP1100 System 4, 20 μm Chiralpak IA (250 mm×4.6 mm) column eluting with Hexane/IPA/AcOH/TEA 50/50/0.2/0.1) Rf, 7.031 96.9%.

EXAMPLE 2.09 AND EXAMPLE 2.10

4-Fluoro-N-methyl-1-{4-[(3R)-3-methylmorpholin-4-yl]-6-[1-((R)—S-methylsulfonimidoyl)cyclopropyl]pyrimidin-2-yl}-1H-benzimidazol-2-amine and 4-fluoro-N-methyl-{4-[(3R)-3-methylmorpholin-4-yl]-6-[1-((S)—S-methylsulfonimidoyl)cyclopropyl]pyrimidin-2-yl}-1H-benzimidazol-2-amine

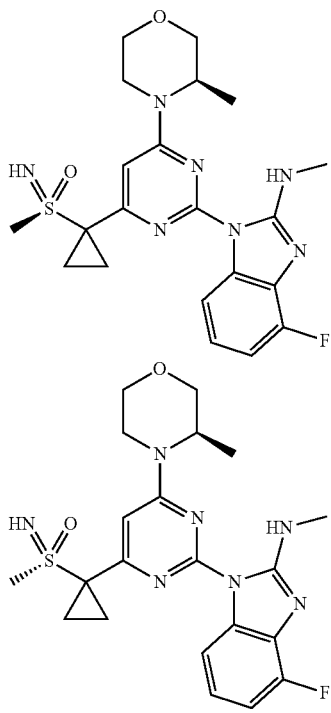

Cesium carbonate (1.891 g, 5.80 mmol) was added to (3R)-4-(2-chloro-6-(1-(S-methylsulfonimidoyl)cyclopropyl)pyrimidin-4-yl)-3-methylmorpholine (0.64 g, 1.93 mmol) and 7-fluoro-N-methyl-1H-benzo[d]imidazol-2-amine (0.639 g, 3.87 mmol) in DMA (20.15 ml). The resulting suspension was stirred at 80° C. for 45 hours. Further portions of 7-fluoro-N-methyl-1H-benzo[d]imidazol-2-amine (0.639 g, 3.87 mmol), cesium carbonate (1.891 g, 5.80 mmol) and sodium methanesulfinate (0.197 g, 1.93 mmol) were added and the suspension was stirred at 80° C. for a further 70 hours. The reaction mixture was filtered and the filtrate was diluted with EtOAc (250 mL) and then washed sequentially with water (250 mL) and saturated brine (75 mL). The organic layer was dried over $MgSO_4$, filtered and then evaporated directly onto silica (5 g). The resulting powder was purified by flash chromatography on silica, eluting with a gradient of 0 to 5% MeOH in DCM. Pure fractions were evaporated and the residue was purified by preparative chiral HPLC on a 20 μm Chiralpak IA (50 mm×250 mm) column eluting with a 50:50:0.2:0.1 mixture of Hexane:IPA:AcOH:TEA as eluents. Fractions containing product were evaporated to afford the first eluting title compound (0.138 g, 16%); $^1$H NMR (400 MHz, DMSO-d[6]) 1.30 (3H, d), 1.50 (2H, dd), 1.60 (1H, d), 1.80 (1H, s), 3.01 (3H, s), 3.06 (3H, d), 3.33 (1H, d), 3.51 (1H, d), 3.66 (1H, d), 3.80 (1H, d), 3.99 (1H, s), 4.02 (1H, s), 4.08 (1H, s), 4.50 (1H, s), 6.79 (1H, s), 6.96 (2H, dd), 7.92 (1H, d), 8.79 (1H, d); m/z: (ES+) MH+, 460.08. Chiral HPLC: (HP1100 System 4, 20 μm Chiralpak AS (250 mm×4.6 mm) column eluting with Heptane/IPA/TEA 70/30/0.1) Rf, 10.697 >99%. and the second eluting title compound (0.183 g, 21%); $^1$H NMR (400 MHz, DMSO-d[6]) 1.29 (3H, d), 1.50 (2H, d), 1.59 (1H, d), 1.79 (1H, s), 3.02 (3H, s), 3.06 (3H, d), 3.33 (1H, d), 3.52 (1H, t), 3.67 (1H, d), 3.80 (1H, d), 3.98 (1H, s), 4.01 (1H, d), 4.08 (1H, s), 4.50 (1H, s), 6.79 (1H, s), 6.96 (2H, dd), 7.92 (1H, d), 8.79 (1H, d); m/z: (ES+) MH+, 460.08. Chiral HPLC: (HP1100 System 4, 20 μm Chiralpak AS (250 mm×4.6 mm) column eluting with Heptane/IPA/TEA 70/30/0.1) Rf, 18.427 99.8%.

The 7-fluoro-N-methyl-1H-benzo[d]imidazol-2-amine, used as starting material, was prepared as follows:
a) 3-Fluorobenzene-1,2-diamine (0.600 g, 4.76 mmol) was dissolved in THF (14.82 ml) and 1,1'-carbonyldiimidazole (0.848 g, 5.23 mmol) was added at RT. The reaction mixture was stirred overnight at RT and then heated for 24 hours at 50° C. The mixture was cooled to RT and ammonia in MeOH (1.5 ml) was added and the mixture stirred for 30 minutes. The mixture was diluted with water (40 ml) and the resultant brown solid was collected by filtration, washed with water and then dried in vacuo to afford 4-fluoro-1H-benzo[d]imidazol-2(3H)-one (0.700 g, 97%) which was used in the next step without further purification; $^1$H NMR (400 MHz, DMSO-d[6]) 6.81 (2H, ddd), 6.88-6.95 (1H, m), 10.82 (1H, s), 11.08 (1H, s); m/z: (ES−) M-H−, 151.19.
b) A solution of 4-fluoro-1H-benzo[d]imidazol-2(3H)-one (0.7 g, 4.60 mmol) in phosphorus oxychloride (14.11 ml, 151.39 mmol) was heated at 100° C. for 18 hours. The reaction mixture was cooled to RT and excess phosphorus oxychloride was evaporated in vacuo. The residue was neutralized slowly (Care: exotherm) with saturated sodium bicarbonate solution (10 ml), and the mixture was then extracted with EtOAc (3×20 ml). The combined organic layers were washed with saturated brine and then dried over Na2SO4, filtered and evaporated to afford 2-chloro-7-fluoro-1H-benzo[d]imidazole (0.740 g, 94%) which was used in the next step without further purification; $^1$H NMR (400 MHz, DMSO-d[6]) 7.01-7.11 (1H, m), 7.23 (1H, td), 7.32 (1H, s), 13.59 (1H, s); m/z: (ES+) MH+, 171.20.
c) 2-Chloro-7-fluoro-1H-benzo[d]imidazole (1.7 g, 9.97 mmol) was charged to a high pressure autoclave PV10832 (Parr 160 ml) with methylamine (40% EtOH solution, 50 ml, 9.97 mmol) and sealed on its trolley and the resulting solution heated to 160° C. in high pressure blast cell 60 for 16 hours. The pressure in the autoclave reached 13 bar. The mixture was evaporated and the residue dissolved in MeOH and then added to an SCX column. The column was eluted with 7N ammonia in MeOH and fractions containing product were evaporated to leave a brown oil. The oil was purified by flash chromatography on silica, eluting with a gradient of 5 to 20% MeOH in DCM. Pure fractions were evaporated to afford 7-fluoro-N-methyl-1H-benzo[d]imidazol-2-amine (1.230 g, 75%); $^1$H NMR (400 MHz, DMSO-d$^6$) 2.88 (3H, d), 6.54 (1H, bs), 6.67-6.73 (1H, m), 6.81 (1H, dd), 6.95 (1H, d); m/z: (ES+) MH$^+$, 166.00.

EXAMPLE 2.11

4-{4-[(3R)-3-Methylmorpholin-4-yl]-6-[1-(S-methylsulfonimidoyl)cyclopropyl]pyrimidin-2-yl}-1H-pyrrolo[2,3-c]pyridine

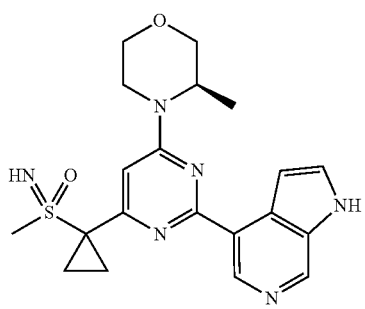 [SMILES: C[C@@H]1COCCN1c1cc(C2(S(C)(=N)=O)CC2)nc(-c2cncc3[nH]ccc23)n1]

Tert-butyl 4-(4-((R)-3-methylmorpholino)-6-(1-(S-methylsulfonimidoyl)cyclopropyl)pyrimidin-2-yl)-1H-pyrrolo[2,3-c]pyridine-1-carboxylate (0.223 g, 0.44 mmol) was added to TFA (5 ml) and DCM (5.00 ml). The resulting solution was stirred at RT for 1 hour. The reaction mixture was evaporated and the residue was purified by preparative HPLC using decreasingly polar mixtures of water (containing 1% NH$_3$) and MeCN as eluents. Fractions containing the desired compound were evaporated and the residue was triturated with Et$_2$O to give a solid which was collected by filtration and dried under vacuum to afford the title compound (0.086 g, 48%); $^1$H NMR (400 MHz, DMSO-d$^6$) 1.29 (3H, d), 1.40-1.60 (3H, m), 1.76 (1H, d), 3.11 (3H, s), 3.12-3.21 (1H, m), 3.53 (1H, t), 3.68 (1H, d), 3.80 (2H, d), 4.01 (1H, d), 4.20 (1H, s), 4.58 (1H, s), 6.95 (1H, d), 7.28 (1H, s), 7.71 (1H, s), 8.83 (1H, s), 9.08 (1H, s), 11.75 (1H, s); m/z: (ES+) MH$^+$, 413.16.

The tert-butyl 4-(4-((R)-3-methylmorpholino)-6-(1-(S-methylsulfonimidoyl)cyclopropyl)pyrimidin-2-yl)-1H-pyrrolo[2,3-c]pyridine-1-carboxylate, used as starting material, was prepared as follows:

1,1'-Bis(diphenylphosphino)ferrocenedichloropalladium(II) (0.906 g, 1.25 mmol) was added to tert-butyl 4-bromo-1H-pyrrolo[2,3-c]pyridine-1-carboxylate (1.24 g, 4.17 mmol), potassium acetate (2.87 g, 29.21 mmol) and bis(pinacolato)diboron (4.73 g, 18.63 mmol) in dioxane (100 ml) under nitrogen. The resulting solution was stirred at reflux for 3 days to afford an approximate 2:1 mixture of boc to de-boc product. To this mixture was added dichlorobis(triphenylphosphine)palladium(II) (0.017 g, 0.02 mmol), (3R)-4-(2-chloro-6-(1-(S-methylsulfonimidoyl)cyclopropyl)pyrimidin-4-yl)-3-methylmorpholine (0.318 g, 0.96 mmol), 2M aqueous sodium carbonate solution (0.577 mL, 1.15 mmol) under nitrogen. The reaction mixture was stirred at 90° C. for 6 hours. The reaction mixture was concentrated, diluted with EtOAc (400 ml), and then washed sequentially with water (300 ml) and saturated brine (75 ml). The organic layer was dried over MgSO$_4$, filtered and then evaporated directly onto silica (30 g). The resulting powder was purified by flash chromatography on silica, eluting with a gradient of 0 to 5% MeOH in DCM. Pure fractions were evaporated to dryness to afford tert-butyl 4-(4-((R)-3-methylmorpholino)-6-(1-(S-methylsulfonimidoyl)cyclopropyl)pyrimidin-2-yl)-1H-pyrrolo[2,3-c]pyridine-1-carboxylate (0.227 g, 46%); $^1$H NMR (400 MHz, DMSO-d$^6$) 1.28 (3H, d), 1.40-1.61 (3H, m), 1.68 (9H, s), 1.76 (1H, dd), 3.09 (3H, d), 3.24 (1H, m), 3.52 (1H, t), 3.67 (1H, dd), 3.79 (2H, d), 4.00 (1H, dd), 4.19 (1H, s), 4.56 (1H, s), 7.00 (1H, d), 7.57 (1H, d), 8.00 (1H, d), 9.25 (1H, s), 9.37 (1H, s); m/z: (ES+) MH$^+$, 513.19.

EXAMPLE 3.01 AND EXAMPLE 3.02

N-methyl-1-{4-[1-methyl-1-((S)—S-methylsulfonimidoyl)ethyl]-6-[(3R)-3-methylmorpholin-4-yl]pyrimidin-2-yl}-1H-benzimidazol-2-amine and
N-methyl-1-{4-[1-methyl-1-((R)—S-methylsulfonimidoyl)ethyl]-6-[(3R)-3-methylmorpholin-4-yl]pyrimidin-2-yl}-1H-benzimidazol-2-amine

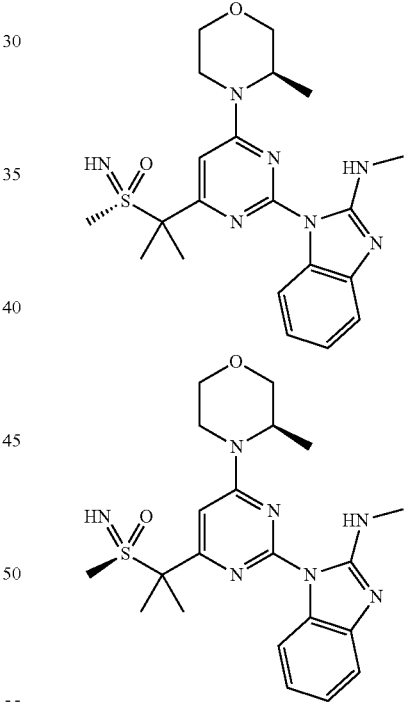

Cesium carbonate (3.19 g, 9.79 mmol) was added to N-[(2-{2-chloro-6-[(3R)-3-methylmorpholin-4-yl]pyrimidin-4-yl}propan-2-yl)(methyl)oxido-λ6-sulfanylidene]-2,2,2-trifluoroacetamide (0.7 g, 1.63 mmol) and N-methyl-1H-benzo[d]imidazol-2-amine (0.360 g, 2.45 mmol) in DMA (10 ml). The resulting suspension was stirred at 80° C. for 5 hours. The reaction mixture was filtered and then concentrated in vacuo. The residue was purified by preparative HPLC, using decreasingly polar mixtures of water (containing 1% NH3) and MeCN as eluents. Fractions containing the desired compound were evaporated to dryness and the residue was purified by preparative chiral HPLC on a Merck 50 mm, 20 μm ChiralCel OJ column, eluting isocratically with 20% EtOH in isohexane (modified with Et3N) as eluent. Fractions containing the first eluting compound, were evaporated and the residue dissolved in DCM (20 ml) and then evaporated onto silica (1 g). The resulting powder was purified by flash chromatography on silica, eluting with a gradient of 0 to 7% MeOH in DCM. Pure fractions were evaporated to afford the title compound: N-methyl-1-{4-[1-methyl-1-((R)—S-methylsulfonimidoyl)ethyl]-6-[(3R)-3-methylmorpholin-4-yl]pyrimidin-2-yl}-1H-benzimidazol-2-amine (66.3 mg, 36%); $^1$H NMR (400 MHz, DMSO-d$^6$) 1.30 (3H, d), 1.76 (6H, d), 2.78 (3H, d), 3.03 (3H, d), 3.33-3.41 (1H, m), 3.47-3.58 (1H, m), 3.68 (1H, dd), 3.81 (1H, d), 3.89 (1H, s), 4.02 (1H, dd), 4.12 (1H, d), 4.53 (1H, s), 6.80 (1H, s), 6.98 (1H, dd), 7.08 (1H, t), 7.24 (1H, d), 8.10 (1H, d), 8.69 (1H, d); m/z: (ES+) MH$^+$, 444.18. Chiral HPLC: (HP1100 System 5, 20 μm Chiralcel OJ (250 mm×4.6 mm) column eluting with iso-Hexane/EtOH/TEA 80/20/0.1) Rf, 21.886 >99%.

Fractions containing the second eluting compound were evaporated and the residue dissolved in DCM (20 ml) and then evaporated onto silica gel (1 g). The resulting powder was purified by flash chromatography on silica, eluting with a gradient of 0 to 7% MeOH in DCM. Pure fractions were evaporated to afford the title compound: N-methyl-1-{4-[1-methyl-1-((S)—S-methylsulfonimidoyl)ethyl]-6-[(3R)-3-methylmorpholin-4-yl]pyrimidin-2-yl}-1H-benzimidazol-2-amine (62.4 mg, 34%); $^1$H NMR (400 MHz, DMSO-d$^6$) 1.31 (3H, d), 1.76 (6H, d), 2.78 (3H, d), 3.03 (3H, d), 3.33-3.39 (1H, m), 3.54 (1H, td), 3.68 (1H, dd), 3.81 (1H, d), 3.88 (1H, s), 4.02 (1H, dd), 4.12 (1H, d), 4.53 (1H, s), 6.80 (1H, s), 6.92-7.01 (1H, m), 7.08 (1H, td), 7.24 (1H, d), 8.10 (1H, d), 8.69 (1H, d); m/z: (ES+) MH$^+$, 444.15. Chiral HPLC: (HP1100 System 5, 20 μm Chiralcel OJ (250 mm×4.6 mm) column eluting with iso-Hexane/EtOH/TEA 80/20/0.1) Rf, 34.353 99.4%.

The N-[(2-{2-chloro-6-[(3R)-3-methylmorpholin-4-yl]pyrimidin-4-yl}propan-2-yl)(methyl)oxido-λ6-sulfanylidene]-2,2,2-trifluoroacetamide, used as starting material, was prepared as follows:

a) (3R)-4-(2-Chloro-6-(methylsulfinylmethyl)pyrimidin-4-yl)-3-methylmorpholine (1.75 g, 6.04 mmol) was dissolved in DMF (34.6 ml), to this was added slowly NaH (0.604 g, 15.10 mmol) and the reaction mixture was stirred for 5 minutes at RT. To the mixture was rapidly added methyl iodide (0.944 ml, 15.10 mmol) and the mixture was stirred for 1 hour. The reaction mixture was quenched with saturated NH$_4$Cl solution (50 mL), extracted with DCM (3×50 mL) and the combined organic layers were passed through a phase separating column and then evaporated to afford a yellow gum. Water (50 mL) was added to the gum and the mixture extracted with EtOAc (3×50 mL). The combined organic layers were dried over MgSO$_4$, filtered and then evaporated. The residue was purified by flash chromatography on silica, eluting with a gradient of 0 to 3% MeOH in DCM. Pure fractions were evaporated to afford (3R)-4-(2-chloro-6-(2-(methylsulfinyl)propan-2-yl)pyrimidin-4-yl)-3-methylmorpholine (1.693 g, 88%); $^1$H NMR (400 MHz, DMSO-d$^6$) 1.19 (3H, d), 1.49 (6H, dd), 2.17 (3H, t), 3.19 (1H, dd), 3.37-3.48 (1H, m), 3.57 (1H, dd), 3.71 (1H, d), 3.92 (1H, d), 4.03 (1H, s), 4.41 (1H, s), 6.70 (1H, s); m/z: (ES+) MH$^+$, 318.09 and 320.04.

b) Iodobenzene diacetate (1.716 g, 5.33 mmol) was added to (3R)-4-(2-chloro-6-(2-(methylsulfinyl)propan-2-yl)pyrimidin-4-yl)-3-methylmorpholine (1.693 g, 5.33 mmol), magnesium oxide (0.859 g, 21.31 mmol), 2,2,2-trifluoroacetamide (1.204 g, 10.65 mmol) and rhodium(II) acetate dimer (0.059 g, 0.13 mmol) in DCM (100 mL). The resulting suspension was stirred at RT for 18 hours. The reaction mixture was filtered through Celite and then concentrated in vacuo onto silica (15 g). The resulting powder was purified by flash chromatography on silica, eluting with a gradient of 0 to 10% MeOH in DCM. Pure fractions were evaporated to afford N-[(2-{2-chloro-6-[(3R)-3-methylmorpholin-4-yl]pyrimidin-4-yl}propan-2-yl)(methyl)oxido-λ6-sulfanylidene]-2,2,2-trifluoroacetamide (0.700 g, 31%); $^1$H NMR (400 MHz, DMSO-d$^6$) 1.20 (3H, dd), 1.83 (6H, d), 3.20 (1H, dd), 3.41 (1H, dddd), 3.56 (1H, d), 3.59 (3H, d), 3.72 (1H, d), 3.94 (1H, dd), 4.07 (1H, s), 4.45 (1H, s), 6.93 (1H, d); m/z: (ES+) MH$^+$, 429.4 and 431.5.

EXAMPLE 4.01 AND EXAMPLE 4.02

N-Methyl-1-{4-[(3R)-3-methylmorpholin-4-yl]-6-[4-((S)—S-methylsulfonimidoyl)tetrahydro-2H-pyran-4-yl]pyrimidin-2-yl}-1H-benzimidazol-2-amine and
N-methyl-1-{4-[(3R)-3-methylmorpholin-4-yl]-6-[4-((R)—S-methylsulfonimidoyl)tetrahydro-2H-pyran-4-yl]pyrimidin-2-yl}-1H-benzimidazol-2-amine

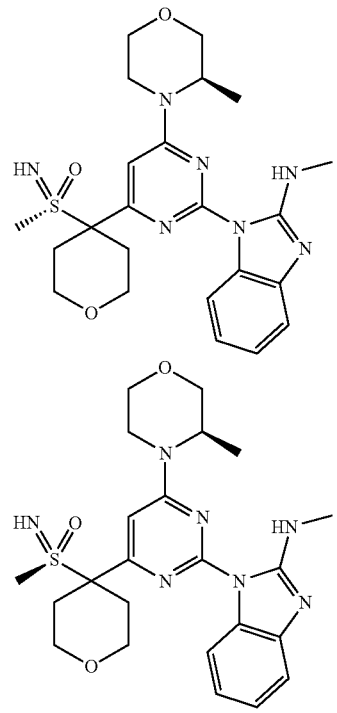

Cesium carbonate (2.076 g, 6.37 mmol) was added to N-[(4-{2-chloro-6-[(3R)-3-methylmorpholin-4-yl]pyrimidin-4-yl}tetrahydro-2H-pyran-4-yl)(methyl)oxido-λ6-sulfanylidene]-2,2,2-trifluoroacetamide (1.00 g, 2.12 mmol), sodium methanesulfinate (0.217 g, 2.12 mmol) and N-methyl-1H-benzo[d]imidazol-2-amine (0.313 g, 2.12 mmol) in DMA (20 ml). The resulting suspension was stirred at 80° C. for 18 hours. The reaction mixture was filtered and then evaporated. The residue was dissolved in EtOAc (100 mL) and washed sequentially with water (100 mL) and then with saturated brine (10 mL). The aqueous layer was washed with EtOAc (2×100 mL). The organic layers were combined, dried over MgSO$_4$, filtered and then evaporated. The residue was purified by flash chromatography on silica, eluting with a gradient of 0 to 7% MeOH in DCM. Fractions containing product were evaporated and the residue was purified by preparative chiral HPLC on a ChiralCel OD column, eluting isocratically with 50% hexane in EtOH (modified with Et₃N) as eluent. Fractions containing isomer 1, eluted first, were evaporated and the residue dissolved in DCM (10 ml) and then evaporated onto silica (0.5 g). The resulting powder was purified by flash chromatography on silica, eluting with a gradient of 0 to 7% MeOH in DCM. Pure fractions were evaporated to dryness to afford isomer 1 (58.0 mg, 36%); $^1$H NMR (400 MHz, DMSO-d$^6$) 1.31 (3H, d), 2.19-2.35 (2H, m), 2.65-2.75 (5H, m), 3.02 (2H, d), 3.24 (2H, dd), 3.33-3.39 (1H, m), 3.56 (1H, td), 3.71 (1H, dd), 3.81 (1H, d), 3.87-3.97 (2H, m), 4.03 (1H, dd), 4.06 (1H, s), 4.16 (1H, d), 4.53 (1H, s), 6.90 (1H, s), 6.99 (1H, td), 7.09 (1H, td), 7.26 (1H, dd), 8.06 (1H, d), 8.39 (1H, q); m/z: (ES+) MH⁺, 486.53. Chiral HPLC: (HP1100 System 4, 20 μm Chiralpak OJ (250 mm×4.6 mm) column eluting with Hexane/EtOH/TEA 50/50/0.1) Rf, 8.874 >99%.

Fractions containing isomer 2, eluted second, were evaporated and the residue dissolved in DCM (10 mL) and then evaporated onto silica gel (0.5 g). The resulting powder was purified by flash chromatography on silica, eluting with a gradient of 0 to 7% MeOH in DCM. Pure fractions were evaporated to afford isomer 2 (71.8 mg, 44%); $^1$H NMR (400 MHz, DMSO-d$^6$) 1.30 (3H, d), 2.19-2.36 (2H, m), 2.61-2.76 (5H, m), 3.02 (3H, d), 3.18-3.27 (2H, m), 3.36 (1H, dd), 3.56 (1H, td), 3.71 (1H, dd), 3.81 (1H, d), 3.93 (2H, dd), 4.00-4.08 (2H, m), 4.17 (1H, d), 4.52 (1H, s), 6.91 (1H, s), 6.99 (1H, td), 7.09 (1H, td), 7.26 (1H, d), 8.06 (1H, d), 8.39 (1H, q); m/z: (ES+) MH⁺, 486.57. Chiral HPLC: (HP1100 System 4, 20 μm Chiralpak OJ (250 mm×4.6 mm) column eluting with Hexane/EtOH/TEA 50/50/0.1) Rf, 12.742 >99%.

The N-[(4-{2-chloro-6-[(3R)-3-methylmorpholin-4-yl]pyrimidin-4-yl}tetrahydro-2H-pyran-4-yl)(methyl)oxido-λ6-sulfanylidene]-2,2,2-trifluoroacetamide, used as starting material, can be prepared as follows:

a) Sodium hydroxide (50% w/w) (20.04 ml, 379.60 mmol) was added to (3R)-4-(2-chloro-6-(methylsulfinylmethyl)pyrimidin-4-yl)-3-methylmorpholine (2.2 g, 7.59 mmol), 1-bromo-2-(2-bromoethoxy)ethane (3.79 ml, 30.37 mmol) and tetraoctylammonium bromide (0.415 g, 0.76 mmol) in methyl THF (20.05 ml). The resulting mixture was stirred at RT for 90 minutes. The reaction mixture was diluted with methyl THF (50 mL), and washed sequentially with water (50 ml) and saturated brine (5 ml). The organic layer was dried over MgSO₄, filtered and then evaporated onto silica (30 g). The resulting powder was purified by flash chromatography on silica, eluting with a gradient of 0 to 5% MeOH in DCM. Pure fractions were evaporated to afford (3R)-4-(2-chloro-6-(4-(methylsulfinyl)tetrahydro-2H-pyran-4-yl)pyrimidin-4-yl)-3-methylmorpholine (1.360 g, 50%); $^1$H NMR (400 MHz, DMSO-d$^6$) 1.84-1.96 (1H, m), 2.02 (1H, td), 2.09 (3H, d), 2.27-2.45 (2H, m), 3.14 (1H, d), 3.10-3.26 (3H, m), 3.24 (1H, d), 3.33-3.41 (1H, m), 3.45 (1H, td), 3.60 (1H, dd), 3.71 (1H, d), 3.78-3.87 (1H, m), 3.87-3.97 (2H, m), 4.07 (1H, d), 4.32-4.48 (1H, m), 6.76 (1H, s); m/z: (ES+) MH⁺, 360.11 and 362.06.

b) Iodobenzene diacetate (0.788 g, 2.45 mmol) was added to (3R)-4-(2-chloro-6-(4-(methylsulfinyl)tetrahydro-2H-pyran-4-yl)pyrimidin-4-yl)-3-methylmorpholine (0.88 g, 2.45 mmol), magnesium oxide (0.394 g, 9.78 mmol), 2,2,2-trifluoroacetamide (0.553 g, 4.89 mmol) and rhodium(II) acetate dimer (0.027 g, 0.06 mmol) in DCM (20 ml). The resulting suspension was stirred at RT for 18 hours. The reaction mixture was filtered through Celite and then concentrated in vacuo onto silica (50 g). The resulting powder was purified by flash chromatography on silica, eluting with a gradient of 20 to 60% EtOAc in isohexane. Pure fractions were evaporated to afford N-[(4-{2-chloro-6-[(3R)-3-methylmorpholin-4-yl]pyrimidin-4-yl}tetrahydro-2H-pyran-4-yl)(methyl)oxido-λ6-sulfanylidene]-2,2,2-trifluoroacetamide (1.018 g, 88%); $^1$H NMR (400 MHz, DMSO-d$^6$) 1.34 (3H, dd), 2.49 (1H, td), 2.63 (2H, ddd), 2.75-2.82 (1H, m), 3.26 (3H, d), 3.29-3.41 (3H, m), 3.49 (1H, s), 3.51-3.60 (1H, m), 3.63-3.73 (1H, m), 3.80 (1H, d), 3.98-4.11 (4H, m), 6.68 (1H, d); m/z: (ES−) M-H⁻, 469.04 and 471.03.

EXAMPLE 4.03

4-{4-[(3R)-3-Methylmorpholin-4-yl]-6-[4-(S)—S-methylsulfonimidoyl)tetrahydro-2H-pyran-4-yl]pyrimidin-2-yl}-1H-indole

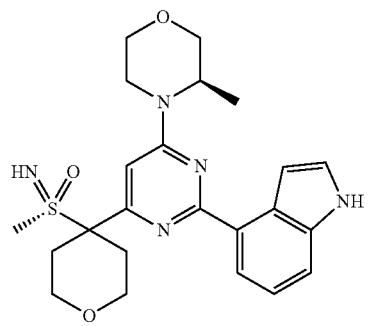 [SMILES: C[C@@H]1COCCN1c1cc(C2([S@@](C)(=N)=O)CCOCC2)nc(-c2cccc3[nH]ccc23)n1]

A solution of N-[(4-{2-chloro-6-[(3R)-3-methylmorpholin-4-yl]pyrimidin-4-yl}tetrahydro-2H-pyran-4-yl)(methyl)oxido-λ6-(S)-sulfanylidene]-2,2,2-trifluoroacetamide (50 mg, 0.11 mmol), 1H-indol-4-ylboronic acid (17.09 mg, 0.11 mmol), 4,4'-di-tert-butylbiphenyl (5.66 mg, 0.02 mmol) and potassium carbonate (29.3 mg, 0.21 mmol) in degassed DME:water (4:1) (2.5 mL) was added to bis(di-tert-butyl(4-dimethylaminophenyl)phosphine)dichloropalladium(II) (A-Phos) (7.52 mg, 10.62 μmol) under nitrogen. The resulting mixture was stirred at RT for 2 hours and then at 55° C. for 20 hours. The reaction mixture was filtered and then purified by preparative HPLC, using decreasingly polar mixtures of water (containing 1% NH₃) and MeCN as eluents. Fractions containing product were evaporated to afford the title compound (20.80 mg, 43%); $^1$H NMR (500 MHz, DMSO-d$^6$) 1.28 (3H, d), 2.19-2.36 (2H, m), 2.72 (3H, d), 2.84 (2H, t), 3.18 (1H, t), 3.20-3.29 (2H, m), 3.56 (1H, td), 3.71 (1H, dd), 3.81 (2H, d), 3.95 (2H, t), 4.03 (1H, dd), 4.29 (1H, d), 4.59 (1H, s), 6.87 (1H, d), 7.20 (1H, t), 7.27 (1H, t), 7.41-7.49 (1H, m), 7.54 (1H, dd), 8.11 (1H, dd), 11.24 (1H, s); m/z: (ES+) MH⁺, 456.54.

The N-[(4-{2-chloro-6-[(3R)-3-methylmorpholin-4-yl]pyrimidin-4-yl}tetrahydro-2H-pyran-4-yl)(methyl)oxido-λ6-(S)-sulfanylidene]-2,2,2-trifluoroacetamide, used as starting material, can be prepared as follows:

a) 1-bromo-2-(2-bromoethoxy)ethane (2.323 ml, 18.63 mmol) was added to (R)-4-(2-chloro-6-((S)-methylsulfinylmethyl)pyrimidin-4-yl)-3-methylmorpholine (1.8 g, 6.21 mmol), sodium hydroxide (16.40 ml, 310.58 mmol) and tetraoctylammonium bromide (0.340 g, 0.62 mmol) in methyl THF (12.34 ml). The resulting mixture was stirred at RT for 24 hours. The reaction mixture was diluted with methyl THF (50 mL), and then washed with water (100 mL). The organic layer was dried over MgSO₄, filtered and evaporated onto silica (5 g). The resulting powder was purified by flash chromatography on silica, eluting with a gradient of 0 to 5% MeOH in DCM. Pure fractions were evaporated to afford (R)-4-(2-chloro-6-(4-((S)-methylsulfinyl)tetrahydro-2H-pyran-4-yl)pyrimidin-4-yl)-3-methylmorpholine (1.461 g, 65%); ¹H NMR (400 MHz, CDCl₃) 1.34 (3H, d), 1.84-1.94 (1H, m), 2.10 (3H, s), 2.24-2.37 (2H, m), 2.44 (1H, ddd), 3.30 (1H, td), 3.41 (1H, ddd), 3.51-3.64 (2H, m), 3.65-3.73 (1H, m), 3.75-3.82 (1H, m), 3.90-4.08 (4H, m), 4.36 (1H, s), 6.46 (1H, s); m/z: (ES+) MH⁺, 360.15 and 362.11.

b) Iodobenzene diacetate (1.437 g, 4.46 mmol) was added to (R)-4-(2-chloro-6-(4-((S)-methylsulfinyl)tetrahydro-2H-pyran-4-yl)pyrimidin-4-yl)-3-methylmorpholine (1.46 g, 4.06 mmol), 2,2,2-trifluoroacetamide (0.459 g, 4.06 mmol), rhodium(II)acetate dimer (0.045 g, 0.10 mmol) and magnesium oxide (0.654 g, 16.23 mmol) in DCM (20.29 ml). The resulting suspension was stirred at RT for 48 hours. Further 2,2,2-trifluoroacetamide (0.459 g, 4.06 mmol), magnesium oxide (0.654 g, 16.23 mmol), iodobenzene diacetate (1.437 g, 4.46 mmol) and rhodium(II)acetate dimer (0.045 g, 0.10 mmol) were added and the suspension was stirred at RT for a further 24 hours. The reaction mixture was filtered and then evaporated onto silica (5 g). The resulting powder was purified by flash chromatography on silica, eluting with a gradient of 20 to 100% EtOAc in isohexane. Pure fractions were evaporated to afford N-[(4-{2-chloro-6-[(3R)-3-methylmorpholin-4-yl]pyrimidin-4-yl}tetrahydro-2H-pyran-4-yl)(methyl)oxido-λ6-(S)-sulfanylidene]-2,2,2-trifluoroacetamide (1.421 g, 74%); ¹H NMR (400 MHz, DMSO-d⁶) 1.20 (3H, d), 2.19-2.31 (2H, m), 2.72-2.84 (2H, m), 3.11-3.28 (3H, m), 3.40-3.45 (1H, m), 3.46 (3H, s), 3.53-3.61 (1H, m), 3.74 (1H, d), 3.94 (3H, d), 4.12 (1H, s), 4.47 (1H, s), 7.05 (1H, s); m/z: (ES+) MH⁺, 471.04 and 473.00.

EXAMPLE 5.01 AND EXAMPLE 5.02

4-Fluoro-N-methyl-1-{4-[1-methyl-1-((S)—S-methylsulfonimidoyl)ethyl]-6-[(3R)-3-methylmorpholin-4-yl]pyrimidin-2-yl}-1H-benzimidazol-2-amine and 4-fluoro-N-methyl-1-{4-[1-methyl-1-((R)—S-methylsulfonimidoyl)ethyl]-6-[(3R)-3-methylmorpholin-4-yl]pyrimidin-2-yl}-1H-benzimidazol-2-amine

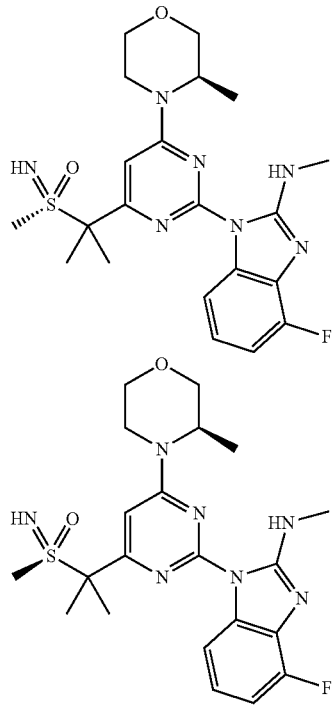

Cesium carbonate (2.74 g, 8.41 mmol) was added to an approximate 4.3:1 mixture of R:S isomers of N-[(2-{2-chloro-6-[(3R)-3-methylmorpholin-4-yl]pyrimidin-4-yl}propan-2-yl)(methyl)oxido-λ6-sulfanylidene]-2,2,2-trifluoroacetamide (0.600 g, 1.40 mmol), sodium methanesulfinate (0.143 g, 1.40 mmol) and 7-fluoro-N-methyl-1H-benzo[d]imidazol-2-amine (0.347 g, 2.10 mmol) in DMA (8 ml). The resulting suspension was stirred at 80° C. for 5 hours. The reaction mixture was filtered, diluted with EtOAc (100 ml), and washed sequentially with water (100 ml), water (100 ml), and saturated brine (100 ml). The organic layer was dried over MgSO₄, filtered and then evaporated. The residue was purified by flash chromatography on silica, eluting with a gradient of 0 to 5% MeOH in DCM. Pure fractions were evaporated and the residue purified by preparative chiral chromatography on a Merck 50 mm, 20 μm Chiracel OJ column, eluting isocratically with heptane/(EtOH/MeOH 50/50)/TEA 75/25/0.1 as eluent. The fractions containing product were evaporated to afford the title compound: 4-fluoro-N-methyl-1-{4-[1-methyl-1-((R)—S-methylsulfonimidoyl)ethyl]-6-[(3R)-3-methylmorpholin-4-yl]pyrimidin-2-yl}-1H-benzimidazol-2-amine (278 mg, 43%) as the first eluting compound; ¹H NMR (400 MHz, DMSO-d⁶) 1.30 (3H, d), 1.77 (6H, d), 2.79 (3H, s), 3.05 (3H, d), 3.35 (1H, dd), 3.47-3.59 (1H, td), 3.69 (1H, dd), 3.81 (1H, d), 3.93 (1H, s), 4.03 (1H, dd), 4.12 (1H, d), 4.53 (1H, s), 6.83 (1H, s), 6.90-7.01 (2H, m), 7.92-7.96 (1H, m), 8.81 (1H, q); m/z: (ES+) MH⁺, 462.53. Chiral HPLC: (Gilson prep, 50 mm 20 μm Chiralcel OJ column eluting with Heptane/(EtOH/MeOH 50/50)/TEA 75/25/0.1) Rf, 10.163 >99%. and 4-fluoro-N-methyl-1-{4-[1-methyl-1-((S)—S-methylsulfonimidoyl)ethyl]-6-[(3R)-3-methylmorpholin-4-yl]pyrimidin-2-yl}-1H-benzimidazol-2-amine (96 mg, 15%) as the second eluting compound; ¹H NMR (400 MHz, DMSO-d⁶) 1.33 (3H, d), 1.79 (6H, d), 2.83 (3H, s), 3.09 (3H, d), 3.38 (1H, dd), 3.59 (1H, td), 3.73 (1H, dd), 3.86 (1H, d), 3.97 (1H, s), 4.06 (1H, dd), 4.16 (1H, d), 4.59 (1H, s), 6.88 (1H, s), 6.94-7.05 (2H, m), 7.94-8.02 (1H, m), 8.86 (1H, q); m/z: (ES+) MH⁺, 462.53. Chiral HPLC: (Gilson prep, 50 mm 20 μm Chiralcel OJ column eluting with Heptane/(EtOH/MeOH 50/50)/TEA 75/25/0.1) Rf, 14.239 >99%.

The N-[(2-{2-chloro-6-[(3R)-3-methylmorpholin-4-yl]pyrimidin-4-yl}propan-2-yl)(methyl)oxido-λ6-sulfanylidene]-2,2,2-trifluoroacetamide, used as starting material, was prepared as follows:

a) Methyl iodide (4.70 ml, 75.09 mmol) was added to (R)-4-(2-chloro-6-((R)-methylsulfinylmethyl)pyrimidin-4-yl)-3-methylmorpholine (5.44 g, 18.77 mmol), tetraoctylammonium bromide (1.026 g, 1.88 mmol) and sodium hydroxide (49.6 ml, 938.64 mmol) in methyl THF (110 ml). The resulting mixture was stirred at RT for 18 hours. The reaction mixture was diluted with water (250 ml). The organic layer was dried over MgSO₄, filtered and evaporated onto silica gel (10 g). The resulting powder was purified by flash chromatography on silica, eluting with a gradient of 0 to 5% MeOH in DCM. Pure fractions were evaporated to afford (R)-4-(2-chloro-6-(2-((R)-methylsulfinyl)propan-2-yl)pyrimidin-4-yl)-3-methylmorpholine (3.10 g, 52%); ¹H NMR (400 MHz, CDCl₃) 1.32 (3H, t), 1.59 (3H, s), 1.64 (3H, s), 2.23 (3H, d), 3.22-3.36 (1H, m), 3.48-3.59 (1H, m), 3.69 (1H, dd), 3.73-3.81 (1H, m), 4.00 (1H, dd), 4.05 (1H, d), 4.31 (1H, s), 6.45 (1H, d); m/z: (ES+) MH⁺, 318.02 and 319.98.

b) Iodobenzene diacetate (2.77 g, 8.59 mmol) was added to a mixture of (3R)-4-(2-chloro-6-(2-(methylsulfinyl)propan-2-yl)pyrimidin-4-yl)-3-methylmorpholine (1.03 g, 3.24 mmol), (3R)-4-(2-chloro-6-(2-((R)-methylsulfinyl)propan-2-yl)pyrimidin-4-yl)-3-methylmorpholine (1.7 g, 5.35 mmol), magnesium oxide (1.385 g, 34.36 mmol), 2,2,2-trifluoroacetamide (1.942 g, 17.18 mmol) and rhodium(II) acetate dimer (0.095 g, 0.21 mmol) in DCM (72 ml). The resulting suspension was stirred at RT for 70 hours. Further magnesium oxide (0.69 g, 17.18 mmol), iodobenzene diacetate (1.38 g, 4.30 mmol), 2,2,2-trifluoroacetamide (0.97 g, 8.59 mmol) and rhodium(II) acetate dimer (0.048 g, 0.105 mmol) were added and the mixture was stirred at RT for 18 hours. The reaction mixture was filtered through Celite and then concentrated in vacuo. The residue was purified by flash chromatography on silica, eluting with a gradient of 20 to 50% EtOAc in heptane. Pure fractions were evaporated to afford an approximate 4.3:1 mixture of R:S N-[(2-{2-chloro-6-[(3R)-3-methylmorpholin-4-yl]pyrimidin-4-yl}propan-2-yl)(methyl)oxido-λ6-sulfanylidene]-2,2,2-trifluoroacetamide (1.705 g, 46%); $^1$H NMR (400 MHz, DMSO-d$^6$) 1.18 (3H, d), 1.83 (6H, s), 3.20-3.24 (1H, m), 3.36-3.48 (1H, m), 3.53-3.65 (4H, m), 3.68-3.79 (1H, m), 3.94 (1H, dd), 4.03-4.07 (1H, m), 4.43-4.47 (1H, m), 6.94 (1H, s); m/z: (ES−) M-H$^−$, 427.26.

EXAMPLE 5.03, EXAMPLE 5.04, EXAMPLE 5.05 AND EXAMPLE 5.06

6-Fluoro-N-methyl-1-{4-[1-methyl-1-((R)—S-methylsulfonimidoyl)ethyl]-6-[(3R)-3-methylmorpholin-4-yl]pyrimidin-2-yl}-1H-benzimidazol-2-amine, 5-Fluoro-N-methyl-1-{4-[1-methyl-1-((R)—S-methylsulfonimidoyl)ethyl]-6-[(3R)-3-methylmorpholin-4-yl]pyrimidin-2-yl}-1H-benzimidazol-2-amine, 5-Fluoro-N-methyl-1-{4-[1-methyl-1-((S)—S-methylsulfonimidoyl)ethyl]-6-[(3R)-3-methylmorpholin-4-yl]pyrimidin-2-yl}-1H-benzimidazol-2-amine and 6-fluoro-N-methyl-1-{4-[1-methyl-1-((S)—S-methylsulfonimidoyl)ethyl]-6-[(3R)-3-methylmorpholin-4-yl]pyrimidin-2-yl}-1H-benzimidazol-2-amine

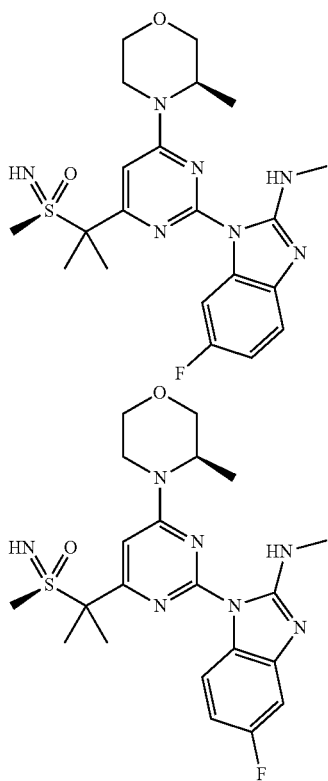

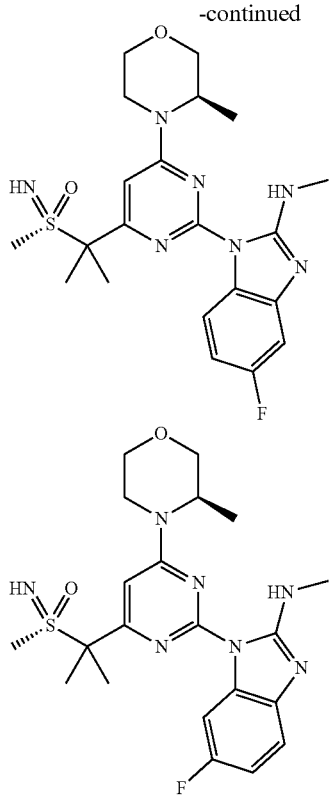

Cesium carbonate (5.01 g, 15.39 mmol) was added to an approximate 4.3:1 mixture R:S isomers of N-[(2-{2-chloro-6-[(3R)-3-methylmorpholin-4-yl]pyrimidin-4-yl}propan-2-yl)(methyl)oxido-λ6-sulfanylidene]-2,2,2-trifluoroacetamide (1.10 g, 2.56 mmol), sodium methanesulfinate (0.262 g, 2.56 mmol) and 6-fluoro-N-methyl-1H-benzo[d]imidazol-2-amine (0.720 g, 4.36 mmol) in DMA (16 ml). The resulting suspension was stirred at 80° C. for 5 hours. The reaction mixture was filtered. The reaction mixture was diluted with EtOAc (100 ml), and washed sequentially with water (100 ml), water (100 ml), and saturated brine (100 ml). The organic layer was dried over MgSO$_4$, filtered and then evaporated. The residue was purified by flash chromatography on silica, eluting with a gradient of 0 to 5% MeOH in DCM. Pure fractions were evaporated and the residue was purified by preparative chiral SFC on a 5 μm Chiracel OJ-H SFC (250 mm×10 mm) column, eluting with CO$_2$/MeOH+0.5 N, NDMEA 90/10 as eluent. The fractions containing product were evaporated to afford the title compound: 6-fluoro-N-methyl-1-{4-[1-methyl-1-((R)—S-methylsulfonimidoyl)ethyl]-6-[(3R)-3-methylmorpholin-4-yl]pyrimidin-2-yl}-1H-benzimidazol-2-amine (198 mg, 17%) as the first eluting compound; $^1$H NMR (400 MHz, DMSO-d$^6$) 1.32 (3H, d), 1.77 (6H, d), 2.78 (3H, s), 3.02 (3H, d), 3.33-3.40 (1H, m), 3.55 (1H, td), 3.69 (1H, dd), 3.83 (1H, d), 3.92 (1H, s), 3.97-4.15 (2H, m), 4.53 (1H, d), 6.84 (1H, s), 6.91-6.95 (1H, m), 7.21 (1H, dd), 7.89 (1H, dd), 8.66 (1H, q); m/z: (ES+) MH$^+$, 462.51. Chiral SFC: (Berger Minigram, 5 μm Chiralcel OJ-H (250 mm×4.6 mm) column eluting with CO$_2$/MeOH/N, NDMEA 90/10/0.5) Rf, 5.56 98.9%. and the title compound: 5-fluoro-N-methyl-1-{4-[1-methyl-1-((S)—S-methylsulfonimidoyl)ethyl]-6-[(3R)-3-methylmorpholin-4-yl]pyrimidin-2-yl}-1H-benzimidazol-2-amine (61 mg, 5%) as the fourth eluting compound; $^1$H NMR (400 MHz, DMSO-d$^6$) 1.30 (3H, d), 1.77 (6H, d), 2.78 (3H, s), 3.03 (3H, d), 3.32-3.36 (1H, m), 3.54 (1H, td), 3.68 (1H, dd), 3.81 (1H, d), 3.91 (1H, s), 3.97-4.15 (2H, m), 4.53 (1H, d), 6.72-6.84 (2H, m), 7.04 (1H, dd), 8.06 (1H, dd), 8.86 (1H, q); m/z: (ES+) MH+, 462.53. Chiral SFC: (Berger Minigram, 5 μm Chiralcel OJ-H (250 mm×4.6 mm) column eluting with CO₂/MeOH/N, NDMEA 90/10/0.5) Rf, 10.29 96.3%.

fractions containing the second and third eluting compounds were purified by preparative chiral SFC on a 5 μm Chiralcel OD-H (250 mm×4.6 mm) column eluting with CO₂/MeOH/N, NDMEA 85/15/0.5 as eluent. The fractions containing product were evaporated to afford the title compound: 5-fluoro-N-methyl-1-{4-[1-methyl-1-((R)—S-methylsulfonimidoyl)ethyl]-6-[(3R)-3-methylmorpholin-4-yl]pyrimidin-2-yl}-1H-benzimidazol-2-amine (106 mg, 9%) as the second eluting compound; ¹H NMR (400 MHz, DMSO-d⁶) 1.30 (3H, d), 1.76 (6H, d), 2.78 (3H, s), 3.03 (3H, d), 3.31-3.39 (1H, m), 3.54 (1H, td), 3.69 (1H, dd), 3.81 (1H, d), 3.92 (1H, s), 3.97-4.18 (2H, m), 4.52 (1H, d), 6.73-6.84 (2H, m), 7.04 (1H, dd), 8.07 (1H, dd), 8.86 (1H, q); m/z: (ES+) MH+, 462.53. Chiral SFC: (Berger Minigram, 5 μm Chiralcel OD-H (250 mm×4.6 mm) column eluting with CO₂/MeOH/N, NDMEA 85/15/0.5) Rf, 10.94 98.9%.

fractions containing the first eluting compound were repurified by preparative chiral SFC on a 5 μm Chiralcel OD-H (250 mm×4.6 mm) column eluting with CO₂/MeOH/N, NDMEA 85/15/0.5 as eluent. The fractions containing product were evaporated to afford the title compound: 6-fluoro-N-methyl-1-{4-[1-methyl-1-((S)—S-methylsulfonimidoyl)ethyl]-6-[(3R)-3-methylmorpholin-4-yl]pyrimidin-2-yl}-1H-benzimidazol-2-amine (12 mg, 1%); ¹H NMR (400 MHz, DMSO-d⁶) 1.14 (3H, d), 1.58 (6H, d), 2.60 (3H, s), 2.83 (3H, d), 3.16-3.25 (1H, m), 3.35 (1H, td), 3.50 (1H, dd), 3.64 (1H, d), 3.72 (1H, s), 3.79-3.98 (2H, m), 4.34 (1H, d), 6.65 (1H, s), 6.69-6.77 (1H, m), 7.03 (1H, dd), 7.71 (1H, dd), 8.48 (1H, q); m/z: (ES+) MH+, 462.53. Chiral SFC: (Berger Minigram, 5 μm Chiralcel OD-H (250 mm×4.6 mm) column eluting with CO₂/MeOH/N, NDMEA 85/15/0.5) Rf, 7.47 88.4%.

The 6-fluoro-N-methyl-1H-benzo[d]imidazol-2-amine, used as starting material, can be prepared as follows:

a) 4-Fluorobenzene-1,2-diamine (2 g, 15.86 mmol) was dissolved in THF (49.4 ml) and 1,1'-Carbonyldiimidazole (2.83 g, 17.44 mmol) was added at RT. The reaction mixture was stirred overnight at RT. To this was added concentrated ammonia solution (1.5 ml) and the mixture stirred for 30 minutes and then diluted with water (100 ml). The resultant solid was collected by filtration, washed with water, followed by Et₂O and then dried in vacuo to afford 5-fluoro-1H-benzo[d]imidazol-2(3H)-one (1.250 g, 52%); ¹H NMR (400 MHz, DMSO-d⁶) 6.66-6.79 (2H, m), 6.81-6.94 (1H, m), 10.64 (1H, s), 10.76 (1H, s); m/z: (ES+) MH+, 151.19.

b) A solution of 5-fluoro-1H-benzo[d]imidazol-2(3H)-one (1.25 g, 8.22 mmol) in phosphorus oxychloride (25.2 ml, 270.34 mmol) was heated for 18 hours at 100° C. The reaction mixture was cooled to RT and excess of POCl₃ was evaporated in vacuo. The residue was neutralized with saturated NaHCO3 solution (10 ml) and extracted with EtOAc (3×20 ml). The organic phase was washed with brine and then dried over MgSO₄, filtered and concentrated under reduced pressure to afford 2-chloro-6-fluoro-1H-benzo[d]imidazole (1.146 g, 82%); ¹H NMR (400 MHz, DMSO-d⁶) 7.09 (1H, ddd), 7.36 (1H, dd), 7.53 (1H, dd); m/z: (ES+) MH+, 171.34.

c) 2-Chloro-6-fluoro-1H-benzo[d]imidazole (1.146 g, 6.72 mmol) was charged to high pressure autoclave PV10832 (Parr 160 ml) with methylamine 40% EtOH solution (50 ml, 6.72 mmol) and sealed on its trolley and the resulting solution heated to 160° C. in high pressure blast cell 60 for 16 hours. The pressure in the autoclave reached 13 bar. The reaction mixture was evaporated and the residue dissolved in MeOH and added to an SCX column. The desired product was eluted from the column using 7M NH₃/MeOH. Fractions containing product were evaporated and the residue was purified by flash chromatography on silica, eluting with a gradient of 0 to 10% MeOH in DCM. Pure fractions were evaporated to afford 6-fluoro-N-methyl-1H-benzo[d]imidazol-2-amine (0.707 g, 64%); ¹H NMR (400 MHz, DMSO-d⁶) 2.27 (3H, d), 6.38-6.44 (2H, m), 6.67 (1H, dd), 6.79-6.84 (1H, m); m/z: (ES+) MH+, 166.31.

EXAMPLE 5.07, EXAMPLE 5.08, EXAMPLE 5.09 AND EXAMPLE 5.10

6-Fluoro-N-methyl-1-{4-[(3R)-3-methylmorpholin-4-yl]-6-[1-((R)—S-methylsulfonimidoyl)cyclopropyl]pyrimidin-2-yl}-1H-benzimidazol-2-amine and
5-fluoro-N-methyl-1-{4-[(3R)-3-methylmorpholin-4-yl]-6-[1-((R)—S-methylsulfonimidoyl)cyclopropyl]pyrimidin-2-yl}-1H-benzimidazol-2-amine and
5-fluoro-N-methyl-1-{4-[(3R)-3-methylmorpholin-4-yl]-6-[1-((S)—S-methylsulfonimidoyl)cyclopropyl]pyrimidin-2-yl}-1H-benzimidazol-2-amine and
6-fluoro-N-methyl-1-{4-[(3R)-3-methylmorpholin-4-yl]-6-[1-((S)—S-methylsulfonimidoyl)cyclopropyl]pyrimidin-2-yl}-1H-benzimidazol-2-amine

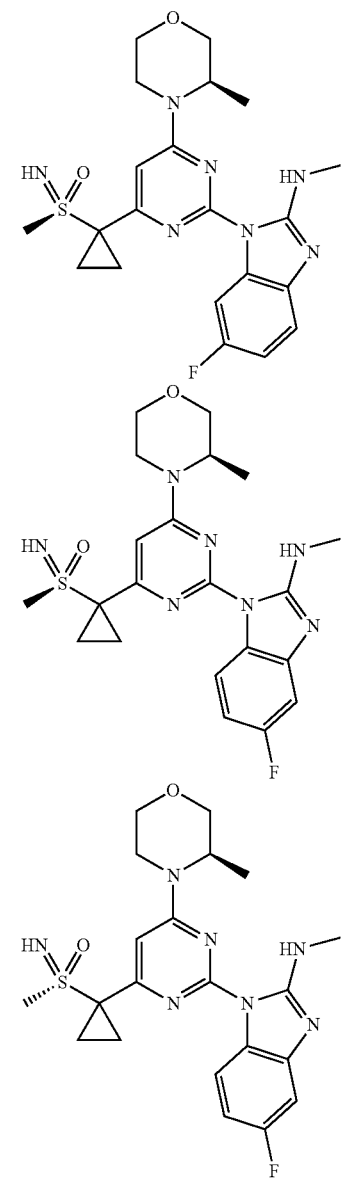

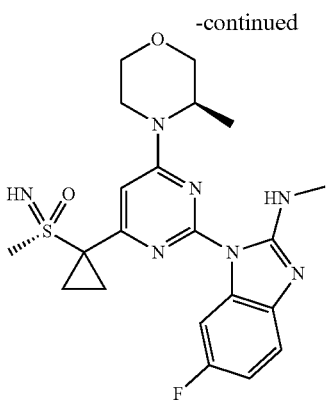

Cesium carbonate (9.28 g, 28.47 mmol) was added to an approximate 4:1 mixture of R:S isomers of (3R)-4-(2-chloro-6-(1-(S-methylsulfonimidoyl)cyclopropyl)pyrimidin-4-yl)-3-methylmorpholine (1.57 g, 4.75 mmol), sodium methanesulfinate (0.484 g, 4.75 mmol) and 6-fluoro-N-methyl-1H-benzo[d]imidazol-2-amine (1.332 g, 8.07 mmol) in DMA (23 ml). The resulting suspension was stirred at 80° C. for 5 hours. The reaction mixture was filtered. The reaction mixture was diluted with EtOAc (100 ml), and washed sequentially with water (100 ml), water (100 ml), and saturated brine (100 ml). The organic layer was dried over MgSO4, filtered and evaporated. The residue was purified by flash chromatography on silica, eluting with a gradient of 0 to 5% MeOH in DCM. Pure fractions were evaporated and the residue was then purified by preparative chiral SFC on a 5 μm Chiralcel OJ-H (20 mm×250 mm) column, using $CO_2$/MeOH/N, NDMEA 90/10/0.5 as eluent. The fractions containing the desired compound were evaporated to afford the title compound: 6-fluoro-N-methyl-1-{4-[(3R)-3-methylmorpholin-4-yl]-6-[1-((R)—S-methylsulfonimidoyl)cyclopropyl]pyrimidin-2-yl}-1H-benzimidazol-2-amine (225 mg, 10%) as the first eluting compound; $^1$H NMR (400 MHz, DMSO-d$^6$) 1.31 (3H, d), 1.4-1.54 (2H, m), 1.57-1.64 (1H, m), 1.77-1.82 (1H, m), 3.00-3.04 (6H, m), 3.33-3.37 (1H, m), 3.53 (1H, td), 3.67 (1H, dd), 3.81 (1H, d), 3.93-4.13 (3H, m), 4.49-4.51 (1H, m), 6.80 (1H, s), 6.93 (1H, ddd), 7.22 (1H, dd), 7.87 (1H, dd), 8.64 (1H, q); m/z: (ES+) MH$^+$, 460.50. Chiral SFC: (Berger Minigram, 5 μm Chiralcel OJ-H (250 mm×4.6 mm) column eluting with $CO_2$/MeOH/N, NDMEA 90/10/0.5) Rf, 7.70 99.9%.
and the title compound: 5-fluoro-N-methyl-1-{4-[(3R)-3-methylmorpholin-4-yl]-6-[1-((R)—S-methylsulfonimidoyl)cyclopropyl]pyrimidin-2-yl}-1H-benzimidazol-2-amine (142 mg, 7%) as the second eluting compound; $^1$H NMR (400 MHz, DMSO-d$^6$) 1.50 (3H, d), 1.61-1.77 (2H, m), 1.76-1.89 (1H, m), 1.94-2.06 (1H, m), 3.24 (3H, s), 3.27 (3H, d), 3.52-3.56 (1H, m), 3.75 (1H, td), 3.89 (1H, dd), 4.03 (1H, d), 4.15-4.37 (3H, m), 4.70-4.74 (1H, m), 6.94-7.06 (2H, m), 7.27 (1H, dd), 8.28 (1H, dd), 9.07 (1H, q); m/z: (ES+) MH$^+$, 460.50. Chiral SFC: (Berger Minigram, 5 μm Chiralcel OJ-H (250 mm×4.6 mm) column eluting with $CO_2$/MeOH/N, NDMEA 90/10/0.5) Rf, 10.59 99.8%.
and the title compound: 6-fluoro-N-methyl-1-{4-[(3R)-3-methylmorpholin-4-yl]-6-[1-((S)—S-methylsulfonimidoyl)cyclopropyl]pyrimidin-2-yl}-1H-benzimidazol-2-amine (36.5 mg, 2%) as the third eluting compound; $^1$H NMR (400 MHz, DMSO-d$^6$) 1.31 (3H, d), 1.44-1.54 (2H, m), 1.57-1.64 (1H, m), 1.77-1.82 (1H, m), 3.00-3.04 (6H, m), 3.33-3.37 (1H, m), 3.53 (1H, td), 3.67 (1H, dd), 3.81 (1H, d), 3.93-4.13 (3H, m), 4.49-4.51 (1H, m), 6.80 (1H, s), 6.93 (1H, ddd), 7.22 (1H, dd), 7.87 (1H, dd), 8.64 (1H, q); m/z: (ES+) MH$^+$, 460.50. Chiral SFC: (Berger Minigram, 5 μm Chiralcel OJ-H (250 mm×4.6 mm) column eluting with $CO_2$/MeOH/N, NDMEA 90/10/0.5) Rf, 12.72 97.4%.
and the title compound: 5-fluoro-N-methyl-1-{4-[(3R)-3-methylmorpholin-4-yl]-6-[1-((S)—S-methylsulfonimidoyl)cyclopropyl]pyrimidin-2-yl}-1H-benzimidazol-2-amine (80 mg, 4%) as the fourth eluting compound; $^1$H NMR (400 MHz, DMSO-d$^6$) 1.27 (3H, d), 1.43-1.51 (2H, m), 1.55-1.63 (1H, m), 1.72-1.83 (1H, m), 3.03 (3H, s), 3.06 (3H, d), 3.28-3.37 (1H, m), 3.52 (1H, td), 3.67 (1H, dd), 3.79 (1H, d), 3.93-4.14 (3H, m), 4.46-4.49 (1H, m), 6.72-6.82 (2H, m), 7.05 (1H, dd), 8.05 (1H, dd), 8.84 (1H, q); m/z: (ES+) MH$^+$, 460.50. Chiral SFC: (Berger Minigram, 5 μm Chiralcel OJ-H (250 mm×4.6 mm) column eluting with $CO_2$/MeOH/N, NDMEA 90/10/0.5) Rf, 25.03 99.5%.

The 4:1 mixture of R:S isomers of (3R)-4-(2-chloro-6-(1-(S-methylsulfonimidoyl)cyclopropyl)pyrimidin-4-yl)-3-methylmorpholine, used as starting material, was prepared as follows:

Sodium hydroxide (50%, 80 ml, 1496.99 mmol) was added to an approximate 4:1 mixture of R:S isomers of (3R)-4-(2-chloro-6-(S-methylsulfonimidoylmethyl)pyrimidin-4-yl)-3-methylmorpholine (10 g, 24.95 mmol), 1,2-dibromoethane (8.60 ml, 99.80 mmol) and tetraoctylammonium bromide (1.364 g, 2.49 mmol) in methyl THF (500 ml) at 20° C. under nitrogen. The resulting mixture was stirred at 20° C. for 24 hours. The reaction mixture was diluted with methyl THF (500 ml) and the aqueous layer separated. The mixture was diluted further with EtOAc (1000 ml) and washed with water (1500 ml). The organic layer was dried over MgSO$_4$, filtered and evaporated. The residue was purified by flash chromatography on silica, eluting with a gradient of 0 to 5% MeOH in DCM. Pure fractions were evaporated to dryness to afford an approximate 4:1 mixture of R:S isomers of (3R)-4-(2-chloro-6-(1-(5-methylsulfonimidoyl)cyclopropyl)pyrimidin-4-yl)-3-methylmorpholine (1.570 g, 19%); $^1$H NMR (400 MHz, DMSO-d$^6$) 1.18 (3H, d), 1.25-1.50 (3H, m), 1.59-1.71 (1H, m), 3.01 (3H, s), 3.19 (1H, t), 3.39-3.46 (1H, m), 3.52-3.61 (1H, m), 3.72 (1H, d), 3.86 (1H, s), 3.93 (1H, dd), 4.01-4.05 (1H, m), 4.38 (1H, s), 6.95 (1H, s); m/z: (ES+) MH$^+$, 331.39.

The invention claimed is:
1. A compound of formula (I):

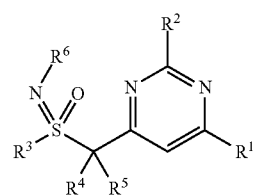

wherein:
R$^1$ is selected from morpholin-4-yl and 3-methylmorpholin-4-yl;
R$^2$ is

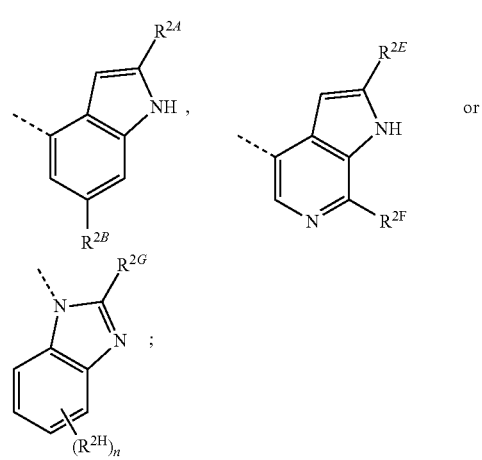

n is 0 or 1;

$R^{2A}$, $R^{2E}$ and $R^{2F}$ each independently are hydrogen or methyl;

$R^{2B}$ is hydrogen or methyl;

$R^{2G}$ is selected from —$NHR^7$ and —$NHCOR^8$;

$R^{2H}$ is fluoro;

$R^3$ is methyl;

$R^4$ and $R^5$ are each independently hydrogen or methyl, or $R^4$ and $R^5$ together with the atom to which they are attached form Ring A;

Ring A is a $C_{3-6}$cycloalkyl or a saturated 4-6 membered heterocyclic ring containing one heteroatom selected from O and N;

$R^6$ is hydrogen;

$R^7$ is hydrogen or methyl;

$R^8$ is methyl, or a pharmaceutically acceptable salt thereof.

2. The compound according to claim 1 wherein $R^4$ and $R^5$ together with the atom to which they are attached form Ring A, and Ring A is a $C_{3-6}$cycloalkyl or a saturated 4-6 heterocyclic ring containing one heteroatom selected from O and N.

3. The compound according to claim 1 wherein Ring A is a cyclopropyl, tetrahydropyranyl or piperidinyl ring.

4. The compound according to claim 1 wherein $R^{2A}$ is hydrogen; $R^{2B}$ is hydrogen; $R^{2E}$ is hydrogen; and $R^{2F}$ is hydrogen.

5. The compound according to claim 1 wherein $R^1$ is 3-methylmorpholin-4-yl.

6. The compound according to claim 4 wherein $R^1$ is 3-methylmorpholin-4-yl.

7. The compound according to claim 1 where the compound of formula (I) is a compound of formula (Ia),

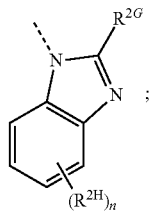

(Ia)

or a pharmaceutically acceptable salt thereof.

8. The compound according to claim 7, or a pharmaceutically acceptable salt, thereof wherein:

Ring A is cyclopropyl ring;

$R^2$ is

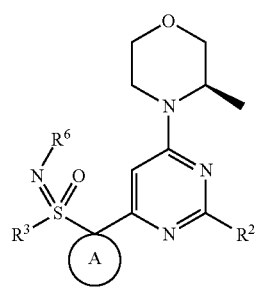

or

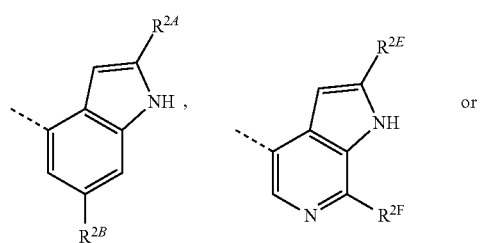

n is 0 or 1;

$R^{2A}$ is hydrogen;

$R^{2B}$ is hydrogen;

$R^{2E}$ is hydrogen;

$R^{2F}$ is hydrogen;

$R^{2G}$ is —$NHR^7$;

$R^{2H}$ is fluoro;

$R^3$ is a methyl group;

$R^6$ is hydrogen; and $R^7$ is hydrogen or methyl;

or a pharmaceutically acceptable salt thereof.

9. The compound according to claim 1 wherein the compound of formula (I) is selected from any one of:

N-Methyl-1-{4-[(3R)-3-methylmorpholin-4-yl]-6-[1-((R)—S-methylsulfonimidoyl)cyclopropyl]pyrimidin-2-yl}-1H-benzimidazol-2-amine;

N-Methyl-1-{4-[(3R)-3-methylmorpholin-4-yl]-6-[1-((S)—S-methylsulfonimidoyl)cyclopropyl]pyrimidin-2-yl}-1H-benzimidazol-2-amine;

4-{4-[(3R)-3-Methylmorpholin-4-yl]-6-[1-((R)—S-methylsulfonimidoyl)cyclopropyl]pyrimidin-2-yl}-1H-indole;

4-{4-[(3R)-3-methylmorpholin-4-yl]-6-[1-((S)—S-methylsulfonimidoyl)cyclopropyl]pyrimidin-2-yl}-1H-indole;

1-{4-[(3R)-3-Methylmorpholin-4-yl]-6-[1-((R)—S-methylsulfonimidoyl)cyclopropyl]pyrimidin-2-yl}-1H-benzimidazol-2-amine;

1-{4-[(3R)-3-methylmorpholin-4-yl]-6-[1-((S)—S-methylsulfonimidoyl)cyclopropyl]pyrimidin-2-yl}-1H-benzimidazol-2-amine;

4-Fluoro-N-methyl-1-{4-[(3R)-3-methylmorpholin-4-yl]-6-[1-((R)—S-methylsulfonimidoyl)cyclopropyl]pyrimidin-2-yl}-1H-benzimidazol-2-amine;

4-fluoro-N-methyl-1-{4-[(3R)-3-methylmorpholin-4-yl]-6-[1-((S)—S-methylsulfonimidoyl)cyclopropyl]pyrimidin-2-yl}-1H-benzimidazol-2-amine;

4-{4-[(3R)-3-Methylmorpholin-4-yl]-6-[1-(S-methylsulfonimidoyl)cyclopropyl]pyrimidin-2-yl}-1H-pyrrolo[2,3-c]pyridine;

N-methyl-1-{4-[1-methyl-1-((S)—S-methylsulfonimidoyl)ethyl]-6-[(3R)-3-methylmorpholin-4-yl]pyrimidin-2-yl}-1H-benzimidazol-2-amine;

N-methyl-1-{4-[1-methyl-1-((R)—S-methylsulfonimidoyl)ethyl]-6-[(3R)-3-methylmorpholin-4-yl]pyrimidin-2-yl}-1H-benzimidazol-2-amine;

N-Methyl-1-{4-[(3R)-3-methylmorpholin-4-yl]-6-[4-((S)—S-methylsulfonimidoyl)tetrahydro-2H-pyran-4-yl]pyrimidin-2-yl}-1H-benzimidazol-2-amine;

N-methyl-1-{4-[(3R)-3-methylmorpholin-4-yl]-6-[4-((R)—S-methylsulfonimidoyl)tetrahydro-2H-pyran-4-yl]pyrimidin-2-yl}-1H-benzimidazol-2-amine;

4-{4-[(3R)-3-Methylmorpholin-4-yl]-6-[4-((S)—S-methylsulfonimidoyl)tetrahydro-2H-pyran-4-yl]pyrimidin-2-yl}-1H-indole;

4-Fluoro-N-methyl-1-{4-[1-methyl-1-((S)—S-methylsulfonimidoyl)ethyl]-6-[(3R)-3-methylmorpholin-4-yl]pyrimidin-2-yl}-1H-benzimidazol-2-amine;
4-fluoro-N-methyl-1-{4-[1-methyl-1-((R)—S-methylsulfonimidoyl)ethyl]-6-[(3R)-3-methylmorpholin-4-yl]pyrimidin-2-yl}-1H-benzimidazol-2-amine;
6-Fluoro-N-methyl-1-{4-[1-methyl-1-((R)—S-methylsulfonimidoyl)ethyl]-6-[(3R)-3-methylmorpholin-4-yl]pyrimidin-2-yl}-1H-benzimidazol-2-amine;
5-Fluoro-N-methyl-1-{4-[1-methyl-1-((R)—S-methylsulfonimidoyl)ethyl]-6-[(3R)-3-methylmorpholin-4-yl]pyrimidin-2-yl}-1H-benzimidazol-2-amine;
5-Fluoro-N-methyl-1-{4-[1-methyl-1-((S)—S-methylsulfonimidoyl)ethyl]-6-[(3R)-3-methylmorpholin-4-yl]pyrimidin-2-yl}-1H-benzimidazol-2-amine;
6-fluoro-N-methyl-1-{4-[1-methyl-1-((S)—S-methylsulfonimidoyl)ethyl]-6-[(3R)-3-methylmorpholin-4-yl]pyrimidin-2-yl}-1H-benzimidazol-2-amine;
6-Fluoro-N-methyl-1-{4-[(3R)-3-methylmorpholin-4-yl]-6-[1-((R)—S-methylsulfonimidoyl)cyclopropyl]pyrimidin-2-yl}-1H-benzimidazol-2-amine;
5-fluoro-N-methyl-1-{4-[(3R)-3-methylmorpholin-4-yl]-6-[1-((R)—S-methylsulfonimidoyl)cyclopropyl]pyrimidin-2-yl}-1H-benzimidazol-2-amine;
5-fluoro-N-methyl-1-{4-[(3R)-3-methylmorpholin-4-yl]-6-[1-((S)—S-methylsulfonimidoyl)cyclopropyl]pyrimidin-2-yl}-1H-benzimidazol-2-amine; and
6-fluoro-N-methyl-1-{4-[(3R)-3-methylmorpholin-4-yl]-6-[1-((S)—S-methylsulfonimidoyl)cyclopropyl]pyrimidin-2-yl}-1H-benzimidazol-2-amine;
or a pharmaceutically acceptable salt thereof.

10. A pharmaceutical composition comprising a compound of formula (I), or a pharmaceutically acceptable salt thereof, according to claim 1 in association with a pharmaceutically acceptable adjuvant, diluent or carrier.

* * * * *